(12) United States Patent
Merriman et al.

(10) Patent No.: US 7,169,925 B2
(45) Date of Patent: Jan. 30, 2007

(54) INDOLE DERIVATIVES AS INTERLEUKIN-4 GENE EXPRESSION INHIBITORS

(75) Inventors: Gregory H. Merriman, Phillipsburg, NJ (US); Philip M. Weintraub, Warren, NJ (US); Jeffrey S. Sabol, Bridgewater, NJ (US); Ramalinga M. Dharanipragada, Belle Mead, NJ (US); Nicholas J. Hrib, Hillsborough, NJ (US); John G. Jurcak, Bethlehem, PA (US); Alexandre Gross, Jersey City, NJ (US); Brian Whiteley, Lebanon, NJ (US); Kwon Yon Musick, Raritan, NJ (US); Joseph T. Klein, Neshanic Station, NJ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 162 days.

(21) Appl. No.: 10/421,511

(22) Filed: Apr. 23, 2003

(65) Prior Publication Data
US 2004/0010029 A1    Jan. 15, 2004

Related U.S. Application Data

(60) Provisional application No. 60/375,304, filed on Apr. 23, 2002.

(30) Foreign Application Priority Data
Aug. 2, 2002    (GB) ................. 0217920.8

(51) Int. Cl.
C07D 403/12    (2006.01)
C07D 401/00    (2006.01)
(52) U.S. Cl. .............. 544/333; 544/335; 546/201
(58) Field of Classification Search ........ 546/201; 544/333, 338
See application file for complete search history.

(56) References Cited

U.S. PATENT DOCUMENTS 5,177,088 A * 1/1993 Effland et al. .......... 514/339
5,189,054 A    2/1993 Salituro et al.
5,328,920 A * 7/1994 Effland et al. .......... 514/339
5,491,153 A    2/1996 Salituro et al.

FOREIGN PATENT DOCUMENTS

| EP | 0186367 | 3/1993 |
|----|---------|--------|
| WO | WO 95/24408 | 9/1995 |
| WO | WO 97/13768 | 4/1997 |
| WO | WO 00/46199 | 8/2000 |

OTHER PUBLICATIONS

A. Sydney Bailey et al., Further Examination of the Reactions of Simple Indoles with Arenesulphonyl Azides, Journal of the Chemical Society, Perkin Transactions 1 (1973, pp. 1602-1606, vol. 15).
Carmen Galvez et al., New Routes to Condensed Thiophene Ring Systems From Ortho-Diaminothiophene Derivatives, J. Chem. Research (1985, pp. 296-297, vol. 9).
David M. Mckinnon, et al., The Conversions of Isothiazolium Salts Into Thiophenecarboxylic Ester Derivatives, Can. J. Chem. (1984, pp. 1580-1584, vol. 62(8).
Tomohiro Yoshimoto et al., Role of NK1.1+ T Cells in a TH2 Response and in Immunoglobulin E Production, Science (1995, pp. 1845-1847, vol. 270).

* cited by examiner

*Primary Examiner*—Thomas McKenzie
*Assistant Examiner*—Raymond Covington
(74) *Attorney, Agent, or Firm*—Balaram Gupta

(57) ABSTRACT

This invention discloses and claims a new class of indole derivatives for use in treating allergy, asthma, rhinitis, dermatitis, B-cell lymphomas, tumors and diseases associated with bacterial, rhinovirus or respiratory syncytial virus (RSV) infections. It has now been found that the compounds of this invention are capable of modulating T helper (Th) cells, Th1/Th2, and thereby capable of inhibiting the transcription of interleukin-4 (IL-4) message, IL-4 release or IL-4 production.

11 Claims, 8 Drawing Sheets

Effect of 3-(4-pyridinylamino)-1H-indole-2-carboxylic acid (Example 28) on BALF Cytokines and Lung Inflammation in Mice Inhibition by 3-(4-pyridinylamino)-1H-indole-2-carboxylic acid (Example 28) of allergen-induced lung inflammation in the rat The effect of 3-(4-pyridinylamino)-1H-indole-2-carboxylic acid (Example 28) on early and late phase allergic pulmonary responses in sheep following challenge with *Ascaris suum* antigen

FIG. 4

SEQ ID NO: 1 - A 6.7 kb Fragment Comprising Nucleotides -6635 to +66 of Human Interleukin-4 Gene Promoter GAATTCCTTCCTGTGCGAGATCCAAGAACTCTCTCGGGGTCTGAATCGGGACC
CCTTTTTCCAGCAACACTGTGTTCTTCCCCTTGGCTTAGTCACCCTCCATGTCTA
CTGCCTGCAGGCTGGACCCTCCCCTGTTCTCAGAGTATGGCCCGTAGCAGCCC
CTCAGCTGGTGGCTCCCACCCGCCGCCTGCCCTCTCCCCTGCCTCCTCCCCAAG
CCAGAGACCTGGGGCCACCTGCGACTTCCTGCTCTCCCTCACCCCACATTCA
GTCACTTCCAAGTGCTATTAATGATGATGGTGGTGGTGATGGTGATTGCTGGC
ATTTTCCGGGGGCTTGCAATATGCCGGTCACCACACCAAACACTTCATATTTGT
CACCTTCTATAGTATTCCCTCGCCCCTGTAATCAGCCCAGTTTTACAGAGAAGC
CTGGATGGGGGAACTTTTCCAAGGTCACCCAGAGCTGGGATTCAGAACCAGTC
AGGTCCCGTGGGCACCAAGACACCAGGTCTTAACCTAGACACTGTGCTGGGCC
AAATGACTCAAGAGCCCACAGCTCTCCCTGCCACCATCCCACCCGATTCGCGC
CAGCTGCCTCTGTCACGGGCGCCTGCAATGCTCTGGCTGGGTCCCCTCGGCCC
GTGCTCCCCTCCTGGGAGCCCTCTCTTCAGTGACCTCGGGGCCTTCCACCTGTC
TGTCCCTTGCCCGCACTCACCCCACCCTGCAGCCCCTGCTCCTGGCTAAAGCC
GGCTCATCCCTAACTCTGCTTAAGTGCCCCTCCCTCAGAGAAGTCTCACCTTTT
TCCATGACTAAGCCTGTGGGGGTTGGAAAGCACTCTCCTGGGTGCTGGCCTGC
AGGACTGACAGAAGAGGAGGGAGGTGAGATTCACCCGACTCGGACCACAGGA
ATGGCTGGGACAGCAAGCATCAATGAACGAGGCCCGTGGAGACTGGGCTGCA
TTGTGCGACCTGTATTCCTTTCTCCTAGTTGACTGCCGCGTTTCTGACTCCTTTG
AAGCGAGCATCTGGCTTTTCCAATTAGATGAAGGCTGACAAGCTGTGGAGGGG
AGGGCGGCAGATACCATGTACCTGGTCATTCAGACTAGGGGTGTCCTTGAGCA
GACTCATGGTGTGGAAGTCAGACCGGGAGTCTCCTGGAGCAGACTCACAGTGT
AGGGGGTCAGCAGAGGCAGCAGCTTTGGAATCCCGGCACTGCAGCCTCAGGG
GTGGCTCGCTGAGTGGGTCAGGTCTTTAGGGTTCTGGGCCCAGCCTGGAGCCT
GCCCCTCCAGCCCTCCTGACATTCTTAGAAGCACCTACTTTCCTGCCTAAATCC
TTTCCTGACTAAAGCACCCACAGCTGTGTCTGTTCCCTGTAATGAATCCAGAT
ACTAAAGTAGGCGGGCTGCAGTGTGGAGACCGTGACCCACCAGAAACAAGGA
CGGCAACTCAAAGACGGAGGAGGCACATCCAGGAGGAACCTGTGGGGAGGGC CCGTCTGGCCAGATCTCCACTGCCCTGTCCAGACTTGGGCTTGCCTAATAGAT
GAAGCATCAGTCATTTCAGCAACTCAAGATAGGAGTCATCATTATCATCATCA
CACTCACTGTGTGCCAGGCACTATTCTAAATACTTGAAAACTTTAAATGTATTC
ATTCCTCAGAGCAACTTCATGAGACAGGGACAGCTATGACCCCTATTTCACAG
ATGAGGCTGAGTAGCGTGCCCAAGGTCACACAGCCAGGAGGCACAGCAGCCA
GGCCTGACAGACCACCTGGGCCCAGCGTCCGCTCTCTTAGCCACCGTGTACTA
TAGCAGCCTCTGTTAACAGACCCCTTTCTGGATGACACATGCCAAGTACTTTCC
ATGGAACCACTCACTTGCTCCTCACAAGGAAGAGCCACATTATTCCCATTTCA
CAGGTGAGAAAATCGAGACCCAGAGAGAGTTAATGATCTACTCATGGTCACA
GAGTTGATAAGGGCTCATTTGCTGGACTCCCAAACGCAGTGCTCATAACTGCT
ACGTTCCAGGGCCTGAAGGAAAAACTCTGCATCCATGGAGGGGCCGGCGCTG
GTTCTCAGCTCTCACACAGGGGAGGGGAAGGGGCCTGTGACCGACACAGCCA
GAGACAGCAGTATTCACCTCCCTCCTGAACTTTGGTGTCAGGCCCACCACACC
CCGCCAAGGCACTGCCCATGGCCCTGAGGCTCGGAGACTCCTTCGCAGTGGTG
GTAGTGGTGGTGATCACTGCCCTCCTCTTTGTCCCTGCAATGCAGGCACCCACC
TTCCCCATCTCTACCCACCTGCCGCACCTGCAGCTGCCATGGTGCTGTCCCTGC
AGGCGAGGATGGCCCATCCCCCACTTCTGCCCTCTGGGGAGACTCCTGGTCAC
TCTCGAATGTTCTGGACAGTTTATCCTTTCATCTTTGGCCTCATTTCACCATTGA
AACAAACAAAAAGCTGGATTCTGCTTCTGAGCTGAAGGTGCCCACCTAATAT
TCCCTTTTCACTCACCAGCTCTCCCTCAGAGCCTCAAGCCCAGGGTCTGCCCTT
TAGTGGGTGCTTAGAAAAACACCAGATGGACCATAAATGGCTGTTCCACTGCC
CCCACAGACGCCCCAGAACCCCGCCCTCCCCACCAGCTCCCCTTCTGCATCCC
CGACTCTCCTTGAGAACCTATTTGGCAGAAGCTCTCCACCCAGCAAGTCCGCA
GCTTGATGAGCTCCCTCCTGTGTTAACTGGAACCGCTGCTGTACTTCATTCCAC
ATAATAGTTATCGGATCCAAAGTCCCCACCTGCTTTGGAAGCAACCACCTGCT
CTTCTCATAACTCTCCTCCATTTGTGCAGTGAAGAATCAACCTTTATCCAAGAA
GTCTGGCCTTTGTCCTGGCTCTTGGGAGGTCCTACCAGCTACAAACCCTTGGA
GTAAACA

FIG. 4 (CONT.)

ACGTGGCTAGTCCTTGTCACCAGTTCCCAGGAGGTAGCCCCAAATTCCTAGGG
ATTTCCCAAGTGATAGGAGTATCTTATTATTCATGGTGGTCTCTGAGAGTTTAT
GCGAGTGAAGTGACTCATGGTGGGCCCTAGGTAGTTTTTGCTGACAATACGAC
ATGGAGGGGCTGGCCACGCCACTGAGGTTCTGTGATATCAGCCTGGCCTCCCG
GAAGGAGACAGGAAGATGAGTTCAACCCAGTGGCCAATGAGTCCATCAACCA
CACCTATATGATAAGACTCAAATAAAACTCTGGACCCCAAAGCTCAAGTGAG
CCTCCCTGCTTAGAAATAGTCAGCATTTGTCACACGTCAAAGTGCTGAGAAG
GTGATGCCTCTGACGCCACACGGGGAAGACAATGAGACTTTGTGTTTGGGCCC
CTCCTCCATCTCGCCCTGTGTCTCCTCTTTTGGCTGGTTCTGATTTGATGCTTT
TGTTATGATAAACTGTGGCCTTACGTATAGCACTCTCCTGAGTTCTGTCAGTC
ATCCAGTGCATTCTGGAACCTGAGGGGTAGTGGAAACTCCCAGATTTGCAGCC
AGTCAGCAGTGAGGTGGGCTGGGAACCCCTGAATGTGCAACTGGCGTCTGAA
GCAAGGGCAGTGTTGTGGGGACCATACCCCTCACCTGTGAGGTGTGGCTCAT
CTCAGGTGGTTTGGCATCTGAAGCCACTGCATTTGTTTGGTAACCTTGCTGCCC
AGTCCCAATGGAAGGATCCTAAATATGGTCTAAGGACCTCCTGTAACAATTAT
CCAGATTCTCTCCTTCACAGAACTTGAGGCACTGCGATAAGATCCAAAACTAT
TATACACAGTGGAATCCTATACAGCCTTAAAAAAGAAGGAAACGCTGTCATTC
ACCACAACAGGATGAACCTGGAGGACATTATGCTAAGTGAAAAAATCCAGGC
ACAGACAGACAAATACCACATGATCTCACGCATATGTGAAATATAAAAAAGC
CAAACTCAGGGAGGCAGAGAGTAGGATGAGTCACCAGGGCCTGGGAGGGTGG
TGATCAGGAAGATGTTGCTCAAAGGATATAAAATTTCAATGGGAGGAGTTAAG
TTAAAGAGAGCCATTGTACGACATGGTGACAACAGTTGATATCAATGTTTGTA
TACTTAAAAATCATGAAGACAGGCCAGGCGCAGTGGCTCACACCTGTAATCCC
AGCACTGCAGGGGCTGAGGTGGGTAGATCACCTGAGGTCAGGAGTTCGAGAC
CAGCCTGGCCAACATGGTAAAACCCTGTCTCTATTAAAAATACAAAAATTAGC
TGGGCGTGGTGGCAGGCACCTGTAACCAGCTACTCGGGAGGCTGAGGCAGGA
GAATTGCTTGAGCTCAGGAGGCAGAGGTTGCAGTGGCTGAGACTGCGCCATTG
CACTCCAGTCTGGGAACAGAGCAAGACTCTATCTCAAAATAAATATAAATCA
CAGAGTAGATTTTAAATGTTCTTACC

FIG. 4 (CONT.)

```
AAAAATAAATATGTGAAGTATTGTATAAGTAGCTTGATGTAGCAATTCCATAA
CATGCACATTTCAAAACATTATATCATACAGCACAAATATGTGCAATACTTAT
TTGTCAATTTAATAATAATAATAATAAGGGAAGAAAAGATCCAAAACAGGCA
AAACCTTGGCCGGGCATGGTGGTTCACGCCTATAATCCCAGCACTTTGGGAGG
CTGAGGGGGTGGATCATTTTGAGGCCAGGAGTTCGACACCAGCCTAGCCAACA
TGGTGAAACCCCATCTTACTAAAAAAAAAAAAAAAATACAGAAATTAGCCAG
GCGTGGTGGCATGTGCCTGTAATCCCGCTACTCGGGAAGCTGAGGCTGGAGAA
TGCCTTGAGCCCAGGAGATCAAGGCTACAGAAAGCTATGATCACCACTGCACT
CCAGCCTGGGTGACAGAGTATGGGGGCAGGGGGTGGTGAGGGGGCGGGGA
AGTGGAACAGAGCCAAAACCTTAGCAACACACATTTTTAGATGATCTTCCAGA
ATATTCATAGGGAGGCCCAGGCACAGTGGCTCACGCCTGTAATCCCAGCACTT
TGGGAGGCCGAGCAGGCGGATCACGAGGTCAGGAGATGGAGACCATCCTGGC
TAACACGGTGAAACCCCGTCTCTACTAAAAATACAAAAAATTAGCCGGGCGTG
GTGGCAGGTGCCTGTAGTCCCAGCTACTCGGGAGGCTGAGGCAGGAGAACGG
CATGAACCCAGGAGGCGGAGCTTGCAGTGAACTAAGATCCGCCACTGCACTC
CAGCCTGGGTGACAGAGCAAGATTCCATCTCAAAAAAAAAAAAAAAAAAGA
AATTCATAGGGAAAAGAAGGTCAGAGACCAAGGGAAGGGAAGGTTCTGGGAG
AAAAGCGGGGCAGGCAGGGCCCAAGAATCCTGCTGCCCATGAGCCCTTACTG
GGAGGTGGGGTGGCCTGCACAGGGCCCAGGCACCTGAGTGAGTGGTGGGGTC
CTTACGTTCACTGCTGGGGTGAGGCATGAGCACCTTATTGTGTCCACATGAATT
CAATAAAAAACAAGCAGGGCGCGTGGTGGGGCACTAGGAGGGCTGATTTGTA
AGTTGGTAAGACTGTAGCTCTTTTTCCTAATTAGCTGAGGATGTGTTAGGTTCC
ATTCAAAAAGTGGGCATTCCTGGCCAGGCATGGTGGCTCACACCTGTAATCTC
AGGCTTTGGGAGACTGAGGTAGGAGGATCACTTGAGCCCAGGAATTTGAGAT
GAGCCTAGGCAACATAGTGAGACTCTTATCTCTATCAAAAATAAAATAAAA
ATGAGCCAGGCATGGTGCGGTGACCACGCACCTACTGCTAGGGGGGCTGAGG
TGGGAGGATCATTGAGCCTGGGAGGTTGAGGTGCAGTGATCCCTGATCAAACA
TTGCATTTCAGCCTGGGTGACAGAGTGAGACCCTGTCTCAGAAAAAAAAAA
AAAGTCATTCCTGAAACCTCAG
```

FIG. 4 (CONT.)

```
AATAGACCTACCTTGCCAAGGGCTTCCTTAGGGTAAGGACCTTATGGACCTGC
TGGGACCCAAACTAGGCCTCACCTGATACGACCTGTCCTCTCAAAACACTAAA
CTTGGGAGAACATTGTCCCCAGTGCTGGGGTAGGAGAGTCTGCCTGTTTCTG
CCTCTATGCAGAGAAGGAGCCCCAGATCATCTTTTCCATGACAGGACAGTTTC
CAAGACCACCTGTACTTGGAAGAAGCCAGGTTAAATACTTTTCAAGTAAAAC
TTTCTTGATATTACTCTTCTTTCCCCAGGAGGACTGCATTACAACAAATTCGGA
CACCTGTGGCCTCTCCCTTCTATGCAAGCAAAAGCCAGCAGCAGCCCCAAGC
TGATAAGATTAATCTAAAGAGCAAATTATGGTGTAATTTCCTATGCTGAAACT
TTGTAGTTAATTTTTAAAAGGTTTCATTTTCCTATTGGTCTGATTCACAGGA
ACATTTTACCTGTTTGTGAGGCATTTTTCTCCTGGAAGAGAGGTGCTGATTGG
CCAGTGACTGACAATCTGGTGTAACGAAAATTCCAATGTAAACTCATTTTCC
CTCGGTTTCAGCATTTAAATCTATATATAGAGATATCTTTGTCAGCATTGCATC
GTTAGCTTCTCCTGATAAACTAATGCCTCACATTGTCACTGCAAATCGACACCT
ATTA
```

FIG. 4 (CONT.)

INDOLE DERIVATIVES AS INTERLEUKIN-4 GENE EXPRESSION INHIBITORS

This application claims the benefit of U.S. Provisional Application No. 60/375,304, filed Apr. 23, 2002.

BACKGROUND OF THE INVENTION

1. Field of the Invention

The present invention relates to a series of indole derivatives. More specifically, the present invention relates to a series of substituted 3-aminoindole carboxylic acid derivatives and their bioprecursors. The compounds of this invention include prodrugs, analogs and/or bioprecursors of the active parent compounds. The parent compounds are capable of modulating T helper (Th) cells, thus controlling the transcription of interleukin-4 (IL-4) message, IL-4 release or IL-4 production, and therefore, exhibit a wide variety of therapeutic utility.

2. Description of the State of the Art

It is generally known that lymphocytes, which are produced in the bone marrow, are a class of cells that control the immune system. It is also known in the art that a class of lymphocytes known as T cells, which are educated in the thymus, are further subcategorized into helper T cells, which enhance or activate the responses of other white blood cells, such as macrophages or B cells, by secreting a variety of local mediators, lymphokines, interleukins and/or cytokines. Within this class of T cells, there are two T cell subsets, normally referred to as Th1 and Th2 cells which are distinguished by the array of cytokine genes, each cell type expresses and appears to be involved in different types of immune responses.

If uncontrolled, Th1 cells are implicated in the pathogenesis of autoimmune diseases such as type-1 diabetes, rheumatoid arthritis and multiple sclerosis (MS). Also it is known that Th2 cells are important in the eradication of helminthes and other extracellular parasites and are involved in allergic and atopic reactions. Cytokines produced by Th2 cells can induce airway hyperreactivity as well as production of IgE. Th2 cells express cytokines IL-4, IL-5 and IL-13 and can activate mast cells and eosinophils. Th2 cells stimulate B cells to proliferate and secrete antibodies effectively (humoral immunity).

Interleukin-4 is a pleiotropic type I cytokine produced by Th2 cells, basophils and mast cells, in response to receptor-mediated activation events. IL-4 is also produced by a specialized subset of T cells, some of which express NK1.1 and appear to be specific for CD-1 (NK T cells), Yoshimoto, T., et al., *Science* (1995) 270:1845–1847. T cells have been reported to produce IL-4, and mice lacking these cells fail to develop IL-4-dependent airway hypersensitivity upon immunization with ovalbumin in alum. Eosinophils have also been reported to be capable of producing IL-4.

IL-4 plays a central role in regulating the differentiation of antigen-stimulated naive T cells. IL-4 causes such cells to develop into cells capable of producing IL-4 and a series of other cytokines including IL-5, IL-10 and IL-13 (i.e. Th2-like cells). IL-4 powerfully suppresses the appearance of IFN-γ-producing CD4+T cells, e.g., $T_H1$ cells. A second function of major physiologic importance is IL-4's control of the specificity of immunoglobulin class switching. IL-4 determines that human B cells switch to the expression of IgE and IgG4 and mouse B cells to IgE and IgG1. In IL-4 and IL-4 receptor knockout mice, as well as in mice that lack a principal substrate of the IL-4 receptor Stat-6, IgE production is diminished by a factor of 100-fold or more. IL-4 receptor knockout mice and Stat-6 knockout mice are also deficient in the development of IL-4-producing T cells in mice infected with the helminthic parasite *Nippostrongylus brasiliensis*. These physiologic functions of IL-4 give it a preeminent role in the regulation of allergic conditions; it also plays a major role in the development of protective immune responses to helminths and other extracellular parasites. In experimental and clinical situations, IL-4 appears to be capable of ameliorating the effects of tissue-damaging autoimmunity.

Thus, it is an object of this invention to provide a series of compounds that are useful in treating a wide variety of disease states caused by the imbalance of Th1/Th2 cells. Such disease states include, but not limited to, allergy, asthma, rhinitis, dermatitis B-cell lymphomas, tumors and diseases associated with bacterial, rhinovirus or respiratory syncytial virus (RSV) infections.

It is also an object of this invention to provide compounds that are capable of modulating T helper (Th) cells, Th1/Th2, thereby diminishing the number of Th2 cells in reference to the Th1 cells.

It is further an object of this invention to provide compounds that are capable of inhibiting the transcription of interleukin-4 (IL-4) message, IL-4 release or IL-4 production.

Finally, it is an object of this invention to provide compounds, which are indole derivatives that satisfy all of the objects, described hereinabove.

Other objects and further scope of the applicability of the present invention will become apparent from the detailed description to follow.

All of the references described herein are incorporated herein by reference in their entirety.

SUMMARY OF THE INVENTION

Thus in accordance with the practice of this invention there is provided a compound of the formula (I):

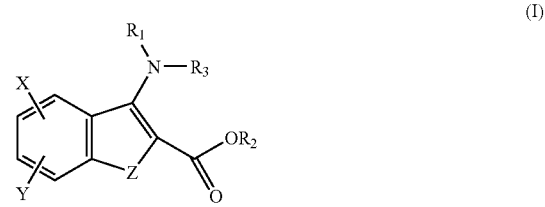

wherein

X and Y are the same or different and are independently selected from the group consisting of hydrogen, halogen, nitro, amino, hydroxy, $C_{1-6}$alkyl, $C_{2-6}$alkenyl, $C_{2-6}$alkynyl, $C_{1-6}$alkoxy, $C_{1-6}$perfluoroalkyl, $C_{1-6}$perfluoroalkoxy, phenyl and benzyl, wherein phenyl or benzyl is optionally substituted with one or two substituents each independently selected from $C_{1-6}$alkyl, $C_{1-6}$perfluoroalkyl, halogen, hydroxy or $C_{1-6}$perfluoroalkyl or $C_{1-6}$perfluoroalkoxy;

Z is N—R or S, wherein R is selected from the group consisting of hydrogen, $C_{1-6}$alkyl, $C_{1-6}$alkylcarbonyl, $C_{1-6}$alkoxycarbonyl $C_{1-6}$alkyl, $C_{1-6}$alkylcarbamoyl-$C_{1-6}$alkyl and $C_{1-6}$dialkylcarbamoyl $C_{1-6}$alkyl;

$R_1$ is selected from the group consisting of hydrogen, $C_{1-6}$alkyl, $C_{2-6}$alkenyl, $C_{2-6}$alkynyl, $C_{1-6}$perfluoroalkyl, $C_{3-8}$cycloalkyl, $C_{3-8}$cycloalkyl $C_{1-6}$alkyl, $C_{1-6}$alkoxy$C_{1-6}$ alkyl, hydroxyC$_{1-6}$alkyl, aminoC$_{1-6}$alkyl, mono- or di-C$_{1-6}$alkyl-aminoC$_{1-6}$alkyl, formyl, C$_{1-6}$alkylcarbonyl, amino C$_{1-6}$alkylcarbonyl, C$_{1-6}$alkoxycarbonyl, phenyl, diphenylC$_{1-6}$alkyl and phenylC$_{1-6}$alkyl, phenylcarbonylC$_{1-6}$alkyl, phenoxyC$_{1-6}$alkyl, wherein phenyl is optionally substituted with one or two substituents each independently selected from C$_{1-6}$alkyl, C$_{1-6}$perfluoroalkyl, halogen, hydroxy or C$_{1-6}$perfluoroalkyl or C$_{1-6}$perfluoroalkoxy;

R$_3$ is

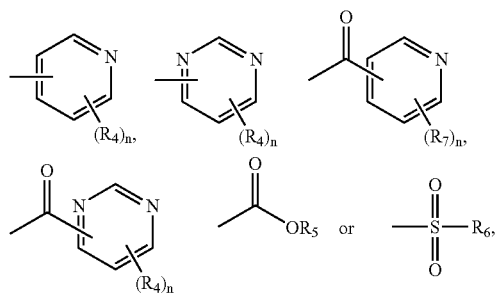

wherein
R$_4$ is selected form the group consisting of hydrogen, halogen, nitro, amino, hydroxy, C$_{1-6}$alkyl, C$_{1-6}$alkoxy, C$_{1-6}$perfluoroalkyl, C$_{1-6}$perfluoroalkoxy, N-morpholinylcarbonyl, phenyl and benzyl, wherein phenyl or benzyl is optionally substituted with one or two substituents each independently selected from C$_{1-6}$alkyl, C$_{1-6}$perfluoroalkyl, halogen, hydroxy, C$_{1-6}$alkoxy or C$_{1-6}$perfluoroalkoxy;

R$_5$ is selected from the group consisting of C$_{2-8}$alkyl, C$_{3-8}$cycloalkyl, C$_{2-6}$alkenyl, C$_{2-6}$alkynyl, pyridyl, phenyl, styryl, benzyl, diazophenyl, naphthyl and quinolinyl, wherein cycloalkyl, pyridyl, phenyl, styryl, benzyl, diazophenyl, naphthyl or quinolinyl is optionally substituted with one or more substituents each independently selected from C$_{1-6}$alkyl, C$_{1-6}$perfluoroalkyl, nitro, amino, dimethylamino, acetamido, halogen, hydroxy, C$_{1-6}$alkoxy or C$_{1-6}$perfluoroalkoxy;

R$_6$ is selected from the group consisting of C$_{6-12}$bicycloalkyl, styryl, thiazolyl, diazophenyl, naphthyl and quinolinyl, wherein bicycloalkyl, styryl, thiazolyl, diazophenyl, naphthyl or quinolinyl is optionally substituted with one or more substituents each independently selected from C$_{1-6}$alkyl, C$_{1-6}$perfluoroalkyl, nitro, amino, dimethylamino, acetamido, halogen, hydroxy, C$_{1-6}$alkoxy or C$_{1-6}$perfluoroalkoxy;

R$_7$ is selected from the group consisting of halogen, nitro, amino, hydroxy, C$_{1-6}$alkyl, C$_{1-6}$alkoxy, C$_{1-6}$perfluoroalkyl, C$_{1-6}$perfluoroalkoxy, N-morpholinylcarbonyl, phenyl and benzyl, wherein phenyl or benzyl is optionally substituted with one or two substituents each independently selected from C$_{1-6}$alkyl, C$_{1-6}$perfluoroalkyl, halogen, hydroxy, C$_{1-6}$alkoxy or C$_{1-6}$perfluoroalkoxy; and n is an integer from 0 to 3; and R$_2$ is selected from the group consisting of hydrogen, C$_{1-6}$alkyl, C$_{1-6}$perfluoroalkyl, perfluoroaryl, indanyl, C$_{1-6}$alkoxyC$_{1-6}$alkyl, C$_{2-6}$acyloxyC$_{1-6}$alkyl, C$_{1-6}$alkoxycarbonylC$_{1-6}$alkyl, C$_{1-6}$alkoxycarbonyloxyC$_{1-6}$alkyl, C$_{3-8}$cycloalkyl, C$_{3-8}$cycloalkoxycarbonyloxy-C$_{1-6}$alkyl, adamantyloxycarbonyloxyC$_{1-6}$alkyl, C$_{3-8}$cycloalkoxycarbonyl-C$_{1-6}$alkyl, mono- or di-C$_{1-6}$alkylamino-C$_{1-6}$alkyl, C$_{3-8}$azacycloalkylC$_{1-6}$alkyl, mono- or di-C$_{1-6}$alkylcarbamoyl-C$_{1-6}$alkyl, C$_{3-8}$azacycloalkylcarbonyloxyC$_{1-6}$alkyl, benzylC$_{1-6}$alkylcarbamoylC$_{1-6}$alkyl, mono- or di-C$_{1-6}$alkylcarbamoyloxyC$_{1-6}$alkyl, C$_{3-8}$azacycloalkylcarbonyloxy-C$_{1-6}$alkyl, benzylC$_{1-6}$alkylcarbamoyloxy-C$_{1-6}$alkyl, benzylcarbamoyloxyC$_{1-6}$alkyl, C$_{1-6}$alkoxycarbonylamino-oxo-C$_{1-6}$alkyl,

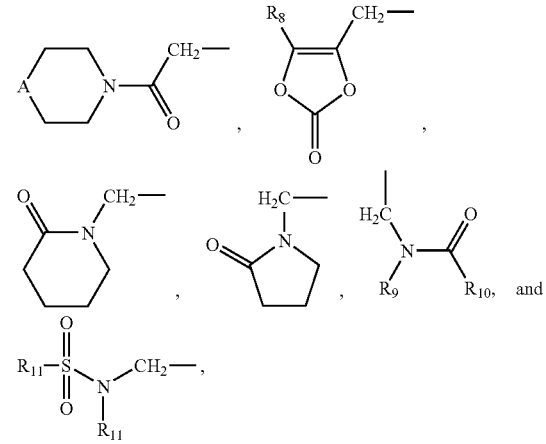

wherein
R$_8$ is hydrogen or C$_{1-6}$alkyl,
R$_9$ is C$_{1-6}$alkyl or phenyl,
R$_{10}$ is hydrogen, C$_{1-6}$alkyl or C$_{1-6}$alkoxycarbonylC$_{1-6}$alkyl,
R$_{11}$ is C$_{1-6}$alkyl, phenyl or tolyl, and
A is CH$_2$, NH or O, or a pharmaceutically acceptable salt thereof, with the proviso that when Z is N—R, and when both X and Y are hydrogen, R$_2$ is not hydrogen or C$_{1-6}$alkyl.

In another aspect of this invention there is also provided a compound of formula (II):

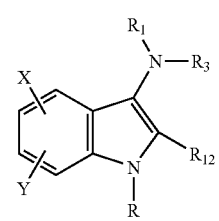

(II)

wherein
X and Y are the same or different and are independently selected from the group consisting of hydrogen, halogen, nitro, amino, hydroxy, C$_{1-6}$alkyl, C$_{2-6}$alkenyl, C$_{2-6}$alkynyl, C$_{1-6}$alkoxy, C$_{1-6}$perfluoroalkyl, C$_{1-6}$perfluoroalkoxy, phenyl and benzyl, wherein phenyl or benzyl is optionally substituted with one or two substituents each independently selected from C$_{1-6}$alkyl, C$_{1-6}$perfluoroalkyl, halogen, hydroxy or C$_{1-6}$perfluoroalkyl or C$_{1-6}$perfluoroalkoxy;

R is selected from the group consisting of hydrogen, C$_{1-6}$alkyl, C$_{1-6}$alkylcarbonyl, C$_{1-6}$alkoxycarbonylC$_{1-6}$alkyl, C$_{1-6}$alkylcarbamoyl-C$_{1-6}$alkyl and C$_{1-6}$dialkylcarbamoylC$_{1-6}$alkyl;

$R_1$ is selected from the group consisting of hydrogen, $C_{1-6}$alkyl, $C_{2-6}$alkenyl, $C_{2-6}$alkynyl, $C_{1-6}$perfluoroalkyl, $C_{3-8}$cycloalkyl, $C_{3-8}$cycloalkyl$C_{1-6}$alkyl, $C_{1-6}$alkoxy$C_{1-6}$alkyl, hydroxy$C_{1-6}$alkyl, amino$C_{1-6}$alkyl, mono- or di-$C_{1-6}$alkyl-amino$C_{1-6}$alkyl, formyl, $C_{1-6}$alkylcarbonyl, amino$C_{1-6}$alkylcarbonyl, $C_{1-6}$alkoxycarbonyl, phenyl, diphenyl$C_{1-6}$alkyl and phenyl$C_{1-6}$alkyl, phenylcarbonyl$C_{1-6}$alkyl, phenoxy$C_{1-6}$alkyl, wherein phenyl is optionally substituted with one or two substituents each independently selected from $C_{1-6}$alkyl, $C_{1-6}$perfluoroalkyl, halogen, hydroxy or $C_{1-6}$perfluoroalkyl or $C_{1-6}$perfluoroalkoxy;

$R_3$ is

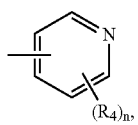

wherein $R_4$ is selected form the group consisting of hydrogen, halogen, nitro, amino, hydroxy, $C_{1-6}$alkyl, $C_{1-6}$alkoxy, $C_{1-6}$perfluoroalkyl, $C_{1-6}$perfluoroalkoxy, N-morpholinylcarbonyl, phenyl and benzyl, wherein phenyl or benzyl is optionally substituted with one or more substituents each independently selected from $C_{1-6}$alkyl, $C_{1-6}$perfluoroalkyl, halogen, hydroxy, $C_{1-6}$alkoxy or $C_{1-6}$perfluoroalkoxy;

$R_{12}$ is hydroxymethyl, $C_{1-6}$alkoxymethyl, aminomethyl, mono or di-$C_{1-6}$alkylaminomethyl, —C(O)H, $C_{2-6}$acyloxymethyl, —CN, —CONR$_{13}$R$_{14}$; and

wherein $R_{13}$ and $R_{14}$ are the same or different and are independently selected from hydrogen, $C_{1-6}$alkyl or $C_{1-6}$alkoxy; and $R_{15}$ is hydrogen or $C_{1-6}$alkyl;

or a pharmaceutically acceptable salt thereof.

In a further aspect of this invention various processes used to prepare a variety of compounds of this invention are also disclosed and claimed.

BRIEF DESCRIPTION OF THE DRAWINGS

FIG. 4 is a listing of the sequence, SEQ ID NO:1, a 6.7 kb fragment comprising nucleotides –6635 to +66 of human IL-4 gene promoter.

DETAILED DESCRIPTION OF THE INVENTION

Figure 1:
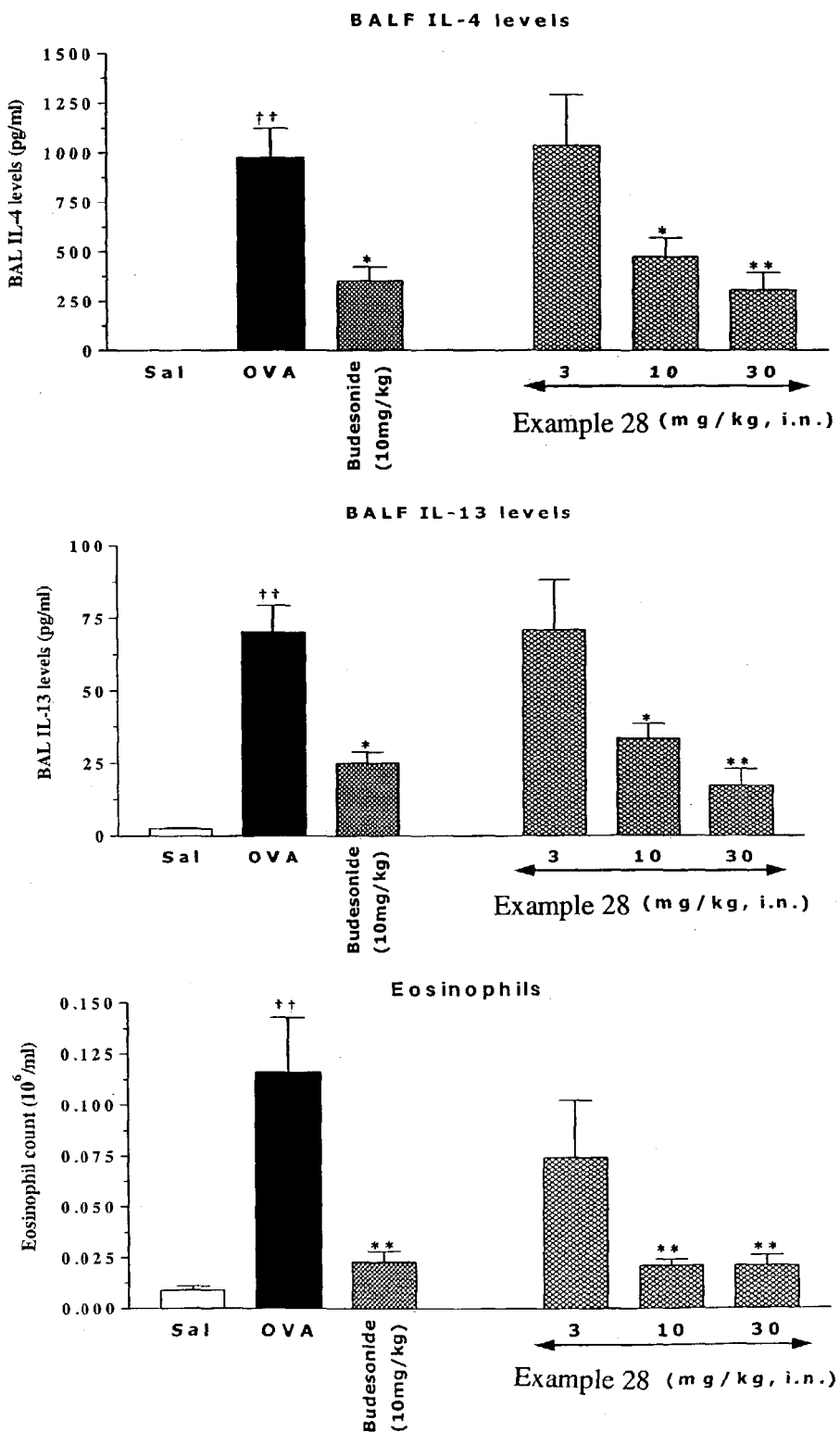
FIG. 1 is a bar graph depicting the effects of 3-(4-pyridinylamino)-1H-indole-2-carboxylic acid (Example 28) on bronchoalveolar lavage fluid (BALF) cytokines and lung inflammation in mice.

The terms as used herein have the following meanings:

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl, n-butyl, isobutyl, tert-butyl, and amyl. Derived expressions such as "$C_{1-6}$alkoxy", "$C_{1-6}$alkoxy$C_{1-6}$alkyl", "hydroxy$C_{1-6}$alkyl", "$C_{1-6}$alkylcarbonyl", "$C_{1-6}$alkoxycarbonyl$C_{1-6}$alkyl", "$C_{1-6}$alkoxycarbonyl", "amino$C_{1-6}$alkyl", "$C_{1-6}$alkylcarbamoyl$C_{1-6}$alkyl", "$C_{1-6}$dialkylcarbamoyl$C_{1-6}$alkyl" "mono- or di-$C_{1-6}$alkylamino$C_{1-6}$alkyl", "amino$C_{1-6}$alkylcarbonyl" "diphenyl$C_{1-6}$alkyl", "phenyl$C_{1-6}$alkyl", "phenylcarboyl$C_{1-6}$alkyl" and "phenoxy$C_{1-6}$alkyl" are to be construed accordingly.

As used herein, the expression "$C_{2-6}$alkenyl" includes ethenyl and straight-chained or branched propenyl, butenyl, pentenyl and hexenyl groups. Similarly, the expression "$C_{2-6}$alkynyl" includes ethynyl and propynyl, and straight-chained or branched butynyl, pentynyl and hexynyl groups.

As used herein, the expression "$C_{1-6}$ perfluoroalkyl" means that all of the hydrogen atoms in said alkyl group are replaced with fluorine atoms. Illustrative examples include trifluoromethyl and pentafluoroethyl, and straight-chained or branched heptafluoropropyl, nonafluorobutyl, undecafluoropentyl and tridecafluorohexyl groups. Derived expression, "$C_{1-6}$ perfluoroalkoxy", is to be construed accordingly.

As used herein, the expression "$C_{3-8}$cycloalkyl" means cyclopropyl, cyclobutyl, cyclopentyl, cyclohexyl, cycloheptyl and cyclooctyl.

As used herein, the expression "$C_{3-8}$cycloalkyl$C_{1-6}$alkyl" means that the $C_{3-8}$cycloalkyl as defined herein is further attached to $C_{1-6}$alkyl as defined herein. Representative examples include cyclopropylmethyl, 1-cyclobutylethyl, 2-cyclopentylpropyl, cyclohexylmethyl, 2-cycloheptylethyl and 2-cyclooctylbutyl and the like.

As used herein the expression "$C_{1-6}$acyl" shall have the same meaning as "$C_{1-6}$alkanoyl", which can also be represented structurally as "R—CO—" group where R is a $C_{2-6}$alkyl as defined herein. Additionally, "$C_{1-6}$alkylcarbonyl" shall mean same as $C_{2-6}$acyl. Specifically, "$C_{1-6}$acyl" shall mean formyl, acetyl or ethanoyl, propanoyl, n-butanoyl, etc. Derived expressions such as "$C_{2-6}$acyloxymethyl" and "$C_{2-6}$acyloxyalkyl" are to be construed accordingly.

"CsA" means cyclosporin A.

"Halogen" or "halo" means chloro, fluoro, bromo, and iodo.

"IL" means interleukin.

"Luc" means luciferase.

As used herein, the various forms of the term "modulation" are intended to include stimulation (e.g., increasing or upregulating a particular response or activity) and inhibition (e.g., decreasing or downregulating a particular response or activity).

As used herein, "patient" means a warm blooded animal, such as for example rat, mice, dogs, cats, guinea pigs, and primates such as humans.

As used herein, the expression "pharmaceutically acceptable carrier" means a non-toxic solvent, dispersant, excipient, adjuvant, or other material which is mixed with the compound of the present invention in order to permit the formation of a pharmaceutical composition, i.e., a dosage form capable of administration to the patient. One example of such a carrier is a pharmaceutically acceptable oil typically used for parenteral administration.

The term "pharmaceutically acceptable salts" as used herein means that the salts of the compounds of the present invention can be used in medicinal preparations. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, hydrobromic acid, sulfuric acid, methanesulfonic acid, 2-hydroxyethanesulfonic acid, p-toluenesulfonic acid, fumaric acid, maleic acid, hydroxymaleic acid, malic acid, ascorbic acid, succinic acid, glutaric acid, acetic acid, salicylic acid, cinnamic acid, 2-phenoxybenzoic acid, hydroxybenzoic acid, phenylacetic acid, benzoic acid, oxalic acid, citric acid, tartaric acid, glycolic acid, lactic acid, pyruvic acid, malonic acid, carbonic acid or phosphoric acid. The acid metal salts such as sodium monohydrogen orthophosphate and potassium hydrogen sulfate can also be formed. Also, the salts so formed may present either as mono- or di-acid salts and can exist either as hydrated or can be substantially anhydrous. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The expression "prodrug" as used herein shall have the generally accepted meaning. In general, as used herein "prodrug" is any compound that undergoes biotransformation before exhibiting its pharmacological effects. As an illustrative example, without any limitation, prodrugs can generally be viewed as drug molecules containing specialized non-toxic protective groups used in a transient manner to alter or to eliminate undesirable properties in the parent molecule. The expression "double prodrug" as used herein shall mean a biologically inactive molecule which is transformed in vivo in two steps (enzymatically and/or chemically) to the active species. The expression "bioprecursor" and/or "bioprecursor prodrug" as used herein shall have the generally accepted meaning. In addition, it shall also mean, without any limitation, that an inactive molecule is transformed to an active molecule by a molecular modification generally through a pathway other than hydrolytic cleavage to form active principle. The expression "analog" as used herein shall have the generally accepted meaning. In addition, it shall also mean, without any limitation, that a drug whose structure is related to that of another drug but whose chemical and biological properties may be quite different.

The expression "stereoisomers" is a general term used for all isomers of the individual molecules that differ only in the orientation of their atoms in space. Typically it includes mirror image isomers that are usually formed due to at least one asymmetric center, (enantiomers). Where the compounds according to the invention possess two or more asymmetric centers, they may additionally exist as diastereoisomers, also certain individual molecules may exist as geometric isomers (cis/trans). It is to be understood that all such isomers and mixtures thereof in any proportion are encompassed within the scope of the present invention.

"Substituted" means substituted by 1 to 2 substituents independently selected from the group consisting of $C_{1-6}$ alkyl, $C_{1-6}$ perfluoroalkyl, hydroxy, —$CO_2H$, an ester, an amide, $C_1$–$C_6$ alkoxy, $C_1$–$C_6$ perfluoroalkoxy, —$NH_2$, Cl, Br, I, F, —NH-lower alkyl, and —N(lower alkyl)$_2$.

"Therapeutically effective amount" means an amount of the compound which is effective in treating the named disorder or condition.

As used in the examples and preparations that follow, the terms used therein shall have the meanings indicated: "kg" refers to kilograms, "g" refers to grams, "mg" refers to milligrams, "μg" refers to micrograms, "pg" refers to picograms, "mol" refers to moles, "mmol" refers to millimoles, "nmole" refers to nanomoles, "L" refers to liters, "mL" or "ml" refers to milliliters, "μL" refers to microliters, "° C." refers to degrees Celsius, "$R_f$" refers to retention factor, "mp" or "m.p." refers to melting point, "dec" refers to decomposition, "bp" or "b.p." refers to boiling point, "mm of Hg" refers to pressure in millimeters of mercury, "cm" refers to centimeters, "nm" refers to nanometers, "$[\alpha]^{20}_D$" refers to specific rotation of the D line of sodium at 20° C. obtained in a 1 decimeter cell, "c" refers to concentration in g/mL, "THF" refers to tetrahydrofuran, "DMF" refers to dimethylformamide, "NMP" refers to 1-methyl-2-pyrrolidinone, "brine" refers to a saturated aqueous sodium chloride solution, "M" refers to molar, "mM" refers to millimolar, "μM" refers to micromolar, "nM" refers to nanomolar, "TLC" refers to thin layer chromatography, "HPLC" refers to high performance liquid chromatography, "HRMS" refers to high resolution mass spectrum, "lb" refers to pounds, "gal" refers to gallons, "L.O.D." refers to loss on drying, "μCi" refers to microcuries, "i.p." refers to intraperitoneally, "i.v." refers to intravenously.

In one aspect of the present invention there is provided a series of compounds which are effective as prodrugs (i.e., $R_2$ is other than hydrogen in the compound of Formula (I) and the definitions that follow). The prodrugs of this invention are generally esters of the active compound. These prodrugs offer one approach to improved drug efficiency. In general, the prodrugs of this invention are converted to the parent active drug (i.e., $R_2$=hydrogen in Formula (I)) in vivo by way of enzymatic hydrolysis (e.g., an esterase converts ester into carboxylic acid, an amidase converts amide into carboxylic acid, etc.). Generally, prodrugs can offer a number of advantages over the parent drugs. For instance, without any limitations, a few of the advantages of the prodrugs of this invention may be enumerated as follows:

1. Enhanced physico-chemical properties, such as for example improved solubility, etc.
2. Improved absorption and distribution under physiological conditions,
3. Site specificity,
4. Stability,
5. Prolonged release,
6. Low toxicity when compared with parent active molecule,
7. Patient acceptability, and
8. Improved formulation properties.

The compounds of this invention are generally carboxylic acids and ester derivatives of 3-(4-pridinylamino)-1H-indole-2-caroxylic acid (Example 28). The free acid, 3-(4-pridinylamino)-1H-indole-2-caroxylic acid, generally, features relatively low solubility and low oral bioavailability. The ester prodrugs derived therefrom on the other hand exhibit enhanced solubility as well as improved bioavailability, especially when administered orally. The compounds of this invention, which include ester prodrugs and analogs, are represented by the following formula (I):

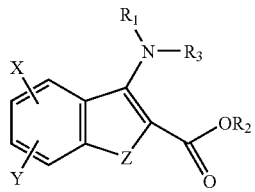

wherein

X and Y are the same or different and are independently selected from the group consisting of hydrogen, halogen, nitro, amino, hydroxy, $C_{1-6}$alkyl, $C_{2-6}$alkenyl, $C_{2-6}$alkynyl, $C_{1-6}$alkoxy, $C_{1-6}$perfluoroalkyl, $C_{1-6}$perfluoroalkoxy, phenyl and benzyl, wherein phenyl or benzyl is optionally substituted with one or two substituents each independently selected from $C_{1-6}$alkyl, $C_{1-6}$perfluoroalkyl, halogen, hydroxy or $C_{1-6}$perfluoroalkyl or $C_{1-6}$perfluoroalkoxy;

Z is N—R or S, wherein R is selected from the group consisting of hydrogen, $C_{1-6}$alkyl, $C_{1-6}$alkylcarbonyl, $C_{1-6}$alkoxycarbonyl$C_{1-6}$alkyl, $C_{1-6}$alkylcarbamoyl-$C_{1-6}$alkyl and $C_{1-6}$dialkylcarbamoyl$C_{1-6}$alkyl;

$R_1$ is selected from the group consisting of hydrogen, $C_{1-6}$alkyl, $C_{2-6}$alkenyl, $C_{2-6}$alkynyl, $C_{1-6}$perfluoroalkyl, $C_{3-8}$cycloalkyl, $C_{3-8}$cycloalkyl$C_{1-6}$alkyl, $C_{1-6}$alkoxy$C_{1-6}$alkyl, hydroxy$C_{1-6}$alkyl, amino$C_{1-6}$alkyl, mono- or di-$C_{1-6}$alkyl-amino$C_{1-6}$alkyl, formyl, $C_{1-6}$alkylcarbonyl, amino$C_{1-6}$alkylcarbonyl, $C_{1-6}$alkoxycarbonyl, phenyl, diphenyl$C_{1-6}$alkyl and phenyl$C_{1-6}$alkyl, phenylcarbonyl$C_{1-6}$alkyl, phenoxy$C_{1-6}$alkyl, wherein phenyl is optionally substituted with one or two substituents each independently selected from $C_{1-6}$alkyl, $C_{1-6}$perfluoroalkyl, halogen, hydroxy or $C_{1-6}$perfluoroalkyl or $C_{1-6}$perfluoroalkoxy;

$R_3$ is

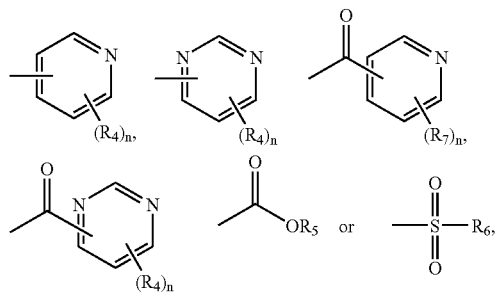

wherein $R_4$ is selected form the group consisting of hydrogen, halogen, nitro, amino, hydroxy, $C_{1-6}$alkyl, $C_{1-6}$alkoxy, $C_{1-6}$perfluoroalkyl, $C_{1-6}$perfluoroalkoxy, N-morpholinylcarbonyl, phenyl and benzyl, wherein phenyl or benzyl is optionally substituted with one or two substituents each independently selected from $C_{1-6}$alkyl, $C_{1-6}$perfluoroalkyl, halogen, hydroxy or $C_{1-6}$alkoxy or $C_{1-6}$perfluoroalkoxy;

$R_5$ is selected from the group consisting of $C_{2-8}$alkyl, $C_{3-8}$cycloalkyl, $C_{2-6}$alkenyl, $C_{2-6}$alkynyl, pyridyl, phenyl, styryl, benzyl, diazophenyl, naphthyl and quinolinyl, wherein cycloalkyl, pyridyl, phenyl, styryl, benzyl, diazophenyl, naphthyl or quinolinyl is optionally substituted with one or more substituents each independently selected from $C_{1-6}$alkyl, $C_{1-6}$perfluoroalkyl, nitro, amino, dimethylamino, acetamido, halogen, hydroxy, $C_{1-6}$alkoxy or $C_{1-6}$perfluoroalkoxy;

$R_6$ is selected from the group consisting of $C_{6-12}$bicycloalkyl, styryl, thiazolyl, diazophenyl, naphthyl and quinolinyl, wherein bicycloalkyl, styryl, thiazolyl, diazophenyl, naphthyl or quinolinyl is optionally substituted with one or more substituents each independently selected from $C_{1-6}$alkyl, $C_{1-6}$perfluoroalkyl, nitro, amino, dimethylamino, acetamido, halogen, hydroxy, $C_{1-6}$alkoxy or $C_{1-6}$perfluoroalkoxy;

$R_7$ is selected from the group consisting of halogen, nitro, amino, hydroxy, $C_{1-6}$alkyl, $C_{1-6}$alkoxy, $C_{1-6}$perfluoroalkyl, $C_{1-6}$perfluoroalkoxy, N-morpholinylcarbonyl, phenyl and benzyl, wherein phenyl or benzyl is optionally substituted with one or two substituents each independently selected from $C_{1-6}$alkyl, $C_{1-6}$perfluoroalkyl, halogen, hydroxy, $C_{1-6}$alkoxy or $C_{1-6}$perfluoroalkoxy; and n is an integer from 0 to 3; and $R_2$ is selected from the group consisting of hydrogen, $C_{1-6}$alkyl, $C_{1-6}$perfluoroalkyl, perfluoroaryl, indanyl, $C_{1-6}$alkoxy$C_{1-6}$alkyl, $C_{2-6}$acyloxy$C_{1-6}$alkyl, $C_{1-6}$alkoxycarbonyl$C_{1-6}$alkyl, $C_{1-6}$alkoxycarbonyloxy$C_{1-6}$alkyl, $C_{3-8}$cycloalkyl, $C_{3-8}$cycloalkoxycarbonyloxy-$C_{1-6}$alkyl, adamantyloxycarbonyloxy$C_{1-6}$alkyl, $C_{3-8}$cycloalkoxycarbonyl-$C_{1-6}$alkyl, mono- or di-$C_{1-6}$alkylamino-$C_{1-6}$alkyl, $C_{3-8}$azacycloalkyl$C_{1-6}$alkyl, mono- or di-$C_{1-6}$alkylcarbamoyl-$C_{1-6}$alkyl, $C_{3-8}$azacycloalkylcarbonyloxy$C_{1-6}$alkyl, benzyl$C_{1-6}$alkylcarbamoyl$C_{1-6}$alkyl, mono- or di-$C_{1-6}$alkylcarbamoyloxy$C_{1-6}$alkyl, $C_{3-8}$azacycloalkylcarbonyloxy-$C_{1-6}$alkyl, benzyl$C_{1-6}$alkylcarbamoyloxy-$C_{1-6}$alkyl, benzylcarbamoyloxy$C_{1-6}$alkyl, $C_{1-6}$alkoxycarbonylamino-oxo-$C_{1-6}$alkyl,

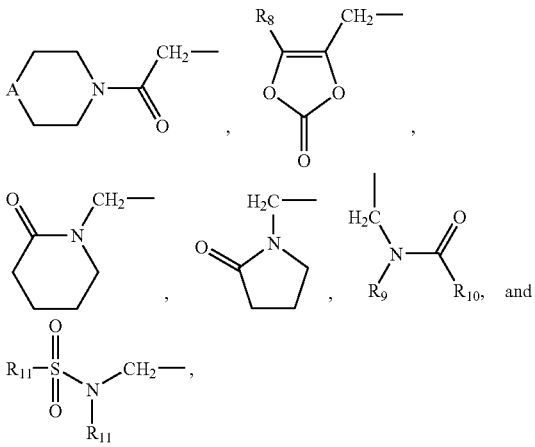

wherein $R_8$ is hydrogen or $C_{1-6}$alkyl, $R_9$ is $C_{1-6}$alkyl or phenyl, $R_{10}$ is hydrogen, $C_{1-6}$alkyl or $C_{1-6}$alkoxycarbonyl$C_{1-6}$alkyl, $R_{11}$ is $C_{1-6}$alkyl, phenyl or tolyl, and A is $CH_2$, NH or O, or a pharmaceutically acceptable salt thereof, with the proviso that when Z is N—R, and when both X and Y are hydrogen, $R_2$ is not hydrogen or $C_{1-6}$alkyl.

As noted above, a few of the compounds encompassed by the above noted generic formula (I) are known in the literature. In particular, the free carboxylic acid and alkyl esters of 3-(4-pyridinylamino)-1H-indole 2-carboxylic acid of formula (IA):

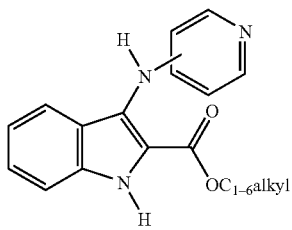

(IA)

are known in the literature. See U.S. Pat. Nos. 5,177,088 and 5,328,920.

In a preferred embodiment of this invention the compounds having the following moieties are preferred:

X and Y are the same or different and are independently selected from the group consisting of halogen, amino, hydroxy, $C_{1-6}$alkoxy, $C_{1-6}$perfluoroalkoxy and phenyl, wherein phenyl is optionally substituted with one or two substituents each independently selected from $C_{1-6}$alkyl, $C_{1-6}$perfluoroalkyl, halogen, hydroxy, $C_{1-6}$perfluoroalkyl or $C_{1-6}$perfluoroalkoxy;

Z is N—R, wherein R is selected from the group consisting of hydrogen, $C_{1-6}$alkyl and $C_{1-6}$alkylcarbonyl;

$R_1$ is hydrogen;

$R_3$ is

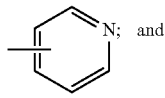

$R_2$ is $C_{1-6}$alkyl or a pharmaceutically acceptable salt thereof.

Specific compounds belonging to this preferred embodiment include 5,6-dimethoxy-3-(4-pyridinylamino)-1H-indole-2-carboxylic acid, ethyl ester.

In yet another embodiment of this invention the prodrugs encompassed by the above noted generic structure (I), wherein Z is N—R, and wherein R is hydrogen, $C_{1-6}$alkyl or $C_{1-6}$alkylcarbonyl are preferred.

In this aspect of the embodiment, preferred are the compounds wherein X is hydrogen or halogen; Y is phenyl, and wherein phenyl is optionally substituted with one or two substituents each independently selected from $C_{1-6}$alkyl, $C_{1-6}$perfluoroalkyl, halogen, hydroxy or $C_{1-6}$perfluoroalkoxy; R is hydrogen or $C_{1-6}$alkyl; $R_1$ is hydrogen;

$R_3$ is

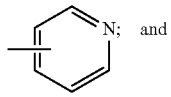

$R_2$ is $C_{1-6}$alkyl or a pharmaceutically acceptable salt thereof.

Specific compounds encompassed by this embodiment include 6-phenyl-3-(4-pyridinylamino)-1H-indole-2-carboxylic acid, ethyl ester.

In yet another embodiment, the compounds of this invention having the formula (I) wherein X, Y and R are hydrogen are preferred. In this embodiment, preferred are the compounds wherein:

$R_1$ is hydrogen;

$R_3$ is

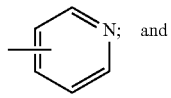

$R_2$ is $C_{1-6}$perfluoroalkyl, perfluoroaryl, indanyl, $C_{1-6}$alkoxy$C_{1-6}$alkyl, $C_{2-6}$acyloxy$C_{1-6}$alkyl, $C_{1-6}$alkoxycarbonyl$C_{1-6}$alkyl, $C_{1-6}$alkoxycarbonyloxy$C_{1-6}$alkyl, $C_{3-8}$cycloalkyl, $C_{3-8}$cycloalkoxycarbonyloxy-$C_{1-6}$alkyl, adamantyloxycarbonyloxy$C_{1-6}$alkyl, $C_{3-8}$cycloalkoxycarbonyl-$C_{1-6}$alkyl, mono- or di-$C_{1-6}$alkylamino-$C_{1-6}$alkyl, $C_{3-8}$azacycloalkyl$C_{1-6}$alkyl, mono- or di-$C_{1-6}$alkylcarbamoyl-$C_{1-6}$alkyl, $C_{3-8}$azacycloalkylcarbonyloxy$C_{1-6}$alkyl, benzyl$C_{1-6}$alkylcarbamoyl$C_{1-6}$alkyl, mono- or di-$C_{1-6}$alkylcarbamoyloxy$C_{1-6}$alkyl, $C_{3-8}$azacycloalkylcarbonyloxy-$C_{1-6}$alkyl, benzyl$C_{1-6}$alkylcarbamoyloxy-$C_{1-6}$alkyl, benzylcarbamoyloxy$C_{1-6}$alkyl, $C_{1-6}$alkoxycarbonylamino-oxo-$C_{1-6}$alkyl,

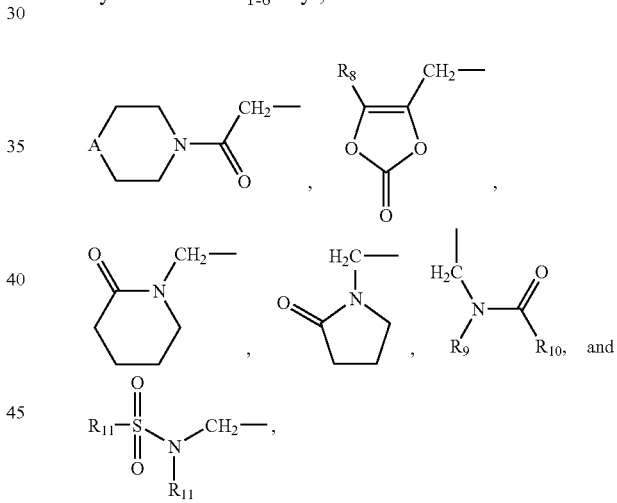

wherein $R_8$ is hydrogen or $C_{1-6}$alkyl, $R_9$ is $C_{1-6}$alkyl or phenyl, $R_{10}$ is hydrogen, $C_{1-6}$alkyl or $C_{1-6}$alkoxycarbonyl$C_{1-6}$alkyl, $R_{11}$ is $C_{1-6}$alkyl, phenyl or tolyl, and A is $CH_2$, NH or O.

Representative compounds encompassed by this embodiment may be enumerated as follows:

3-(4-pyridinylamino)-1H-indole-2-carboxylic acid pentafluorophenyl ester, 3-(4-pyridinylamino)-1H-indole-2-carboxylic acid 2-diethylaamino-ethyl ester, 3-(4-pyridinylamino)-1H-indole-2-carboxylic acid 2-dimethylamino-ethyl ester, 3-(4-pyridinylamino)-1H-indole-2-carboxylic acid 2-piperidin-1-yl-ethyl ester, 3-(pyridin-4-ylamino)-1H-indole-2-carboxylic acid (S)-1-methoxycarbonyl-ethyl ester,
3-(pyridin-4-ylamino)-1H-indole-2-carboxylic acid ethoxycarbonylmethyl ester,
3-(4-pyridinylamino)-1H-indole-2-carboxylic acid 2-methoxyethyl ester,
3-(4-pyridinylamino)-1H-indole-2-carboxylic acid 3-ethoxypropyl ester,
3-(pyridin-4-ylamino)-1H-indole-2-carboxylic acid indan-5-yl ester,
3-(pyridin-4-ylamino)-1H-indole-2-carboxylic acid diethylcarbamoylmethyl ester,
3-(pyridin-4-ylamino)-1H-indole-2-carboxylic acid 2-morpholin-4-yl-2-oxo-ethyl ester,
3-(pyridin-4-ylamino)-1H-indole-2-carboxylic acid 2-oxo-2-pyrrolidin-1-yl-ethyl ester,
3-(pyridin-4-ylamino)-1H-indole-2-carboxylic acid 2-azetidin-1-yl-2-oxo-ethyl ester,
3-(pyridin-4-ylamino)-1H-indole-2-carboxylic acid (benzyl-ethyl-carbamoyl)-methyl ester,
3-(pyridin-4-ylamino)-1H-indole-2-carboxylic acid diethyl-carbamoyloxy-methyl ester,
3-(pyridin-4-ylamino)-1H-indole-2-carboxylic acid bezyl-carbamoyloxymethyl ester,
3-(pyridin-4-ylamino)-1H-indole-2-carboxylic acid piperidine-1-carbonyloxymethyl ester,
3-(pyridin-4-ylamino)-1H-indole-2-carboxylic acid morpholine-4-carbonyloxymethyl ester,
3-(pyridin-4-ylamino)-1H-indole-2-carboxylic acid 2-ethoxycarbonylamino-2-oxy-ethyl ester,
3-(pyridin-4-ylamino)-1H-indole-2-carboxylic acid iso-propoxycarbonyloxy-methyl ester,
3-(pyridin-4-ylamino)-1H-indole-2-carboxylic acid 1,1,2-trimethylpropoxy-carbonyloxy-methyl ester,
3-(pyridin-4-ylamino)-1H-indole-2-carboxylic acid cyclohexyloxy-carbonyloxy-methyl ester,
3-(pyridin-4-ylamino)-1H-indole-2-carboxylic acid adamantan-1-yloxycarbonyloxymethyl ester,
3-(pyridin-4-ylamino)-1H-indole-2-carboxylic acid acetoxymethyl ester,
3-(pyridin-4-ylamino)-1H-indole-2-carboxylic acid 2,2-dimethyl-propionyloxymethyl ester,
3-(pyridin-4-ylamino)-1H-indole-2-carboxylic acid pentanoyloxymethyl ester,
3-(pyridin-4-ylamino)-1H-indole-2-carboxylic acid 2-oxo-piperidin-1-ylmethyl ester,
3-(pyridin-4-ylamino)-1H-indole-2-carboxylic acid (benzoyl-ethoxycarbonylmethyl-amino)-methyl ester,
3-(pyridin-4-ylamino)-1H-indole-2-carboxylic acid 2-oxo-pyrrolidin-1-ylmethyl ester,
3-(pyridin-4-ylamino)-1H-indole-2-carboxylic acid 5-methyl-2-oxo-(1,3)dioxo-4-ylmethyl ester,
3-(pyridin-4-ylamino)-1H-indole-2-carboxylic acid (phenyl-(toulene-4-sulfonyl)-amino)-methyl ester,
3-(pyridin-4-ylamino)-1H-indole-2-carboxylic acid (benzenesulfonyl-methyl-amino)-methyl ester,
3-(pyridin-4-ylamino)-1H-indole-2-carboxylic acid (methyl-(toulene-4-sulfonyl)-amino)-methyl ester, and
3-(pyridin-4-ylamino)-1H-indole-2-carboxylic acid tert-butoxycarbonyloxy-methyl ester.

In a further embodiment of this invention, preferred compounds of this invention are those wherein $R_3$ is

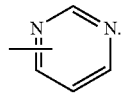

A specific compound of this embodiment includes 3-(pyrimidin-2-ylamino)-1H-indole-2-carboxylic acid, ethyl ester.

In yet another embodiment of this invention, a few of the compounds encompassed by the generic structure (I) are analogs of the active compound. In this embodiment, specific examples of compounds are those wherein $R_3$ is

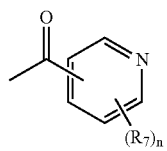

and wherein $R_7$ is chloro, methyl, methoxy or N-morpholinylcarbonyl, and n is 1 or 2.

Representative examples of compounds falling within the scope of this embodiment include the following:
3-(2-chloro-pyridine-4-carbonyl)-amino-3H-indole-2-carboxylic acid ethyl ester,
3-(2,6-dichloro-pyridine-4-carbonyl)-amino-3H-indole-2-carboxylic acid ethyl ester,
3-(2-chloro-6-methyl-pyridine-4-carbonyl)-amino-3H-indole-2-carboxylic acid ethyl ester,
3-(2-chloro-6-methoxy-pyridine-4-carbonyl)-amino-3H-indole-2-carboxylic acid ethyl ester,
3-(2-chloro-pyridine-4-carbonyl)-amino-3H-indole-2-carboxylic acid tert-butyl ester,
3-(2,6-dichloro-pyridine-4-carbonyl)-amino-3H-indole-2-carboxylic acid tert-butyl ester,
3-(2-chloro-6-methoxy-pyridine-4-carbonyl)-amino-3H-indole-2-carboxylic acid tert-butyl ester, and
3-{[6-(morpholine-4-carbonyl)-pyridine-3-carbonyl]-amino}-3H-indole-2-carboxylic acid ethyl ester.

In another embodiment, further examples of analogs of the active compound are enumerated. In this embodiment, specific types of compounds included are those wherein $R_3$ is

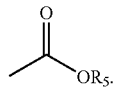

Representative examples of compounds belonging to this embodiment are enumerated as follows:
3-(1-ethyl-pentyloxycarbonylamino)-3H-indole-2-carboxylic acid tert-butyl ester,
3-n-hexyloxycarbonylamino-3H-indole-2-carboxylic acid tert-butyl ester,
3-(2,2-dimethyl-propoxycarbonylamino)-3H-indole-2-carboxylic acid tert-butyl ester, 3-tert-butoxycarbonylamino-3H-indole-2-carboxylic acid tert-butyl ester,
3-n-butoxycarbonylamino-3H-indole-2-carboxylic acid tert-butyl ester,
3-n-propoxycarbonylamino-3H-indole-2-carboxylic acid tert-butyl ester,
3-ethoxycarbonylamino-3H-indole-2-carboxylic acid tert-butyl ester,
3-allyloxycarbonylamino-3H-indole-2-carboxylic acid tert-butyl ester,
3-but-3-enyloxycarbonylamino-3H-indole-2-carboxylic acid tert-butyl ester,
3-prop-2-ynyloxycarbonylamino-3H-indole-2-carboxylic acid tert-butyl ester,
3-((R)-2-tert-butyl-(S)-5-methyl-cyclohexyloxycarbonylamino)-3H-indole-2-carboxylic acid tert-butyl ester,
3-((S)-2-tert-butyl-(R)-5-methyl-cyclohexyloxycarbonylamino)-3H-indole-2-carboxylic acid tert-butyl ester,
3-(4-nitro-phenoxycarbonylamino)-3H-indole-2-carboxylic acid tert-butyl ester,
3-(4-methoxy-phenoxycarbonylamino)-3H-indole-2-carboxylic acid tert-butyl ester,
3-(4-bromo-phenoxycarbonylamino)-3H-indole-2-carboxylic acid tert-butyl ester,
3-(4-fluoro-phenoxycarbonylamino)-3H-indole-2-carboxylic acid tert-butyl ester,
3-(4-methyl-phenoxycarbonylamino)-3H-indole-2-carboxylic acid tert-butyl ester,
3-(4-chloro-phenoxycarbonylamino)-3H-indole-2-carboxylic acid tert-butyl ester,
3-(2-nitro-phenoxycarbonylamino)-3H-indole-2-carboxylic acid tert-butyl ester, and
3-(2-nitro-3,4-dimethoxy-phenoxycarbonylamino)-3H-indole-2-carboxylic acid tert-butyl ester, In yet another embodiment exemplification of analogs of the active compound may be made wherein
$R_3$ is

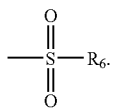

Specific examples within the scope of this invention include the following:
3-(2-phenyl-ethenesulfonylamino)-3H-indole-2-carboxylic acid tert-butyl ester,
3-[4-(4-dimethylamino-phenylazo)-benzenesulfonylamino]-3H-indole-2-carboxylic acid tert-butyl ester,
3-(naphthalene-1-sulfonylamino)-3H-indole-2-carboxylic acid tert-butyl ester,
3-(5-dimethylamino-naphthalene-1-sulfonylamino)-3H-indole-2-carboxylic acid tert-butyl ester,
3-(7,7-dimethyl-3-oxo-bicyclo[2.2.1]hept-2-ylmethanesulfonylamino)-3H-indole-2-carboxylic acid tert-butyl ester,
3-(2-acetylamino-thiazole-5-sulfonylamino)-3H-indole-2-carboxylic acid tert-butyl ester,
3-(quinoline-8-sulfonylamino)-3H-indole-2-carboxylic acid tert-butyl ester,
3-(2-phenyl-ethenesulfonylamino)-3H-indole-2-carboxylic acid,
3-[4-(4-dimethylamino-phenylazo)-benzenesulfonylamino]-3H-indole-2-carboxylic acid,
3-(naphthalene-1-sulfonylamino)-3H-indole-2-carboxylic acid,
3-(5-dimethylamino-naphthalene-1-sulfonylamino)-3H-indole-2-carboxylic acid,
3-(7,7-dimethyl-3-oxo-bicyclo[2.2.1]hept-2-ylmethanesulfonylamino)-3H-indole-2-carboxylic acid,
3-(2-acetylamino-thiazole-5-sulfonylamino)-3H-indole-2-carboxylic acid, and
3-(quinoline-8-sulfonylamino)-3H-indole-2-carboxylic acid.

In a further embodiment of this invention, a compound of formula (I) wherein Z is S is also preferred. Representative examples of this embodiment include the following:
3-(4-pyridinylamino)-bezo(b)thiophene-2-carboxylic acid ethyl ester,
6-fluoro-3-(4-pyridinylamino)-bezo(b)thiophene-2-carboxylic acid ethyl ester,
ethyl 3-((4-pyridyl)amino-N-methyl)-bezo(b)thiophenyl-2-carboxylate,
3-(4-pyridinylamino)-6-trifluoromethyl-bezo(b)thiophene-2-carboxylic acid methane sulfonate salt,
3-(4-pyridinylamino)-bezo(b)thiophene-2-carboxylic acid hydrochloride salt,
3-(4-pyridinylamino)-6-trifluoromethyl-bezo(b)thiophene-2-carboxylic acid ethyl ester hydrochloride salt, and
3-(propyl-4-pyridinylamino)-bezo(b)thiophene-2-carboxylic acid ethyl ester.

In another aspect of this invention there is also provided bioprecursors of the active compound. As noted earlier, the expression "bioprecursor" as used herein shall have the generally accepted meaning. In addition, "bioprecursor" as used herein shall also mean that it is converted to parent active compound by means other than hydrolytic pathway. For instance, bioprecursors of this invention may convert to active compound under physiological conditions by means of enzymatic oxidations. Examples of such enzymatic oxidations include monoamine oxidase or oxidations involving cytochrome P450. The bioprecursor compounds of this invention may be represented by the following formula (II):

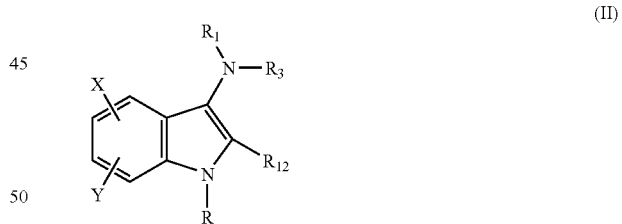

wherein
X and Y are the same or different and are independently selected from the group consisting of hydrogen, halogen, nitro, amino, hydroxy, $C_{1-6}$alkyl, $C_{2-6}$alkenyl, $C_{2-6}$alkynyl, $C_{1-6}$alkoxy, $C_{1-6}$perfluoroalkyl, $C_{1-6}$perfluoroalkoxy, phenyl and benzyl, wherein phenyl or benzyl is optionally substituted with one or two substituents each independently selected from $C_{1-6}$alkyl, $C_{1-6}$perfluoroalkyl, halogen, hydroxy or $C_{1-6}$perfluoroalkyl or $C_{1-6}$perfluoroalkoxy;
R is selected from the group consisting of hydrogen, $C_{1-6}$alkyl, $C_{1-6}$alkylcarbonyl, $C_{1-6}$alkoxycarbonyl$C_{1-6}$alkyl, $C_{1-6}$alkylcarbamoyl-$C_{1-6}$alkyl and $C_{1-6}$dialkylcarbamoyl$C_{1-6}$alkyl;

$R_1$ is selected from the group consisting of hydrogen, $C_{1-6}$alkyl, $C_{2-6}$alkenyl, $C_{2-6}$alkynyl, $C_{1-6}$perfluoroalkyl, $C_{3-8}$cycloalkyl, $C_{3-8}$cycloalkyl$C_{1-6}$alkyl, $C_{1-6}$alkoxy$C_{1-6}$alkyl, hydroxy$C_{1-6}$alkyl, amino$C_{1-6}$alkyl, mono- or di-$C_{1-6}$alkyl-amino$C_{1-6}$alkyl, formyl, $C_{1-6}$alkylcarbonyl, amino$C_{1-6}$alkylcarbonyl, $C_{1-6}$alkoxycarbonyl, phenyl, diphenyl$C_{1-6}$alkyl and phenyl$C_{1-6}$alkyl, phenylcarbonyl$C_{1-6}$alkyl, phenoxy$C_{1-6}$alkyl, wherein phenyl is optionally substituted with one, or two substituents each independently selected from $C_{1-6}$alkyl, $C_{1-6}$perfluoroalkyl, halogen, hydroxy or $C_{1-6}$perfluoroalkyl or $C_{1-6}$perfluoroalkoxy;

$R_3$ is

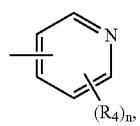

wherein
$R_4$ is selected form the group consisting of hydrogen, halogen, nitro, amino, hydroxy, $C_{1-6}$alkyl, $C_{1-6}$alkoxy, $C_{1-6}$perfluoroalkyl, $C_{1-6}$perfluoroalkoxy, N-morpholinylcarbonyl, phenyl and benzyl, wherein phenyl or benzyl is optionally substituted with one or more substituents each independently selected from $C_{1-6}$alkyl, $C_{1-6}$perfluoroalkyl, halogen, hydroxy, $C_{1-6}$alkoxy or $C_{1-6}$perfluoroalkoxy;

$R_{12}$ is hydroxymethyl, $C_{1-6}$alkoxymethyl, aminomethyl, mono or di-$C_{1-6}$alkylaminomethyl, —C(O)H, $C_{2-6}$acyloxymethyl, —CONR$_{13}$R$_{14}$; and

wherein $R_{13}$ and $R_{14}$ are the same or different and are independently selected from
hydrogen, $C_{1-6}$alkyl or $C_{1-6}$alkoxy; and
$R_{15}$ is hydrogen or $C_{1-6}$alkyl;
or a pharmaceutically acceptable salt thereof.

Representative examples of bioprecursors of this invention, without limitation, include the following:
3-(pyridin-4-ylamino)-1H-indole-2-carboxylic acid methoxy-methyl-amide,
3-(pyridin-4-ylamino)-1H-indole-2-carboxaldehyde,
[3-(pyridin-4-ylamino)-1H-indol-2-yl]-methanol,
3-(pyridin-4-ylamino)-1H-indole-2-carboxamide, and
(2-aminomethyl-1H-indol-3-yl)-pyridin-4-yl-amine.

As noted above, a few of the compounds encompassed by the generic formula (I) of this invention are known compounds (e.g. Formula IA). In general, the compounds of this invention can be readily synthesized by any of the procedures known to one skilled in the art. Specifically, the known compounds used in the method of this invention can be made in accordance with the procedures set forth in U.S. Pat. Nos. 5,177,088; 5,189,054; 5,328,920; 5,491,153; and 5,675,018. Each of these patents is herein incorporated by reference in its entirety.

More specifically, the compounds disclosed herein can be synthesized according to the following procedures of Schemes A–H, wherein the X, Y, Z, $R_1$, $R_2$ and $R_3$ substituents are as defined for Formula (I) above unless otherwise indicated.

In general, for the indole derivatives used in the method of this invention, the starting 3-aminoindole can be prepared following the procedures shown in Scheme A–D.

Scheme A

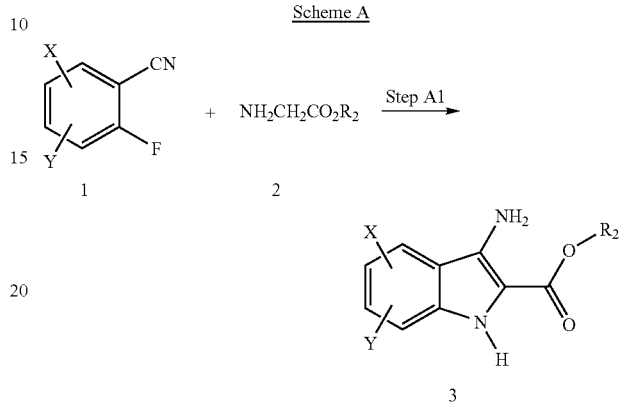

In scheme A, in step A1, the substituted 2-fluorobenzonitirile, 1 is reacted with α-aminocarboxylic acid ester, 2 to form the 3-aminoindole derivative, 3. The reaction is generally carried out neat or in the presence of a suitable organic solvent under basic reaction conditions. Suitable base includes, alkaline hydroxides such as sodium or potassium hydroxide, alkaline carbonates such as sodium or potassium carbonate, ammonia or ammonium hydroxide and the like. The reaction is generally carried out at ambient or elevated temperatures in the range of from about 80° C. to 150° C. in an inert atmosphere such as nitrogen or argon.

Scheme B

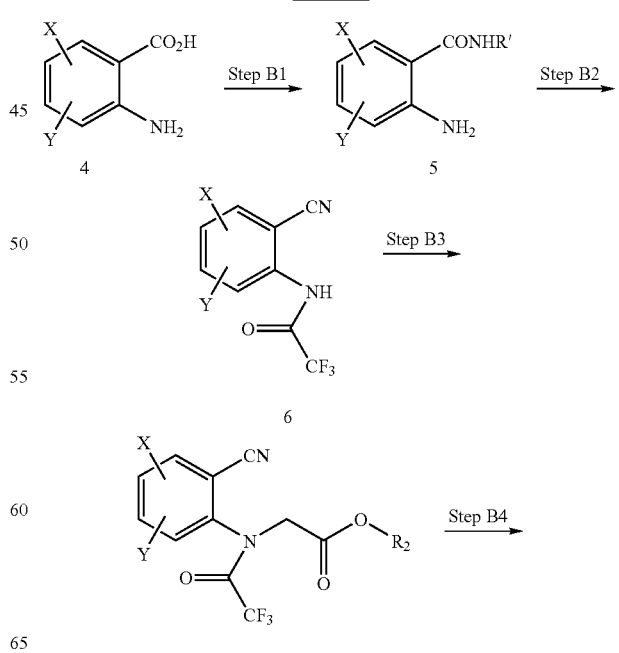

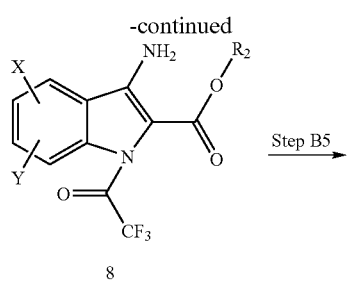

Scheme B shows another approach to the synthesis of 3-aminoindole derivatives, 3 involving 5 steps starting from the substituted 2-aminobenzoic acid, 4. In this approach, the carboxylic acid group is first converted to the nitrile group in steps B1 and B2. Any of the procedures known in the art to facilitate such conversion can be employed. Thus, for example, in step B1 of Scheme B, the substituted 2-aminobenzoic acid, 4 is treated with activating moieties such as N-hydroxysuccinimide in the presence of a suitable dehydrating agent in a suitable organic solvent. The activated carboxylic acid derivative is then reacted with an amine such as for example tert-butyl amine to form the benzamide derivative, 5. Suitable dehydrating agents include dicyclohexylcarbodiimide, cyanuric chloride, and the like. The reaction can be carried out at ambient or sub-ambient temperatures, for example, −20° C. to 25° C.

In step B2, Scheme B, the benzamide, 5 formed in step B1 is further reacted to form the benzonitrile derivative, 6. In general, this can be affected by reacting the benzamide, 5 with a suitable carboxylic acid anhydride such as trifluoroacetic anhydride to form the benzonitrile derivative, 6. The reaction in this step can be carried out in a suitable organic solvent such as dichloromethane at ambient to sub-ambient reaction temperatures, preferably at around 0° C.

In step B3, Scheme B, the benzonitrile derivative, 6 is further reacted with a desired α-halocarboxylic acid ester, 7 in the presence of a suitable base in an organic solvent such as DMF. Suitable bases include alkali hydrides such as sodium hydride or alkyl-alkali compounds such as butyl lithium and the like. The reaction is generally carried out in inert atmospheres, such as nitrogen or argon, and at sub-ambient temperatures, such as for example 0° C. however, ambient to super-ambient reaction temperatures can also be utilized.

In step B4, Scheme B, the addition product, 8 from step B3 is cyclyzed in the presence of a base under inert reaction conditions typically at sub-ambient temperatures such as 0° C. Any of the base that is effective to carry out this cyclization reaction can be employed and such examples include alkaline hydroxides such as sodium or potassium hydroxide, alkaline carbonates such as sodium or potassium carbonate, alkaline alkoxides such as potassium tert-butoxide, ammonia or ammonium hydroxide and the like. Potassium tert-butoxide is particularly preferred.

Finally, in step B5, Scheme B, the starting indole compound, 3 is prepared by cleaving off the trifluoroacetyl group on the amino group of the indole compound, 8. This cleavage can be effected using any of the methods known in the art. For example, the cleavage can be effected by treating the product, 8 from B4 with a base such as potassium carbonate at ambient or super-ambient reaction temperatures; temperature in the range of 50 to 80° C. is particularly preferred.

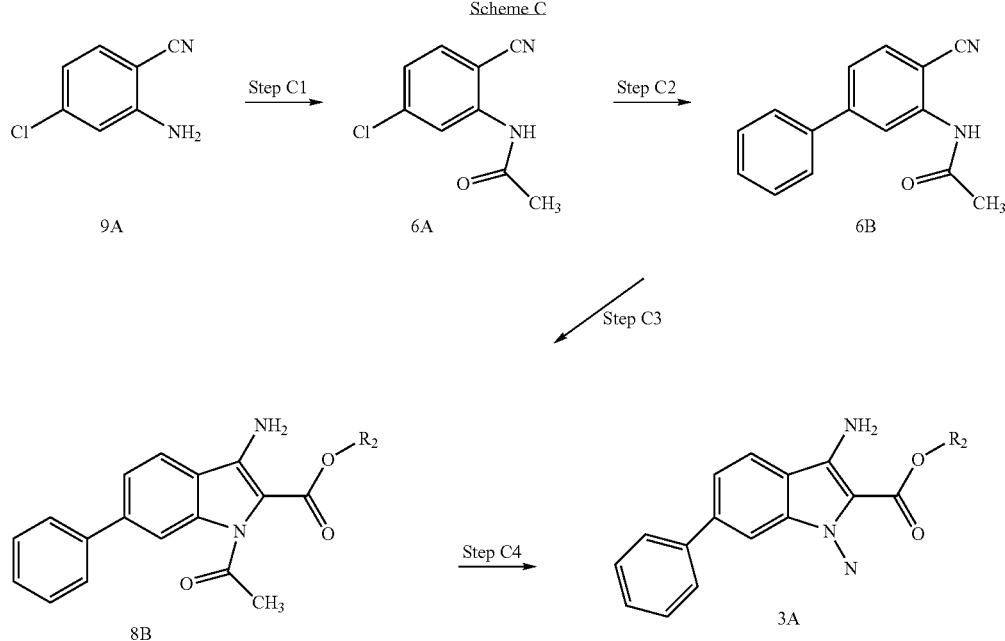

Scheme C illustrates a synthesis of particularly one type of substituted 3-amino-indole derivative, 3A in which the substituent on the indole ring is phenyl. Various other mono or diaryl substituted 3-amino-indole derivatives can be synthesized following the steps of Scheme C. In step C1, Scheme C the amino group of the 2-amino-4-chloro-benzonitrile, 9A is protected by acetyl group by treating with acetic anhydride. Various other protective groups can be employed in a similar fashion. In step C2, scheme C, the protected amino compound, 6A is phenylated using a phenylating agent such as phenylboronic acid in the presence of a transition metal catalyst such as palladium acetate. In step C3, Scheme C the phenylated compound, 6B is reacted with α-halo-carboxylic acid ester using the procedures similar to the ones described for steps B3 and B4 of Scheme B. Interestingly, in this step both addition and cyclization can be carried out in a single step to form the indole derivative, 8B. This combination of reactions can typically be effected in the presence of a suitable base such as potassium tert-butoxide. The reaction is typically carried out in an organic solvent such as NMP, THF or mixtures thereof at temperatures in the range of from about 0° C. to 40° C. Finally, in step C4, Scheme C the acetyl indole derivative, 8B is deprotected following the procedures of step B5, Scheme B.

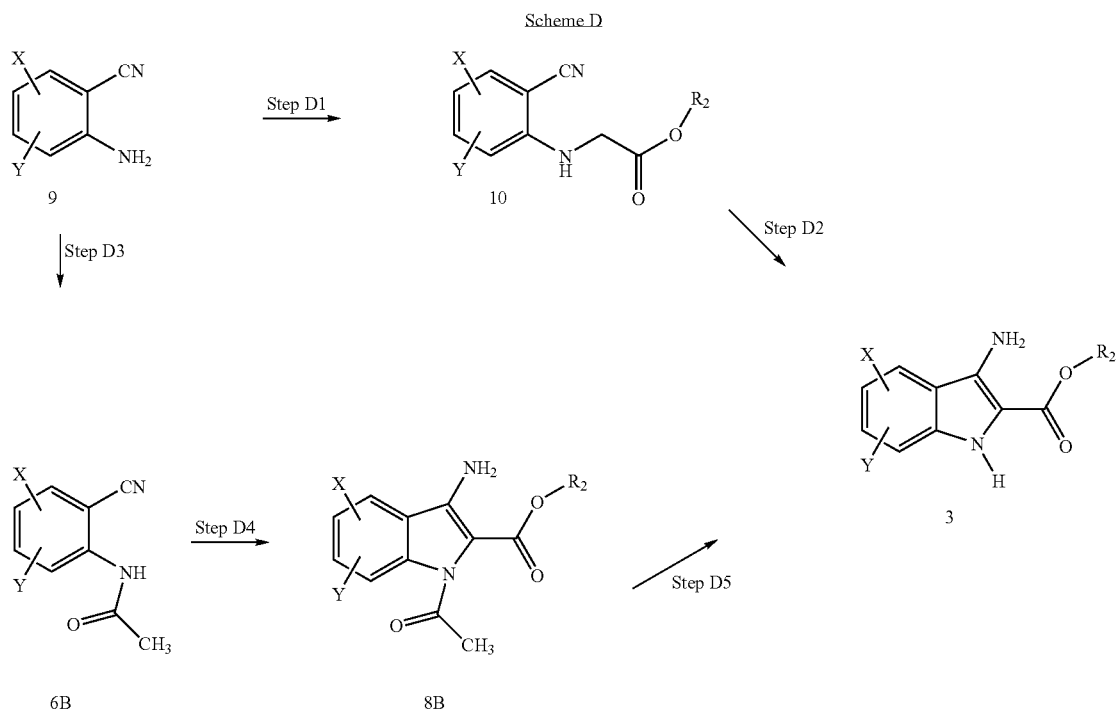

Scheme D illustrates another variation of the synthesis of the 3-amino-indole derivatives useful in the synthesis of the compounds of this invention. Steps D3 to D5, Scheme D are similar to the ones described above in Schemes B and C. Thus synthetic procedures as described above can be utilized in steps D3 to D5. However, in some instances the amino group need not be protected and can be reacted straight with the desirable α-halo-carboxylic acid ester to form the 3-amino-indole derivative, 3 following steps D1 and D2, Scheme D. Thus in step D1, Scheme D, the reaction can be carried out by treating the substituted 2-aminobenzonitrile, 9 with α-halocarboxylic acid ester in the presence of a suitable base such as potassium or sodium carbonate to form the product 10, which is subsequently cyclyzed to indole compound, 3 in the presence of a base such as potassium tert-butoxide.

Scheme E

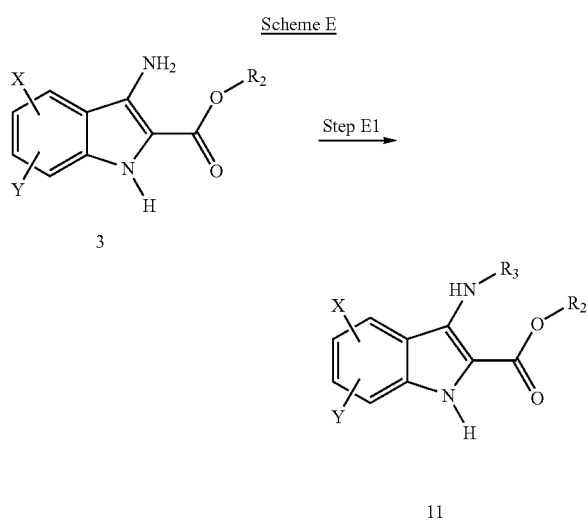

Scheme E illustrates the preparation of various indole compounds of this invention. In step, E1, Scheme E, the 3-amino-indole derivative, 3 produced in accordance with any one of the Schemes A through D as described herein is reacted with suitable halo substituted $R_3$ compound in the presence of a suitable organic solvent as described in U.S. Pat. No. 5,328,920. The reaction is typically carried out at ambient to super-ambient temperature conditions, typically in the temperature range of 20° C. to 150° C. Scheme E is particularly suitable for the preparation of compounds of the method of this invention wherein $R_2$ is $C_{1-6}$alkyl or $C_{1-6}$perfluoroalkyl; $C_{1-4}$alkyl are preferred, ethyl or t-butyl are more preferred.

Scheme F shows various other synthetic approaches to the preparation of the compounds of this invention. In sum, Scheme F depicts two approaches to the preparation of various compounds of this invention by way of transesterification reactions. Any of the other known transesterification reactions can be utilized for the preparation of these compounds. Finally, Scheme F also illustrates, in step F8, the preparation of N-substituted indoles.

In step F1, Scheme F, the carboxylic acid esters, preferably, the alkyl esters of the indole derivatives, 11 are hydrolyzed using a suitable base such as potassium hydroxide to form the corresponding potassium salt, 12. Typically the hydrolysis is carried out in an aqueous medium, alcoholic medium or a mixture thereof. The reaction is generally carried out at ambient or super-ambient temperatures, typically in the temperature range of from about 25° C. to 80° C.

In step F2, Scheme F, the potassium salt, 12 so produced from step F1, Scheme F is reacted with a suitable halo compound to produce the desirable transesterified indole compound, 11A used in the method of this invention. The reaction is typically carried out in a polar or a non-polar anhydrous solvent. Suitable solvents include ethereal solvent such as tetrahydrofuran or polar solvents such as dimethylformamide (DMF). The reaction can be carried out at ambient or super-ambient temperatures, typically temperature in the range of 30° C. to 100° C. is preferred. The reaction can also be carried out in the presence of a catalyst such as potassium iodide.

Steps F3 and F4 of Scheme F illustrate an alternative approach for the preparation of transesterified indole compound, 11A of this invention. In step F3, Scheme F, the ester derivative of an indole compound, 11 is hydrolyzed under acidic reaction conditions at ambient, sub-ambient or super-ambient reaction conditions to form the free carboxylic acid

Scheme F

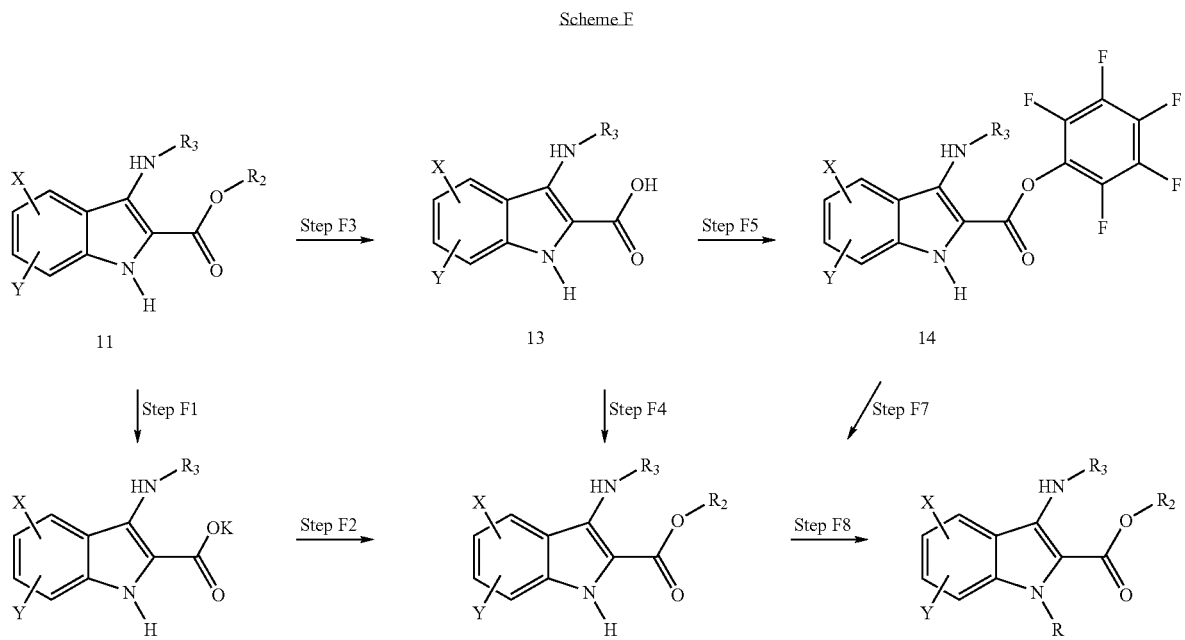

derivative, 13. Suitable acid catalysts include mineral acids such as hydrochloric acid or sulfuric acid; organic sulfonic acids such as methanesulfonic acid, trifluoromethanesulfonic acid or para-toluene sulfonic acid; and carboxylic acids such as acetic acid or trifluoroacetic acid and the like. Solid acid catalysts such as Nafion-H® or H-ZSM-5 can also be employed. Typical reaction temperatures are in the range of from about 0° C. to 50° C.

In step F4, Scheme F, the, carboxylic acid derivative, 13 produced in step F3, Scheme F is esterified to obtain the desirable indole compound, 11A of this invention. The conditions for esterification reaction are varied depending upon the ester that is being formed. Such variation in the reaction conditions are readily appreciated by the one skilled in the art.

For example, the esterification reaction is carried out under essentially neutral conditions in the presence of carboxylic acid activation agents where the resulting product contained a hydrolytically susceptible moiety. However, optionally the esterification can be carried out in the presence of a hindered base such as diethylisopropylamine. Suitable esterification activating agents include benzotriazol-1-yloxytris(dimethylamino)phosphonium hexafluorophosphate (BOP) or benzotriazol-1-yloxytris(pyrrolidino)-phosphonium hexafluorophosphate (PYBOP). The reaction is typically carried out in a polar solvent such as 1-methyl-2-pyrrolidinone (NMP) or DMF. The reaction is generally carried out at sub-ambient to ambient temperatures, i.e., in the temperature range of from about –20° C. to 25° C.

Alternatively, in step F4, Scheme F, the esterification reaction can also be carried out under mildly basic conditions in the presence of a suitable catalyst. Suitable base includes cesium carbonate or potassium carbonate. Optional catalysts include potassium iodide. The reaction is typically carried out at a temperature range of from about 40° C. to 80° C.

In yet an alternative approach, Scheme F, steps F5 and F7 illustrate another method for the preparation of the indole compound, 11A of this invention. In step F5, Scheme F, the carboxylic acid derivative is first esterified to form pentafluorophenyl ester derivative, 14. The reaction is typically carried out in the presence of an organic base such as pyridine and pentafluorophenyl trifluoroacetate as the esterifying agent. The reaction is carried out typically at ambient temperatures such as 20° C. to 30° C.

In step F7, Scheme F, the pentafluorophenyl ester is reacted with desirable esterifying agent to form the desirable indole compound, 11A in the presence of a base such as sodium hydride. Typical solvents suitable for this reaction include NMP or DMF. The reaction is generally carried out at sub-ambient temperatures, typically, in the range of from about –20° C to 0° C.

In step F8, Scheme F, the indole compound, 11A is substituted at the 1-nitrogen with a R moiety as defined herein to form the desirable indole compound, 15. Any of the known N-substitution reactions can be employed for this purpose. Specifically, N-alkylation can be carried out by reacting the unsubstituted indole compound with a suitable alkylating agent such as iodoalkane or alkyl sulfate. Specific examples of such alkylating agents include iodomethane, iodoethane, dimethyl sulfate, diethyl sulfate, methyl triflate and the like. The reaction is typically carried out in the presence of a base such as potassium tert-butoxide at around 0° C. in a suitable polar solvent such as DMF.

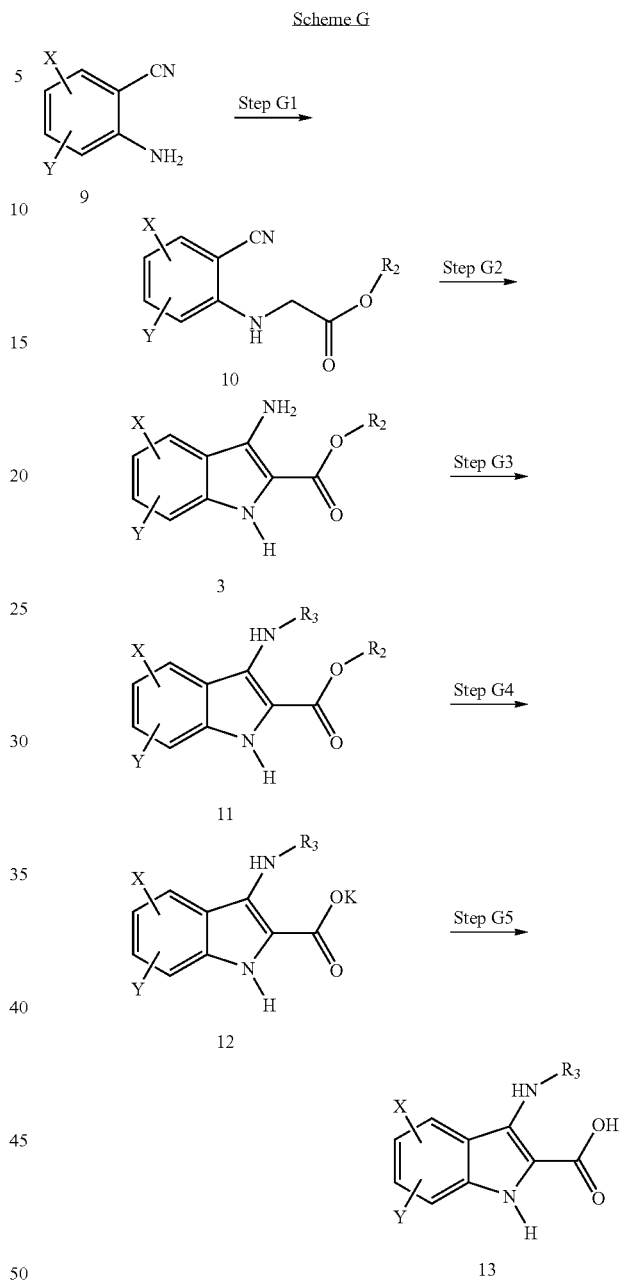

Scheme G illustrates another preferred method for the preparation of a variety of indole compounds of this invention. In step G1, Scheme G, the desirable substituted 2-amino-benzonitrile is reacted with a-halocarboxylic acid ester such as ethyl bromoacetate in the presence of a suitable base such as sodium bicarbonate and in the presence of a catalyst such as sodium iodide in a suitable organic solvent such as ethanol. The reaction is generally carried out at a temperature range of from about 60° C. to 120° C. Higher boiling solvents can be employed if higher reaction temperatures are desirable. In general, higher temperatures accelerate the reaction rates thus requiring shorter reaction time.

In step G2, Scheme G, the N-substituted benzonitrile derivative, 10 is subjected to a cyclization reaction in the presence of a suitable base such as potassium tert-butoxide in solvents such as THF under inert atmospheres such as nitrogen. Typically, the reaction temperature is maintained at or below ambient temperatures, i.e., around 25° C. by cooling the reaction mixture with any suitable coolant such as ice. The resulting substituted indole derivative, 3 is isolated.

In step G3, Scheme G, the substituted indole derivative, 3 is subjected to N-substitution reaction as described in Scheme E. This can be effected typically by reacting indole derivative, 3 with a suitable halo compound such as 4-chloropyridine to form the corresponding pyridinylamino compound, 11. This substitution reaction is typically carried out in a suitable organic solvent such as NMP. The reaction is typically carried out at elevated temperatures, generally, in the range of from about 80° C. to 120° C.

In step G4, Scheme G, the N-substituted compound, 11 is hydrolyzed to form the potassium salt of the indole compound, 12. This step is similar to the one described above in step F1 of Scheme F. The hydrolysis is preferably carried out using potassium hydroxide in ethanol as the solvent.

In step G5, Scheme G, the potassium salt, 11 is treated with a suitable acid such as hydrochloric acid to produce the free carboxylic acid, 13 at ambient reaction temperatures.

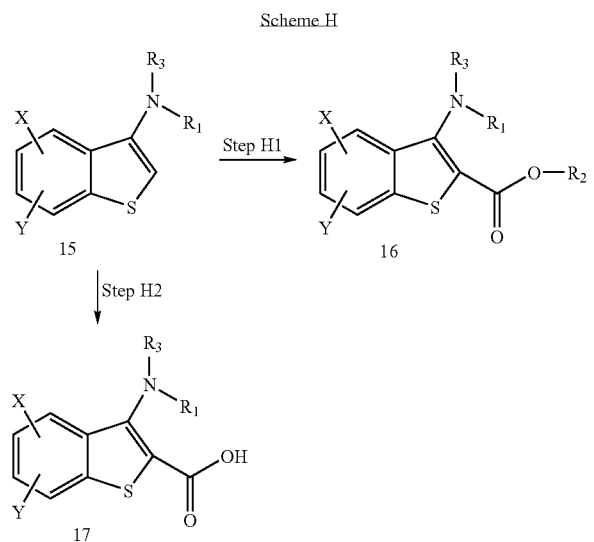

Scheme H

Scheme H shows two procedures for the preparation of benzo(b)thiophene compounds, 16 and 17 of this invention. The starting substituted 3-aminobenzo(b)thiophene, 15 can be prepared by various methods known in the art. For example, as noted above, U.S. Pat. No. 5,328,920 describes a few such procedures.

In step H1, Scheme H, the substituted 3-aminobenzo(b) thiophene, 15 is reacted with a suitable base such as lithium di-isopropylamide to generate in situ anion of compound 15. This reaction is typically carried out at sub-ambient reaction temperatures generally around −120° C to 0° C. The reaction is also conducted in an inert atmosphere such as nitrogen and in a non-polar solvent such as ethereal solvents including diethyl ether, THF, alkane solvents including heptane, hexane, etc. and aromatic hydrocarbons such as ethylbenzene or combinations thereof. The anion of compound 15 so formed in this step is then reacted with any desirable esters of carbonic acid including dialkyl carbonate such as diethyl carbonate. This affords compound 16.

Alternatively, in step H2, Scheme H, compound 15 is reacted with a suitable base such as alkyl lithium to generate the anion which is reacted with carbon dioxide to form the free carboxylic acid compound 17. The anion of compound 15 is typically formed at sub-ambient reaction conditions as described above and then reacted with dry ice, i.e., the solid form of carbon dioxide.

The invention also provides pharmaceutical compositions comprising one or more of the compounds according to this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. An erodible polymer containing the active ingredient may be envisaged. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Flavored unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or, peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

The preferred administration of the pharmaceutical composition of this invention is by an intranasal route. Any of the known methods to administer pharmaceutical compositions by an intranasal route can be used to administer the composition of this invention.

In the treatment of various disease states as described herein, a suitable dosage level is about 0.01 to 250 mg/kg per day, preferably about 0.05 to 100 mg/kg per day, and especially about 0.05 to 20 mg/kg per day. The compounds may be administered on a regimen of 1 to 4 times per day.

Biological Examples

The following test protocols are used to ascertain the biological properties of the compounds of this invention.

The first method involves adding the compound to a cell comprising a vector which comprises at least 100 contiguous nucleotides of an exogenous human interleukin-4 promoter, operably linked to a gene encoding a detectable protein under conditions to permit expression of the detectable protein, and detecting the detectable protein.

Suitable detectable proteins include proteins which may be measured by standard laboratory techniques such as staining methods, for example, β-galactosidase, immunoassays such as those involving FLAG-tagged proteins, luminescent proteins, such as luciferase or GFP.

The relative amount of detectable protein may be determined directly such as using standard laboratory techniques suitable for the detectable protein, for example, by immunochemistry or luminescence. Alternatively the relative amount of detectable protein may be determined indirectly by measuring the mRNA or cDNA level corresponding to the detectable protein.

It is preferred that the cell used in the present method does not express the detectable protein endogenously. However, in an alternative embodiment, the assay conditions may be modified such that the endogenous protein is not expressed when the compound is added to the cell.

It is preferred that cells used in the present method are cells capable of cell culturing techniques. Commercial sources of suitable cells are well known and include the American Type Culture Collection (ATCC), and other vendors. Examples of suitable cells include standard cultured cells such as Chinese Hamster Ovary cells (CHO) cells, lymphocytes, T cells, naive T cells, Th1 cells, Th2 cells, macrophages, or other cells derived from the immune system. Generally, human cells are preferred. Primary cells may also be used in the present method.

The use of mammalian cells are preferred in setting up assays to identify compounds capable of modulating one or more Th2 cytokines. The use of primate cells are more preferred in such assays, and use of human cells are especially preferred in such assays.

Cells may be derived from any tissue of the body, but it is generally preferred that cells are derived from the immune system, such as lymphocytes, T cells, naive T cells, Th1 cells, Th2 cells, macrophages, or other cells derived from the immune system.

The detectable protein may be a directly measurable or detectable protein, such as described above, for example, β-galactosidase, FLAG-tagged proteins, luciferase or GFP. Alternatively, the detectable protein may be indirectly measurable, such as a protein which initiates a pathway, the initiation of which is detectable. An example of the latter is a transcription factor the expression of which permits detectable up- or down-regulated transcription of a second gene. An indirectly measurable detectable protein may involve a phenotypic change, for example, apoptosis.

In one embodiment of the invention, the level of the detectable protein is compared to the level of the detectable protein in the absence of the compound.

In an alternative embodiment of the invention, the level of the detectable protein is compared to the level of the detectable protein in the presence of a reference compound. Reference compounds may be known modulators of a Th2 cytokine, such as cyclosporin A, FK-506 and rapamycine etc., or may be previously unknown modulators of a Th2 cytokine.

The Th2 cytokines in the present invention are IL-4, IL-5 and IL-13.

In the Biological Examples that follow, the following abbreviations are used:

| | |
|---|---|
| Al(OH)$_3$ | Aluminum hydroxide |
| Anti-DNP | Anti-dinitrophenyl antibody |
| Anti-OVA | Anti-ovalbumin antibody |
| BALF | Bronchoalveolar lavage fluid |
| CsA | Cyclosporin A |
| DMSO | Dimethyl sulfoxide |
| DNP-KLH | Dinitrophenol-keyhole limpet hemocyanin |
| ED$_{50}$ | Median effective dose |
| ELISA | Enzyme-linked immunosorbent assays |
| GFP | Green fluorescent protein |
| IC$_{50}$ | Inhibitory concentration 50% |
| IFN-γ | Interferon-gamma |
| IgE | Immunoglobulin E |
| IgG1 | Immunoglobulin G1 |
| IgG2a | Immunoglobulin G2a |
| IL-4 | Interleukin-4 |
| IL-5 | Interleukin-5 |
| IL-13 | Interleukin-13 |
| i.n. | Intranasal |
| i.p. | Intraperitoneal |
| i.v. | Intravenous |
| LD$_{50}$ | Median lethal dose |
| NY-1 | Th1 cell line named NY-Th1 |
| NY-2 | Th2 cell line named NY-Th2 |
| PC$_{400}$ | Post carbachol concentration that increases the SR$_L$ by 400% over baseline |
| p.o. | By mouth (per os) |
| PHA | Phytohaemagglutanin |
| R$_L$ | Resistance in the lung (pulmonary) |
| SD | Standard deviation |
| SE | Standard error |
| SEM | Standard error of mean |
| STAT-6 | Signal transducer and activator of transcription-6 |
| SR$_L$ | Specific resistance in the lung |
| s.c. | Subcutaneous |
| Th | T helper |
| Th1 | T-helper 1 |
| Th2 | T-helper 2 |

IL-4 Luciferase Assay in Jurkat Cells

An IL-4 luciferase assay may be used to screen for compounds which modulate levels of IL-4 transcription. Several luciferase assays have been developed to screen compounds that are effective to transcriptionally modulate expression of the gene and thereby affect the level of the protein encoded by the gene which is expressed by the cell. For example, a transcriptional assay method is used to show that a 11 base pair DNA sequence motif is involved in the human IL-4 gene that is responsible for the T-cell activation signals, see Abe, E., et al., *Proc. Natl. Acad. Sci. USA*, (1992), 89, 2864–2868. It has also been shown that nuclear factor-IL-6 (NF-IL-6) is involved in transcriptional activation of the human IL-4 promoter in T cells by screening cDNA expression library from Jurkat T cells and isolating a cDNA encoding NF-IL-6, see Davydov, I. V., et al., *J. Immunol.*, (1995), 155(11), 5273–5279.

The contribution to T cell specific expression by other promoter sites has been assessed in a transient expression assay with IL-13 promoter constructs linked to a luciferase gene, focusing initially on the core binding factor (CBF) site, which is footprinted in vivo upon T cell activation, see Taylor, D. S., et al., *J. Biol. Chem.*, (1996), 271(14), 14020–14027. It has been reported recently that human IL-4 promoter exists in multiple allelic forms that exhibit distinct transcriptional activities in IL-4-positive T cells, see Song, Z. et al., J. Immunol., (1996), 156(2), 424–429. More recently, U.S. Pat. Nos. 5,863,733; and 5,976,793 disclose methods of transcriptionally modulating gene expression and of discovering chemicals capable as gene expression modulators.

Isolation of the Human IL-4 Gene Promoter

A 6.7 kb fragment comprising nucleotides −6635 to +66 of the IL-4 gene promoter (FIG. 4; SEQ ID NO:1) was isolated from a human genomic P-1 library, clone F0178, obtained from BIOS Laboratories (New Haven, Conn.) using an IL-4 specific, 5' end biased, probe (Arai et al., *J. of Immunol.*, (1989), 142, 274–282). The promoter construct was generated by ligating two EcoRI restriction fragments of 5.5 and 1.2 KBs respectively. A HindIII restriction site was added to the 3' end of the 1.2 KB EcoRI fragment and cloned into a similar site on the multiple cloning region on pGL3Neo. Similarly, a XhoI restriction site was added to the 5' end of the 5.5 KB EcoRI fragment and cloned into the XhoI site on pGL3Neo. The IL-4 promoter construct was verified by sequencing.

Jurkat cells are grown in RPMI 1640, Gibco/BRL, catalog no: 11875-093; 10% FBS Gibco/BRL, cat no: 16000-096; 1% antibiotic/antimycotic, Gibco/BRL, cat no: 15240-096) and transfected with the above DNA following the protocol described by Staynov et al., *Proc. Natl. Acad. Sci. USA*, (1995), 92, 3606–3610, and selected against 800 µg/ml of G418 (Geneticin, Gibco/BRL, cat no:10131-035). Monoclonal lines, 1F7, F8 and C5 are derived from the stable transfected polyclonal population by the limiting dilution method and used for the assay. The monoclonal cell lines are cultured in the above described medium in the presence of 400 µg/ml G418.

The IL-46.7 Luc monoclonal lines are grown in 150 cm vented T-flasks seeded at 100,000 cells/ml for two days. The cells are harvested, resuspended in fresh media and plated at a density of 50,000 cells/well in 120 µL volume, in a 96 well plate and grown for 16 hours. Test compounds are added to the culture (in DMSO final concentration of 0.5%) in replicates of 3 or 4 in a 15 µL volume. Typically, dose response curves are generated using three (10, 1 and 0.1 µM) or five concentrations (10, 1, 0.1, 0.01 and 0.001 µM). The cultures are then stimulated with 50 ng/ml of phorbol 12-myristate 13-acetate (PMA, Sigma, cat no: P-8139); and 1.0 µM calcium ionophore ($A_{23187}$, Sigma, cat no: C-7522); in 25 µL of media for 8 hours. The stimulation process is terminated by the addition of 50 µL s of 1×lysis buffer (25 mM Tris Phosphate, pH 7.8, 2.0 mM DTT, 2.0 mM EDTA, 100 ml/L glycerol, 1.0% Triton X-100 (v/v)). The cells are incubated in the presence of lysis buffer for 5 minutes, pipetted up and down, 5×, to ensure complete lysis. A 100 µL aliquot of the cell lysate is transferred to white luminometer plates (Dynatech) and assayed for luciferase activity with a Dynatech luminometer. The substrate, luciferase reagent (470 µM luciferin, 530 µM ATP, 270 µM Coenzyme A, and 33.3 mM DTT) is dissolved in 2× luciferase assay buffer (20 mM Tricine, 1.07 mM $(MgCO_3)_4Mg(OH)_2 \cdot 5H_2O$, 2.67 mM $Mg\ SO_4$, 0.1 mM EDTA, pH 7.8).

All experimental plates included non-induced and induced control wells. Additionally, CsA (Cyclosporin A, Sigma Cat no: C-3662) at concentrations of 1, 0.3, 0.1, 0.03 & 0.01 µM is included on the plates as a positive control.

Analysis of Results: A five-six fold induction (determined by the ratio of stimulated to non stimulated) is seen with 6.7IL-4-Luc. The results generated from the assay are expressed as percent activity.

(Luc activity with compound)−(mean uninduced)×
100(mean induced control)−(mean uninduced)

The primary assay measured the effects of the ability of a compound to modulate the level of a reporter gene, luciferase, linked to a human IL-4 promoter transfected into a human Jurkat cell line. Using this assay, 250 positive compounds were found capable of modulating levels of IL-4.

Additional assays may be used to further characterize the ability of the compound to modulate other Th2 cytokines for example, IL-13, or alternatively, to characterize the ability of the compound to modulate TH1 cytokines, for example, IFN-γ.

In Table 1, effects of the compound of the present invention on gene expression of Jurkat cells transfected with IL-4, IL-13 and IFN-γ are presented.

TABLE 1

Inhibition of IL-4 and IL-13 gene expression in Jurkat cell line by the compound of the present invention

| Compound | 6.7-IL-4 Luc (% of control) | 2.1-IL-13-Luc (% of control) | 2.7-IFN-γ-Luc (% of control) |
| --- | --- | --- | --- |
| 3-(4-pyridinylamino)-1H-indole-2-carboxylic acid (Example 28) | 62 ± 29 | 50 ± 12 | 100 ± 15 |
| CsA ($IC_{50}$, µM) | 0.06 ± 0.01 | 0.06 ± 0.001 | 0.06 ± 0.001 |

IFN-γ Luc Assay

The human IFN-γ promoter fragment, comprising nucleotides −3218 to +128, was cloned into pGL3NEO (SstI/Hind III) to give IFN-γ Luc. Jurkat cells were (grown in RPMI 1640, 10% FBS, 1% antibiotic/antimycotic) transfected with the above DNA (protocol described by Staynov et al., *Proc. Natl. Acad. Sci. USA*, (1995), 92, 3606–3610, and selected against 800 µg/ml of G418 (Geneticin). Monoclonal lines were derived from the stable transfected polyclonal population and used for the assay. The monoclonal cell lines were cultured in the above described medium in the presence of 400 µg/ml G418.

Jurkats containing 2.3IFN-γ Luc (monoclonal lines) were plated at a density of 50,000 cells in 120 µl per well, and grown for 16 hours. The cultures were then stimulated with 10 ng/ml of phorbol 12-myristate 13-acetate (PMA) and 1.0 µm calcium ionophore $A_{23187}$ in 10 µl of media for 8 hours. The stimulation process was terminated by the addition of 50 µLs of 1× lysis buffer (25 mM Tris Phosphate, pH 7.8, 2.0 mM DTT, 2.0 mM EDTA, 100 ml/L glycerol, 1.0% Triton X-100 (v/v)). The cells were incubated in the presence of lysis buffer for 5 minutes, pipetted up and down, 5×, to ensure complete lysis. A 100 µl aliquot of the cell lysate was transferred to white luminometer plates (Dynatech) and assayed for luciferase activity with a Dynatech luminometer. The substrate, luciferase reagent (7.1 mg luciferin, 14.6 mg ATP, 10.4 mg Coenzyme A, and 250 mg DTT, in 50 ml volume) was dissolved in 2× luciferase assay buffer (14.33 g Tricine, 2.07 g $(MgCO_3)_4Mg(OH)_2.5H2O$, 2.63 g Mg $SO_4$, 0.15 g EDTA in 2 L of water, and pH was adjusted to 7.8).

In order to use this assay to screen for agonists or antagonists from a chemical library, desired doses of a compound were added directly along with PMA/$A_{23187}$ mix.

Greater than twenty fold induction (determined by the ratio of stimulated to non stimulated) was seen with IFN-γ Luc. The results generated from the HTPS will be expressed as a percentage of the control at given concentrations (viz.: 0.1 μM, 1 μM, 10 μM).

REFERENCES: Staynov, D. Z., Cousins, D. J., and Lee, T. K., *Proc. Natl. Acad. Sci. USA*, (1995), 92, 3606–3610.

IL-13 Luc Assay

The human IL-13 promoter fragment comprising nucleotides −2154 to +53 (as described by Dulganov et al., *Blood*, (1996), 87, 3316–3326), was cloned into pGL3NEO (KpNI/ Hind III) to give 2.1IL-13 Luc. Jurkat cells were (grown in RPMI 1640, 10% FBS, 1% antibiotic/antimycotic) transfected with the above DNA (protocol described by Staynov et al., *Proc. Natl. Acad. Sci. USA*, (1995), 92, 3606–3610) and selected against 800 μg/ml of G418 (Geneticin). Monoclonal lines were derived from the stable transfected polyclonal population and used for the assay. The monoclonal cell lines were cultured in the above described medium in the presence of 400 μg/ml G418.

Jurkats containing 2.1IL-13 Luc (monoclonal lines) were plated at a density of 50,000 cells in 120 μL per well, and grown for 16 hours. The cultures were then stimulated with 10 ng/ml of Phorbol 12-myristate 13-acetate (PMA) and 1.0 μM calcium ionophore $A_{23187}$ in 10 μL of media for 8 hours. The stimulation process was terminated by the addition of 50 μL s of 1× lysis buffer (25 mM Tris Phosphate, pH 7.8, 2.0 mM dithiothritol (DTT), 2.0 mM ethylenediamine tetraacetic acid (EDTA), 100 ml/L glycerol, 1.0% Triton X-100 (v/v)). The cells were incubated in the presence of lysis buffer for 5 minutes, pipetted up and down, 5×, to ensure complete lysis. A 100 μL aliquot of the cell lysate was transferred to white luminometer plates (Dynatech) and assayed for luciferase activity with a Dynatech luminometer. The substrate, luciferase reagent (7.1 mg luciferin, 14.6 mg ATP, 10.4 mg Coenzyme A, and 250 mg DTT, in 50 ml volume) was dissolved in 2× luciferase assay buffer (14.33 g Tricine, 2.07 g $(MgCO_3)_4Mg(OH)_2.5H2O$ 2.63 g $MgSO_4$, 0.15 g EDTA in 2 L of water, and pH was adjusted to 7.8).

In order to use this assay to screen for agonists or antagonists from a chemical library, desired doses of a compound were added directly along with PMA/$A_{23187}$ mix.

Greater than fifteen fold induction (determined by the ratio of stimulated to non stimulated) was seen with IL-13 Luc. The results generated from the high throughput screening (HTS) will be expressed as a percentage of the control at given concentrations (viz.: 0.1 μM, 1 μM, 10 μM).

REFERENCES: Staynov, D. Z., Cousins, D. J., and Lee, T. K. *Proc. Natl. Acad. Sci. USA*, (1995), 92, 3606–3610.

The second method involves adding the compound to a primary human cell secreting detectable cytokines in particular IL-4 protein under conditions to permit expression of the detectable protein, and detecting the detectable protein.

Generation and Use of Human Primary Th1 and Th2 Cells

The methods described herein permit polarization of primary human peripheral blood cells into Th1 and Th2 cells and generation of sufficiently large quantities of Th1 and Th2 cells, e.g., billions of cells, to allow drug screening. Briefly, $CD4^+CD45RA^+T$ cells, isolated from donor peripheral blood mononuclear cells of healthy donors, are educated in the presence of anti-CD3/ CD28 antibodies and various growth factors to obtain either a Th1-like or Th2-like phenotypes as determined by the known cytokine profiles of these two cell types. Primary human Th1 cells secreted IFN-γ and IL-2 cytokines while primary human Th2 cells secreted IL-4, IL-5, IL-13 and basal amounts of IFN-γ that are measurable by enzyme linked immuno absorption assay (ELISA).

Generation and Maintenance of Th1 and Th2 Cell Lines from Human Blood

Peripheral blood mononuclear cells (PBMC) are prepared from human blood by Ficoll-Hypacque (Pharmacia). The cells are washed two times in Hanks balanced salt solution (HBSS) and counted.

Naïve T cells ($CD4^+/CD45RA$ ) are prepared by negative selection method using following antibodies and Dynabeads: anti-CD8, anti-HLA-DR, (where HLA means human leucocyte antigen) anti-CD14, anti-CD16, anti-CD19, anti-CD45RO antibodies (all from R&D Systems, 1–2 μg/ml) are added to the cells, and the cells are kept on ice for 30 min. The cells are washed two times in HBSS, and goat anti-mouse Ig-beads, (bead:target ratio, 5:1) are added. The cells and beads are slowly rotated at 4° C. for 20 min. (following the protocol supplied from Dynal). The supernatant is removed and fresh goat anti-mouse Ig-beads are added to the supernatant, which is slowly rotated at 4° C. for 20 min. The cells are counted and phenotypically characterized by flow cytometric analysis. Typically after negative selection purity of $CD4^+/CD45RA^+$ cells were 96%. The $CD8^+$, $CD14^+$, $CD16^+$ $CD19^+$ and $CD45RO^+$ cell contamination were below detectable levels (<0.1%)

Generation of Th1/Th2 Cells: Twenty four well plates are coated with 300 μL anti-CD3 Ab (10 μg/ml, in PBS 1–2 h at 37° C. or overnight at 4° C.), and washed two times with PBS. $CD4^+/CD45RA^+$ cells at a density of $10^6$/ml in RPMI, is prepared and added to RPMI medium containing 10% Hyclone serum/ glutamine and 1–2 μg/ml anti-CD28 Ab. The cells are split in two aliquots. For Th1 cells: anti-IL-4 Ab (1–2 μg/ml), IFN-γ (1 μg/ml, or 5000 units/ml) are added to the wells. For Th2 cells: IL-4 (100–200 ng/ml), anti-IFN-γ neutralizing Ab (1–2 μg/ml), anti-IL-12 neutralizing Ab (1–2 μg/ml) are added into the wells. The cells are incubated for 2–3 days at 37° C. The cells are transferred to fresh wells and grown in 200 units/ml IL-2 for 2 weeks by feeding them every other day with IL-2 containing medium and splitting the cultures 1:2 or 1:3 as needed. The degree of polarization is determined by intracellular staining of cells with anti-IFN-γ and anti-IL-4 antibodies from Pharmingen, and using flow cytometry from Becton Dickinson (BD), according to manufacturers description. The cells are stimulated with PHA and alloantigens at day 14 and 28 as described below. Eight days after the second allostimulation the cells can be used for compound screening or frozen for future use. For compound testing, large quantities of Th1 and Th2 cells derived from a given donor (NYTh1 and NYTh2) were expanded and frozen as aliquots in liquid nitrogen. The cells are thawed and cultured as and when needed. The thawed cells are stimulated with alloantigen/PHA combination. The cells are used for compound screening after 8–10 days in culture.

Re-Stimulation by Allogeneic Cells: Human PBMCs, to be used as alloantigens, are isolated from freshly drawn blood by Ficoll separation. Cells are resuspended in medium containing 50 μg/ml mitomycin C and incubated for 40 minutes at 37° C. and then washed extensively to remove all of the Mitomycin C. Cells are counted and diluted to a final concentration of $2\times10^6$/ml in medium containing 10 μg/ml PHA and 200 units/ml IL-2. TH1 or Th2 cells are ($3\times10^5$ cells/ml) mixed with above PBMC in 1:1 ratio in 24 well plates and incubated at 37° C. The cells so formed can be used for compound testing typically after 8 to 10 days.

Compound Testing

Ninety six well Falcon tissue culture plates (Fisher Scientific) are coated with 100 microliters per well of 10 μg/ml anti-CD3 (PharMingen) antibody in phosphate buffered saline (PBS) and stored at 4° C. one day before the experiment.

erate, the results are expressed as "proliferation" in the tables. (Toxic compounds inhibited the proliferation of Th cells).

In Table 2, effects of a compound of the present invention, 3-(4-pyridinylamino)-1H-indole-2-carboxylic acid, on human primary Th2 cells are presented. Th2 cells were activated with anti-CD3 and anti-CD28, as described in methods section in the absence or presence of the compounds of this invention. Supernatants were collected for cytokine measurements by standard ELISA 48 hr after stimulation. The cell numbers are determined by MTS Assay Kit (Promega) by incubating the remaining cells for additional 20 hrs. Standard deviations of triplicate cultures are given.

TABLE 2

Effects of 3-(4-pyridinylamino)-1H-indole-2-carboxylic acid (Example 28) on Cytokine Expression and proliferation of Human Th2 cells

| μM | Proliferation (% control) | | IL-5 (% control) | | IL-4 (% control) | | IFN-γ (% control) | | IL-13 (% control) | |
|---|---|---|---|---|---|---|---|---|---|---|
| | mean | SD | mean | SD | mean | SD | mean | SD | mean | SD |
| 10 | 71.55 | 0.07 | 53.90 | 3.96 | 30.80 | 4.95 | 75.00 | 10.32 | 68.40 | 4.10 |
| 3 | 72.05 | 0.64 | 70.40 | 0.00 | 36.40 | 0.00 | 83.50 | 7.07 | 73.40 | 0.71 |
| 1 | 77.25 | 1.06 | 70.70 | 2.12 | 42.55 | 2.90 | 89.25 | 5.30 | 75.15 | 1.77 |
| 0.3 | 80.60 | 3.68 | 70.80 | 7.21 | 45.00 | 0.00 | 92.10 | 2.26 | 80.60 | 0.00 |
| 0.1 | 86.70 | 1.84 | 78.60 | 5.37 | 59.75 | 1.77 | 91.75 | 0.21 | 82.30 | 0.85 |
| 0.03 | 85.05 | 6.86 | 85.20 | 0.00 | 65.30 | 0.00 | 91.60 | 2.97 | 86.40 | 0.00 |
| 0.01 | 89.50 | 8.34 | 102.45 | 3.46 | 102.15 | 3.61 | 96.90 | 1.70 | 91.05 | 1.91 |

On the day of assay, anti-CD3 antibody coated plates are washed with PBS once to remove all soluble anti-CD3 antibody. T cells are centrifuged and washed with 1640 RPMI cell culture medium (Gibco) without IL-2, counted, and resuspended to a final concentration of $1\times10^6$ cells/ml. Stock solutions of the compounds of this invention (10 mM concentration) are diluted to a final concentration of 10 μM in 0.1% DMSO (dimethylsulfoxide) and titrated using 3-fold dilutions over 7 rows for $IC_{50}$ determinations. All compounds and controls are assayed in triplicates. Control wells consist of 0.25% ethanol, 0.1% DMSO, anti-CD3 and anti-CD28 stimulated cells (served as positive control) or unstimulated cells (as negative control) in triplicate. Cyclosporin A (CsA) in ethanol (at 1 μM concentration), titrated over seven rows, is included as a plate control within the first plate of each assay. 1 μg/ml of anti-CD28 antibody (R&D Systems) as a costimulus is added to all wells and 100 microliters of $1\times10^5$ cells is pipetted into each well.

Cells are incubated at 37° C. in a 5% $CO_2$ atmosphere. After 48 hours, supernatants are removed for ELISA testing. Percent control is measured by subtracting the background from the mean OD of triplicates and is compared to the mean OD of controls minus the background i.e. (xOD of compound−background)/(xOD controls−background) X100 IL-5 (PharMingen), IL-4 (R&D Systems), IL-13 (R&D Systems) and IFN-γ (R&D Systems) are measured by ELISA kits and results expressed as % Control. After 48 hours, with the remaining cells a "viability test" is performed using a non-radioactive MTS assay kit purchased from Promega. Because the viable cells continue to prolif- In Table 3, combined data from 10 different experiments is presented. Th2 cells were activated as described above. Standard deviations were less than 15% and hence not included. As control CsA, as a nonselective cytokine inhibitor was used. The compound of this invention, 3-(4-pyridinylamino)-1H-indole-2-carboxylic acid, selectively inhibited IL-4, but not IFN-γ and cell proliferation, whereas CsA inhibited IL-4, IFN-γ and cell proliferation.

TABLE 3

Summary of effects of 3-(4-pyridinylamino)-1H-indole-2-carboxylic acid (Example 28) on human Th2 cells

| Human primary Th2 cells treated with: | IL-4 $IC_{50}$ (μM) | IL-13 $IC_{50}$ (μM) | IL-5 $IC_{50}$ (μM) | IFN-γ $IC_{50}$ (μM) | Prol. $IC_{50}$ (μM) | IFN-γ/ IL-4 Ratio |
|---|---|---|---|---|---|---|
| 3-(4-pyridinylamino)-1H-indole-2-carboxylic acid (n = 10) | 0.24 | ≈10 | ≈10 | >10 | >10 | >41 |
| Cyclosporin A (CsA) (n = 25) | 0.006 | 0.008 | 0.008 | 0.008 | | 1.0 |

In Table 4 effect of a compound of this invention, 3-(4-pyridinylamino)-1H-indole-2-carboxylic acid, on human primary NYTh1 cells is presented. NYTh1 cells are activated with anti-CD3 and anti-CD28, as described in Tables 1 and 2. The data from 8 different experiments were combined, all of which used 3-(4-pyridinylamino)-1H-indole-2- carboxylic acid. Standard deviations were less than 15% and hence not included. CsA, a non-specific immunosuppressive drug was used as control. These experiments demonstrated that a compound of this invention had no effect on Th1 cells.

TABLE 4

Summary of effects of 3-(4-pyridinylamino)-1H-indole-2-carboxylic acid (Example 28) on human Th1cells

| Human primary Th1 cells treated with | IFN-γ $IC_{50}$ (μM) | Proliferation $IC_{50}$ (μM) | IFN-γ/IL-4 Ratio |
|---|---|---|---|
| 3-(4-pyridinylamino)-1H-indole-2-carboxylic acid (n = 8) | >10 | >10 | — |
| Cyclosporin A | 0.006 | 0.005 | 1.0 |

In Table 5 effect of several close analogs of 3-(4-pyridinylamino)-1H-indole-2-carboxylic acid on human primary Th2 cells are presented. The cells were activated with anti-CD3 and anti-CD28, as described in methods section in the absence or presence of several of the compounds of the present invention and results were given as $IC_{50}$ in μM. Standard deviations were less than 15% and hence not included. As can be seen various compounds of the present invention inhibit the expression of IL-4 selectively and have a similar selectivity profile as that of 3-(4-pyridinylamino)-1H-indole-2-carboxylic acid.

TABLE 5

Summary of Activity and Selectivity Profile of the Compounds of the Present Invention

| Compound # | IL-4 $IC_{50}$ μM | Prolif. $IC_{50}$ μM | IL-5 $IC_{50}$ μM | IFN-γ $IC_{50}$ μM | IL-13 $IC_{50}$ μM |
|---|---|---|---|---|---|
| Example 11 | >10 | >10 | >10 | >10 | >10 |
| Example 24A | 2.0 | >10 | >10 | >10 | >10 |
| Example 28 (maleate salt) | 0.24 | >10 | >10 | >10 | ~10 |
| Example 76 | 4.0 | >10 | >10 | >10 | >10 |
| Example 77 | 3.6 | >10 | >10 | >10 | >10 |
| Example 78 | 0.3 | >10 | >10 | >10 | >10 |
| Example 79 | 5.0 | >10 | >10 | >10 | >10 |
| Example 80 | 6.0 | >10 | >10 | >10 | >10 |
| Example 81 | 6.0 | >10 | 7.0 | 9.5 | >10 |
| Example 82 | 0.15 | >10 | >10 | >10 | >10 |
| Example 83 | 1.0 | >10 | >10 | >10 | >10 |
| Example 84 | 1.0 | >10 | >10 | >10 | >10 |
| Example 85 | 0.9 | >10 | >10 | >10 | >10 |
| Example 86 | 1.0 | >10 | >10 | >10 | >10 |
| Example 87 | 0.6 | >10 | 2.0 | >10 | >10 |
| Example 88 | 2.5 | >10 | >10 | >10 | >10 |
| Example 89 | 2.5 | 4.0 | 8 | >10 | >10 |
| Example 90 | 1.0 | >10 | >10 | >10 | >10 |
| Example 91 | 1.0 | >10 | >10 | >10 | >10 |
| Example 92 | 0.45 | >10 | >10 | >10 | >10 |

In Table 6 the effect of 3-(4-pyridinylamino)-1H-indole-2-carboxylic acid on steady state IL-4 mRNA level is presented. Human Th2 cells were activated with anti-CD3 and anti-CD28 (as described in methods) in the presence of 10 μM solution of 3-(4-pyridinylamino)-1H-indole-2-carboxylic acid or 100 nM Cyclosporin A (CsA) for 18 hours. RNAs were isolated from the harvested cells and analyzed for IL-4 message by Taqman. GAPDH message was used as an internal standard for normalization. The percent activity was calculated by treating the values from not drug treated, anti-CD3 and anti-CD28 stimulated Th2 cells as 100%. Table 6 summarizes data from two independent experiments. In the second experiment IL-4 protein levels were also determined by standard ELISA in culture supernatants as described earlier. These results demonstrate that 3-(4-pyridinylamino)-1H-indole-2-carboxylic acid inhibits IL-4 mRNA in primary human T cells.

TABLE 6

Human Th2 IL-4 transcriptional assay

| Treatment of human primary Th2 cells for 18 hrs | RNA Exp #1 % activity | RNA Exp #2 % activity | IL-4 PROTEIN Exp #2 pg/ml |
|---|---|---|---|
| Unstimulated | 6 | 24 | 3.2 +/− 0.0 |
| Stimulated: CD3/CD28 | 100 | 100 | 625.0 +/− 23 |
| Stimulated: CD3/CD28 + 3-(4-pyridinylamino)-1H-indole-2-carboxylic acid (Example 28) | 44 | 45 | 286.2 +/− 19 |
| Stimulated: CD3/CD28 + Cyclosporin A | 12 | ND | ND |

ND - not determined.

A third assay utilized in the present invention involves an in vitro cytotoxicity assay. This assay is used to further characterize the compounds in order to assess toxic activities of compounds on contact inhibited, non-dividing 3T3 fibroblasts. Other toxicity assays may be used.

Any compound killing 3T3 fibroblast cells was omitted from further studies.

Contact inhibited Swiss 3T3 fibroblasts are purchased from ATCC. The cells are maintained in 1640 RPMI supplemented with 10% fetal bovine serum (Gibco).

On day of assay, cells are detached from flasks by trypsinization, washed in medium and counted. 100 microliters of $2.5 \times 10^4$ cells per well are plated into Falcon brand 96 well tissue culture plates and cells incubated at 37° C. in presence of 5% $CO_2$ for 2 days or until confluent.

On day 2 of assay, 75 microliters of media is added to each well and 25 μL of test compounds are added at concentrations ranging from 10 to 0.01 μM. All compound dilutions are assayed in triplicate. Controls include 10 μM methotrexate (Sigma), 10 μM actinomycin D (Sigma) and 10 μM cyclosporin A (Sigma). Cells are returned to the incubator for 2 days.

After 2 day incubation, the 3T3 cells are assayed for viability using an MTS Assay Kit (Promega). Media is added to blank wells for background calculations. After 2 hours incubation in kit reagent, the optical density at 490 nm for each compound and control is determined by plate reader.

Results are expressed as percent cytotoxicity, i.e., (mean OD of compound wells−background OD)/(mean OD of controls−background).

Drugs which are used clinically may be used as controls in this assay, and include drugs which are expected to have no effect on 3T3 cells, for example, steroids, cyclosporin A, metotraxate, etc. or drugs which have known toxic effects, for example, Actinomycin D.

In Table 7, effect of 3-(4-pyridinylamino)-1H-indole-2-carboxylic acid and certain known standard compounds on the viability of quiescent 3T3 cells are presented. As expected, actinomycin D was the only compound which effected the viability of non-dividing cells. Note that starting concentration of CsA was 1 μM. 3-(4-pyridinylamino)-1H- indole-2-carboxylic acid exhibited no toxic effects on these cells (Various other compounds of the present invention are also negative in this assay).

TABLE 7

Lack of in vitro cytotoxicity of
3-(4-pyridinylamino)-1H-indole-2-carboxylic acid
(Example 28)

| Compounds µM | Medium % control | Example 28 % control | Actinomycin D % control | Methotrexate % control | Dexamethasone % control | Cyclosporin A % control |
|---|---|---|---|---|---|---|
| 10 | 100 | 99.1 | 16.8 | 92.4 | 60.5 | 99.8 |
| 3 | 100 | 109.7 | 29.7 | 93.8 | 60.7 | 103.0 |
| 0.1 | 100 | 110.7 | 28.2 | 98.9 | 64.2 | 104.0 |
| 0.03 | 100 | 111.1 | 33.9 | 100.0 | 67.8 | 105.0 |
| 0.01 | 100 | 111.8 | 67.2 | 102.8 | 71.6 | 105.5 |
| 0.003 | 100 | 1116.3 | 74.9 | 105.2 | 77.9 | 114.4 |
| 0.001 | 100 | 124.0 | 79.0 | 113.2 | 100.0 | 121.0 |

In Vivo Experiments

In vivo immunological assays or disease models may also be used to further characterize the ability of a compound to modulate Th2 cytokine levels. Such assays are well known in the art, and numerous protocols have been published. The following are examples of in vivo assays that may be used to further characterize the ability of a compound to modulate Th2 cytokine levels and thus demonstrate the efficacy of IL-4 inhibition.

Unless stated otherwise, in all of the following in vivo experiments a maleate salt of the 3-(4-pyridinylamino)-1H-indole-2-carboxylic acid (Example 28) was used.

In-Vivo Ovalbumin (OVA) Mouse Model

This model is designed to determine the ability of a test article to modulate an antigen-induced pulmonary inflammatory cell accumulation in sensitized Balb/c mice from Charles River Laboratories. The mice are given a two week time period from arrival date prior to sensitizations.

Sensitizations and Challenge

On days 0, 7, 14, each animal is injected intraperitoneal (i.p.) with a 0.2 ml Ovalbumin Hydragel solution. Each animal receives 10 µM of Ovalbumin in 0.2 mL of Hydragel, aluminum hydroxide adsorptive gel containing 2% aluminum oxide. On Day 21, the animals are dosed with test compounds 30–60 minutes prior to 5% Ovalbumin aerosolized challenge. On day 22, BALF samples are collected from one group of animals and used for cytokine analysis. On day 24, BALF is obtained from a second group of animals and used for differential cell counts.

Methods and Experimental Design

Test System: Female Babl/cJ mice (Jackson Laboratories), approximately 6–9 weeks old, each weighing approximately 20 to 25 grams, are divided into ten animals per group.

Acclimation/Quarantine: Following arrival of the mice, the animals are assessed as to their general health by a member of the veterinary staff or suitable designee. Prior to experiments, animals are housed for a minimum of 7 days in order to acclimate them to the laboratory environment and to observe them for the development of infectious disease. Any animals considered unacceptable for use in this study are replaced with animals of similar age and weight from the same vendor.

Animal Husbandry

All animals are housed (group or individual) in compliance with USDA guidelines. The animal room environment is controlled, with targeted conditions: Temperature 18° C. to 26° C., relative humidity 30% to 70%, 12 hours artificial light and 12 hours dark. Temperatures and relative humidity are monitored daily.

All animals have access to Harlan Teklad Rodent Diet®, ad libitum, or any other acceptable Lab Chow, checked daily and added or replaced as needed. Feeders are designed to reduce soiling, bridging and scattering. Water is provided to the animals ad libitum.

Sensitization Regimen: Mice are sensitized by an intraperitoneal injection of 10 µg ovalbumin (OVA) mixed in 4 mg aluminum hydroxide Al(OH)$_3$ gel suspension in 0.2 ml sterile saline on Days 0, 7 and 14. This suspension is prepared one hour before intraperitoneal injection into each mouse. The animals are ready for OVA challenge on Day 21.

Antigen Challenge: Animals are exposed to aerosolized OVA on day 21 (5% w/v in sterile saline) for 20 minutes. The aerosol is generated by a PARI-Master nebulizer, the outlet of which is, connected to a small Plexiglas® chamber containing the animals. Bronchoalveolar lavage is performed on Day 22.

Method of Study Performance: On day 24, 72 hours following aerosol OVA exposure, a separate group of animals are anesthetized with urethane (0.15–0.2 gm/kg) and the trachea is exposed and cannulated. Lungs are lavaged with 2×0.5 ml Hank's balanced salt solution without $Ca^{2+}$ and $Mg^{2+}$ (HBSS; Gibco, Grand Island, N.Y.) containing 0.1% EDTA. Lavage fluid is recovered after 30 sec by gentle aspiration and pooled for each animal. Samples are centrifuged at 2000 rpm for 15 minutes at 5° C. After centrifugation, individual supernatants are stored frozen at −80° C. The resulting pellet is resuspended in 0.5 ml of HBSS containing 0.1% EDTA. Total cells and eosinophils are determined using a Technicon Hl and cytoslides, respectively.

Administration of the Test/Control Article: The test article and vehicle dosing preparations are administered once to each anesthetized mouse intranasally using a 200 µl pipette at 30–60 minutes prior to OVA challenge. Each animal receives 50 µl (25 µl/nostril) at each time point. Method of Euthanasia: Urethane overdose at in-life completion.

Statistical Analysis: Total cell and eosinophil number from various treatment groups is compared using an ANOVA followed by a multiple comparison test.

Results of mouse experiments are presented in Table 8. Compounds administered 30 minutes before aerosol ovalbumin challenge in ova sensitized mice. BALF harvested 24 hours after aerosol challenge. N=6/ group. 3-(4-pyridinylamino)-1H-indole-2-carboxylic acid inhibited both IL-4 and IL-13 levels in the BALF significantly in a dose dependent manner.

TABLE 8

In vivo Allergen-induced Lung Inflammation in the Mouse. Effect of 3-(4-pyridinylamino)-1H-indole-2-carboxylic acid (Example 28) on Bronchoalveolar Lavage Fluid (BALF) Cytokines

| Compound | Dose (mg/kg) (intranasal) | IL-4 pg/ml (± SEM) | IL-13 pg/ml (± SEM) |
|---|---|---|---|
| Vehicle | — | 1220.4 ± 207.7 | 120.2 ± 19.8 |
| Cyclosporin A | 30 | 144.4 ± 35.7 | 15.9 ± 2.4 |
| Example 28 | 30 | 123.9 ± 48.7 | 15.1 ± 7.1 |
| Example 28 | 10 | 414.3 ± 115.5 | 59.9 ± 12.7 |
| Example 28 | 3 | 835.1 ± 40.4 | ND | pg = picogram;
ND - not determined

FIG. 1 summarizes results from one representative experiment (out of three) in which in addition to BALF cytokines, lung eosinophilia is also determined. Mice (12 animals per group) are sensitized with 0.2 ml of an $AlOH_3$ hydrogel suspension (2% $AlOH_3$) containing 50 μg/ml ovalbumin on days 0, 7 and 14. On day 21, mice are dosed with various dose levels of 3-(4-pyridinylamino)-1H-indole-2-carboxylic acid (Example 28); 3, 10 & 30 mg/kg, 30 min prior to a 20 min challenge with 5% ovalbumin (OVA). The glucocorticosteroid budesonide (10 mg/kg) is included as a control. All compounds are given in 0.5% methylcellulose/0.2% Tween 80, intranasally (50 μl). After the OVA challenge for 24 hours, the mice underwent bronchoalveolar lavage and IL-4 and IL-13 levels in the BALF are determined by ELISA. Another group of mice underwent bronchoalveolar lavage (72 hours after treatment) to determine the number of the eosinophils (*p<0.05, **p<0.01). As shown in FIG. 1, 3-(4-pyridinylamino)-1H-indole-2-carboxylic acid (Example 28) significantly inhibited allergen-induced IL-4 and IL-13 levels in the BALF, with $ED_{50}$ values of approximately 10 mg/kg for each cytokine. Although 3-(4-pyridinylamino)-1H-indole-2-carboxylic acid is a relatively poor inhibitor of IL-13 in vitro, 3-(4-pyridinylamino)-1H-indole-2-carboxylic acid inhibited IL-13 almost as well as IL-4 in vivo.

Table 9 summarizes effects of 3-(4-pyridinylamino)-1H-indole-2-carboxylic acid (Example 28) and various other compounds of this invention on the OVA-induced IL-4 and eosinophilia in BALF. Compounds are given (30 mg/kg), intranasally, once, 30 min before OVA challenge unless noted otherwise. BAL fluids are collected 24 hours after OVA challenge and the cytokine levels are measured by standard ELISAs. From a parallel set of animals, BAL are collected at 48 hours and the number of eosinophils are determined. Various salts of 3-(4-pyridinylamino)-1H-indole-2-carboxylic acid including the maleate salt, methanesulfonic acid salt (EF, Exp.# 146) and potassium salt (ZD, Exp.# 146) are tested as summarized in Table 9.

TABLE 9

In vivo allergen-induced lung inflammation in the mouse: Summary of in vivo effects of different salts and analogs of 3-(4-pyridinylamino)-1H-indole-2-carboxylic acid (Example 28)

| Exp # | Compound # | Route | Dose (mg/kg) | IL-4 % ctl At 24 hours | Eos % ctl At 72 hours |
|---|---|---|---|---|---|
| 109 | Example 24A (maleate salt) | i.n. | 30 | 3 | 8 |
| 130 | Example 24A (maleate salt) | i.p. | 12 | 50 | |
| 140 | Example 28 (maleate salt) | i.n. | 12 | 50 | Not done |
| 146 | Example 28 (maleate salt) | i.n. | 10 | 57 | 53 |
| 146 | Example 28 (maleate salt) | i.n. | 30 | 34 | 28 |
| 146 | Example 28-EF | i.n. | 30 | 27 | 42 |
| 146 | Example 28-ZD | i.n. | 30 | 49.6 | 37.4 |
| 115 | Example 28 (maleate salt) | i.p. | 30 | 43 | Not done |
| 109 | Example 90 | i.n. | 30 | 37 | 71 | i.n. = intranasal;
i.p. = intraperitoneal; and
p.o. = per os (by mouth)

Table 10 summarizes effects of 3-(4-pyridinylamino)-1H-indole-2-carboxylic acid on OVA induced IgE in mice. Female mice (5–8 week age, Balb/c Charles River) were used in this study. Ovalbumin (Sigma) was adsorbed to Aluminum Hydroxide Adsorptive Gel, Inter, and injected 10 μg/0.2 ml/mouse intraperitoneally on experimental day 0 and day 7. Dexamethasone (Sigma) and 3-(4-pyridinylamino)-1H-indole-2-carboxylic acid (Example 28) were in 10% HPCD (Hydroxypropyl-β-Cyclodextrin, Aldrich). Dexamethasone (10 mg/kg), 3-(4-pyridinylamino)-1H-indole-2-carboxylic acid (Example 28) (3 and 10 mg/kg) and 10% HPCD (0.2 ml/mouse) are injected into mice intraperitoneally once a day from day 6 to day 14. They were bled at day 15. Serum ovalbumin specific IgE levels were determined by standard ELISA using a goat anti-mouse IgE antibody labeled with alkaline phosphatase. The anti-OVA titers were determined by making serial dilutions of the test sera and comparing with vehicle control.

TABLE 10

Inhibition of allergen specific IgE antibody by 3-(4-pyridinylamino)-1H-indole-2-carboxylic acid (Example 28) in mice

| Treatment | Anti-OVA IgE | SE |
|---|---|---|
| Vehicle | 150.8 | 52.9 |
| Dexamethasone | 27.4 | 9.4 |
| Example 28 (3 mg/kg) | 41.8 | 8.5 |
| Example 28 (10 mg/kg) | 45.6 | 15.7 |

The effect of 3-(4-pyridinylamino)-1H-indole-2-carboxylic acid on OVA-induced lung inflammation was also studied in rats. Rat model was very similar to the mouse models described earlier. Briefly, the lung inflammatory model described by Haczku et al. was used with minor modifications (Haczku A., et al., *Immunology*, (1996), 88, 247–251). Male Brown Norway rats, weighing 160–200 grams were sensitized with intraperitoneal injection of 1 ml of a suspension containing ovalbumin (1 mg) and Al(OH)$_3$ (100 mg) on days 1, 2 and 3. Three weeks later, the rats were treated with vehicle or drugs via intraperitoneal injections. One hour later, the rats were challenged with ovalbumin inhalation (1% solution, 10 mg/ml in sterilized saline) for 20 minutes in a 10 liter Plexiglas chamber which was connected to a DeVilbiss (Ultra-NEB®99) nebulizer with a carrier air flow of 1 liter/minute.

Figure 2:
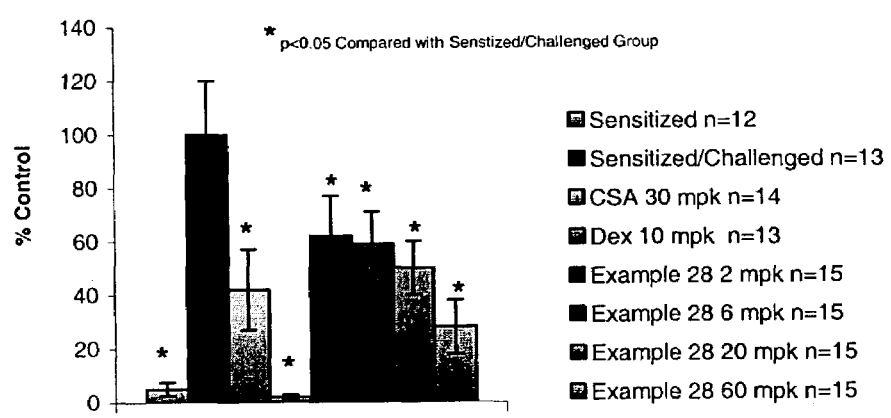
FIG. 2 is a bar graph depicting the inhibition by 3-(4-pyridinylamino)-1H-indole-2-carboxylic acid (Example 28) of allergen-induced lung inflammation in the rat.

Results of dose response studies of 3-(4-pyridinylamino)-1H-indole-2-carboxylic acid on eosinophil influx into the bronchoalveolar fluid of ovalbumin sensitized and challenged Brown Norway rats are depicted as bar graphs in FIG. 2. Single dose of cyclosporin A (CsA) and dexamethasone (Dex) were also included as reference standards. 3-(4-pyridinylamino)-1H-indole-2-carboxylic acid, administered with intraperitoneal injection, inhibited the influx of eosinophil in a dose dependent fashion with ED$_{50}$ of 10.07 mg/kg.

An in vivo model of humoral immunity in mice

The purpose of this assay was to determine if IL-4 inhibitors had an effect on normal antibody response, which is known to be dependent on T helper cells that regulate B cells to make antibody. This model demonstrates the effect of 3-(4-pyridinylamino)-1H-indole-2-carboxylic acid on its general immunosuppressive activities in mice.

Female Balb/c mice, each weighing approximately 20 to 25 grams each, aged 5 to 8 weeks are used. Each experiment uses 30 mice.

Immunization of Mice

The antigen for immunization is 2,4-dinitrophenyl (DNP) or 2,4,6-trinitrophenyl (TNP) conjugated to keyhole limpet haemocyanin (KLH). The antigen (100 µg/mouse) is adsorbed to an adjuvant (colloidal aluminum hydroxide) and given i.p. to animal in a total volume of 0.2–0.3 ml. The method described herein for production of immune response is similar to the methods used by other investigators (see, for example, Wilder, J. A., et al., J. Immunol., (1996), 156, 146–152; and Leenaars et al., Immunology, (1997), 90, 337–343.

Protocol and Compound Treatment

Animals are randomly divided into 5 groups of 6 mice each. Group 1 is a positive control group, Groups 2, 3, and 4 are test compound groups, and Group 5 is a vehicle control group. Compounds may be given by i.n., i.p., p.o., s.c., i.m. or i.v. administration. Generally, compounds of this invention are administered daily to mice, starting one to two days prior to immunization until 7 days after immunization (9–10 times). On day 8 after the immunization, mice are bled by cardiac puncture under anesthesia (isoflurane), and the serum samples are stored at −20° C. until required for antibody analysis. The anesthetized animals are euthanized with overdosage of sodium pentobarbital at the end of experiment. Statistical analysis of the data are performed using ANOVA.

Results presented in Table 11 demonstrate Th2 cytokine selectivity of 3-(4-pyridinylamino)-1H-indole-2-carboxylic acid in vivo. Mice are immunized with a hapten carrier conjugate, DNP-KLH, and anti-DNP antibody levels are determined in a isotype specific manner as described above. Treatment with 3-(4-pyridinylamino)-1H-indole-2-carboxylic acid caused a marked reduction of IgG1 anti-DNP antibody levels (partially Th2, IL-4-dependent) but had no significant effect on IgG2a antibody level (Th1, IFN-γ dependent). CsA used as control, at 10 mg/kg in this study, completely inhibited both IgG2a and IgG1 antibodies.

TABLE 11

Differential effect of 3-(4-pyridinylamino)-1H-indole-2-carboxylic acid (Example 28) on different isotypes of anti-hapten antibodies

| Animal # | IgG2a Anti-DNP Antibody Titer | | IgG1 Anti-DNP Antibody Titer | |
|---|---|---|---|---|
| | Vehicle | Example 28 | Vehicle | Example 28 |
| 1 | 31.40 | 30.59 | 123.14 | 72.42 |
| 2 | 30.64 | 38.60 | 149.30 | 185.22 |
| 3 | 38.46 | 14.09 | 205.93 | 19.83 |
| 4 | 24.21 | 17.45 | 236.97 | 40.19 |
| 5 | 27.64 | 30.21 | 158.70 | 83.11 |
| 6 | — | 27.98 | 132.12 | 37.83 |
| Mean +/− SE | 30.47 +/− 2.37 | 26.49 +/− 3.72 | 167.69 +/− 18.19 | 73.10 +/− 24.38 |
| Inhibition | — | 13% | — | 56.5% |

Sheep Asthma Model

The following in vivo model demonstrates that a compound capable of modulating a Th2 cytokine, specifically IL-4, is also capable of improving pulmonary function and reducing pulmonary resistance in vivo. The following pulmonary function studies are performed in sheep allergic to Ascaris suum, as previously described by Abraham (Abraham, W. M., "Sheep Models of Allergic Bronchoconstriction" in "Allergy and Allergic Diseases," Kay, A. B., Ed. Blackwell Science—Oxford, (1997), 1045–1055). The sheep used in this study had previously demonstrated early and late airway responses and airway hyper responsiveness to carbachol following inhalation challenge with Ascaris suum extract. Briefly, transpulmonary pressure, pulmonary resistance ($R_L$), specific lung resistance ($SR_L$) airway hyper reactivity, airway responsiveness, are determined.

Methods

Animal Preparation: All animals demonstrated both early and late airway responses to inhalation challenge with Ascaris suum antigen. Venous blood samples (~5 ml) are obtained from a peripheral leg vein or the jugular vein for pharmacokinetic data. Measurement of Airway Mechanics: The unsedated sheep are restrained in a cart in the prone position with their heads immobilized. After topical anesthesia of the nasal passages with 2% lidocaine solution, a balloon catheter is advanced through one nostril into the lower esophagus. The animals are incubated with a cuffed endotracheal tube through the other nostril using a flexible fiberoptic bronchoscope as a guide. (The cuff of the endotracheal tube is inflated only for the measurement of airway mechanics and during aerosol challenges to prevent undue discomfort. This procedure has no effect on airway mechanics). Pleural pressure is estimated with the esophageal balloon catheter (filled with one ml of air) which is positioned 5–10 cm from the gastroesophageal junction. In this position the end expiratory pleural pressure ranges between −2 and −5 cm $H_2O$. Once the balloon is placed, it is secured so that it remains in position for the duration of the experiment. Lateral pressure in the trachea is measured with a sidehole catheter (inner dimension, 2.5 mm) advanced through and positioned distal to the tip of the endotracheal tube. Transpulmonary pressure, the difference between tracheal and pleural pressure, is measured with a differential pressure transducer catheter system. For the measurement of pulmonary resistance ($R_L$), the proximal end of the endotracheal tube is connected to a pneumotachograph (Fleisch, Dyna Sciences, Blue Bell, Pa.). The signals of flow and transpulmonary pressure is recorded on an oscilloscope recorder which is linked to a computer for on-line calculation of $R_L$ from transpulmonary pressure, respiratory volume (obtained by digital integration) and flow. Analysis of 5–10 breaths is used for the determination of $R_L$. Immediately after the measurement of $R_L$, thoracic gas volume ($V_{tg}$) is measured in a constant volume body plethysmograph to obtain specific lung resistance ($SR_L = R_L \cdot V_{tg}$) in L×cm $H_2O$/LPS.

Aerosol Delivery Systems: Aerosols of *Ascaris* suum extract (diluted 20:1 with phosphate buffered saline; 82,000 PNU/ml) are generated using a disposable medical nebulizer (Raindrop$^R$, Puritan Bennett), which produces an aerosol with a mass median aerodynamic diameter of 3.2 µm (geometric standard deviation, 1.9) as determined by a 7 stage Andersen cascade impactor. The output from the nebulizer is directed into a plastic t-piece, one end of which is connected to the inspiratory port of a Harvard respirator. To better control aerosol delivery, a dosimeter consisting of a solenoid valve and a source of compressed air (20 psi) is activated at the beginning of the inspiratory cycle of the Harvard respirator system for 1 s. The aerosol is delivered at a tidal volume of 500 ml and a rate of 20 breaths per minute for 20 minutes. Each sheep is challenged with an equivalent dose of antigen (400 breaths) in the control and drug trial. Carbachol aerosols are also generated with the nebulizer system described above.

Dose Response Curves to Inhaled Carbachol: For the carbachol dose response curves, measurements of $SR_L$ is repeated immediately after inhalation of buffer and after each administration of 10 breaths of increasing concentrations of carbachol solution (0.25%, 0.5%, 1.0%, 2.0% and 4.0% w/v). To assess airway responsiveness, the cumulative carbachol dose in breath units (BU) that increases $SR_L$ 400% over the post-buffer value (i.e. $PC_{400}$) is calculated from the dose response curve. One breath unit is defined as one breath of a 1% w/v carbachol solution.

Experimental Protocol

Baseline dose response curves to aerosol carbachol are obtained 1–3 days prior to antigen challenge. On occasions at least 2 weeks apart baseline values of specific lung resistance ($SR_L$) are obtained and then the sheep are administered saline (control) or drug (at doses of 3 mg of test compound, 3-(4-pyridinylamino)-1H-indole-2-carboxylic acid (Example 28), in NaOH/saline) 30 min before antigen challenge. For these studies the compound, 3-(4-pyridinylamino)-1H-indole-2-carboxylic acid (Example 28), is administered by aerosol. Then the sheep are challenged with *Ascaris suum* antigen. Measurements of $SR_L$ are obtained immediately after challenge, hourly from 1–6 h after challenge and on the half-hour from 6½–8 h after challenge. Measurements of $SR_L$ are obtained 24 h after antigen challenge followed by the 24 h post challenge carbachol dose response curve. For the initial studies, drug trials are compared to the animal's historical control data.

For the evaluation of 3-(4-pyridinylamino)-1H-indole-2-carboxylic acid (Example 28) baseline values of $SR_L$ are obtained and then the sheep are administered either vehicle or drug (3 mg/kg) as an aerosol in PEG400 vehicle. $SR_L$ is remeasured and 30 minutes after dosing animals are challenged by aerosol with *Ascaris suum* antigen. Measurements of $SR_L$ are obtained immediately after challenge, hourly from 1 to 6 hours after challenge, and on the half-hour from 6.5 to 8 hours after challenge.

Figure 3A:
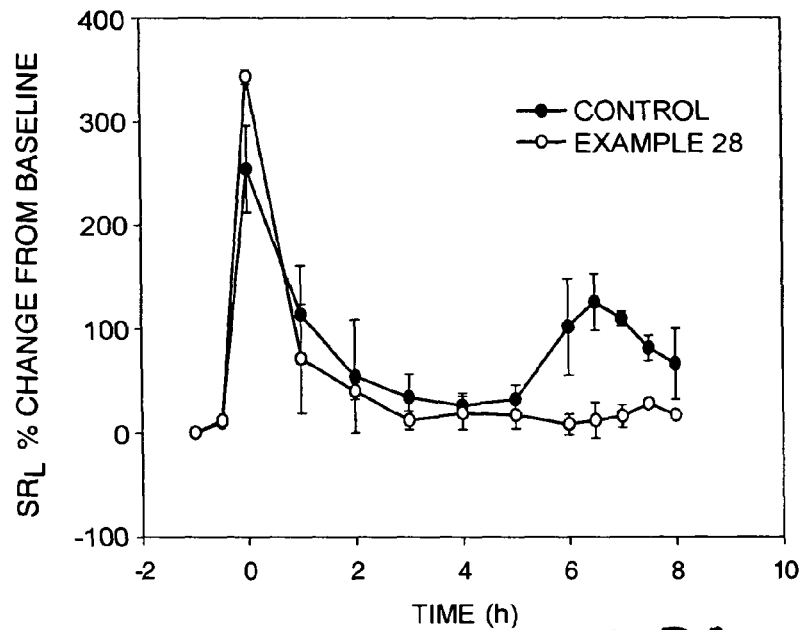
FIG. 3A is a graph depicting the effect of 3-(4-pyridinylamino)-1H-indole-2-carboxylic acid (Example 28) on antigen-induced early and late bronchial responses.

The results presented in FIG. 3 represent the mean±sem from 2 sheep per group. FIG. 3A depicts the effect of 3-(4-pyridinylamino)-1H-indole-2-carboxylic acid (Example 28) on antigen-induced early and late bronchial responses. 3-(4-pyridinylamino)-1H-indole-2-carboxylic acid (Example 28) (3 mg/kg) is given 30 min before antigen challenge as an aerosol. It did not affect the acute increase in specific lung resistance ($SR_L$) but blocked the late response compared to control.

Figure 3B:
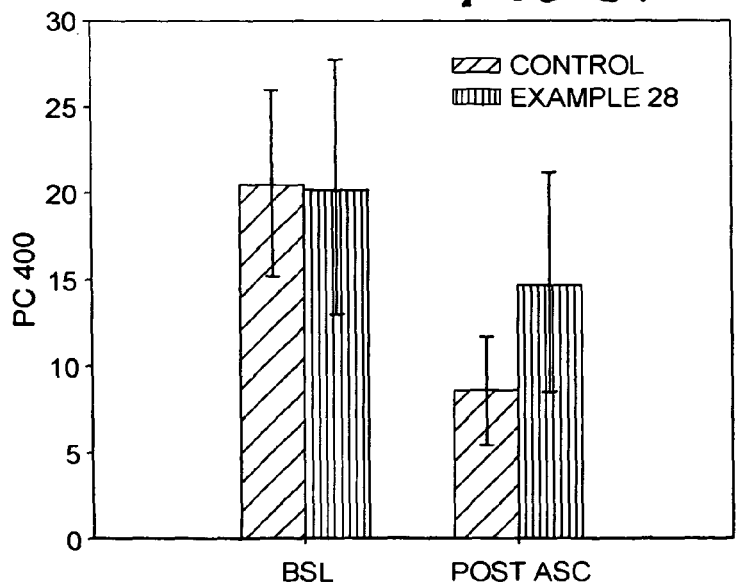
FIG. 3B is a bar graph depicting the effect of 3-(4-pyridinylamino)-1H-indole-2-carboxylic acid (Example 28) (3 mg/kg) on post challenge airway responsiveness.

FIG. 3B depicts the effect of 3-(4-pyridinylamino)-1H-indole-2-carboxylic acid (Example 28) (3 mg/kg) on post challenge airway responsiveness. In the control trial, $PC_{400}$ (the amount of carbachol that causes a 400% increase in $SR_L$) decreased after antigen challenge (i.e., the sheep became hyper responsive). Treatment with 3-(4-pyridinylamino)-1H-indole-2-carboxylic acid (Example 28) prevented this effect. All values are mean±SE for 2 sheep. Responses are compared to historical control values (control) and vehicle controls.

This invention is further illustrated by the following examples which are provided for illustration purposes and in no way limit the scope of the present invention.

EXAMPLES (GENERAL)

General Analytical Techniques Used for the Characterization: A variety of analytical techniques were used to characterize the compounds used in the method of this invention, which included the following:

The phrase "concentrated in vacuo or rotary evaporated" indicates rotary evaporation using a Buchi apparatus at 20–60° C. and 15–30 torr using a KNF Neuberger diaphragm pump. Room temperature is abbreviated as "rt".

Preparative reversed phase HPLC was carried out on a Rainin SD1 unit using a Dynamax $C_{18}$ column (60 A spherical 13 µm particles). The mobile phase consisted of acetonitrile/buffer mixtures, with buffer composed of distilled water, acetonitrile, and trifluoroacetic acid (TFA) in the ratio listed in the experimental procedures.

$^1$H NMR spectra were recorded on a Varian Gemini 300, Unity 300, Unity 400, or Unity 500 spectrometers with chemical shifts (δ) reported in ppm relative to tetramethylsilane (0.00 ppm) or chloroform (7.26 ppm) as a reference. Signals were designated as s (singlet), d (doublet), t (triplet), q (quartet), p (pentuplet), m (multiplet), br (broad).

Chromatographic (flash) purifications on silica gel were done using pre-packed Isco or Biotage cartridges (32–63 μm, 60 A).

Mass spectra (MS) were obtained on a Finnigan MAT Model TSQ 700 Mass Spectrometer System by chemical ionization at 120 eV using methane (CI, 120 eV). The protonated molecular ion designated as (M++1) is given in parentheses.

Liquid chromatography with mass spectral analysis (LC/MS): HPLC: column: 50×4.6 mm, Hypersil BDS C18 3u. Mobile Phase: A=water with 0.05% trifluoroacetic acid, B=acetonitrile with 0.05% trifluoroacetic acid, flow rate=1.0 ml/min, gradient=5% B to 100% B in 3 min, stay 100% for 2 min. Mass Spectrometry: Lct API LC/Orthogonal Time of Flight Mass Spectrometer and Masslynx Data System from Micromass. Ionization mode=electrospray (ESI), Source temperature=120° C., Desolvation temperature=250° C., Cone voltage=25 volt, Acquisition mass range m/z from 145 to 1000. Values were determined for the protonated molecular ions (M++1).

Example 1

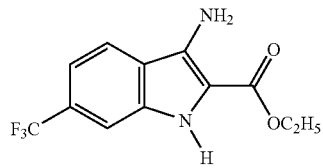

Scheme A

Step A1: 3-Amino-6-trifluoromethyl-1H-indole-2-carboxylic acid, ethyl ester

Under nitrogen, stir and heat a mixture of 2-fluoro-4-(trifluoromethyl)benzonitrile (1.0 g, 5.29 mmol), ethyl glycinate hydrochloride (886 mg, 6.3 mmol), potassium carbonate (1.46 g, 6.3 mmol) and 1-methyl-2-pyrrolidinone (20 mL) at 115–120° C. After six hours add potassium tert-butoxide (700 mg, 6.2 mmol), and stir at ambient temperature for 2 h. Quench into ice/water, extract the aqueous mixture with ether, wash the extract with water and dry it with magnesium sulfate. Filter and concentrate under vacuum to yield the crude product. Chromatograph the crude product on silica gel (10 g, Sepack cartridge) with dichloromethane as eluent to afford 332 mg (23%) of the title compound. Identical on TLC (silica gel, dichloromethane) to the compound disclosed in U.S. Pat. No. 5,189,054.

Example 2

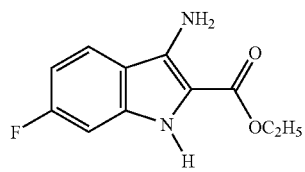

Scheme A

Step A1: 3-Amino-6-fluoro-1H-indole-2-carboxylic acid, ethyl ester

Under nitrogen, stir and heat a mixture of 2,4-difluorobenzonitrile (1.14 g, 8.2 mmol), ethyl glycinate hydrochloride (1.5 mg, 10.7 mmol), potassium carbonate (3.4 g, 24.6 mmol) and 1-methyl-2-pyrrolidinone (20 mL). After 2 h allow the reaction to cool to 40° C. and add potassium tert-butoxide (300 mg, 2.7 mmol). Allow the reaction to stir and for 1 h and then add additional potassium tert-butoxide (500 mg, 4.4 mmol). Cool to room temperature overnight, pour the reaction mixture onto ice. Add water to dissolve the solids in the reaction flask and add to the reaction quench. Filter off the precipitated brown solid and extract the filtrate with ethyl acetate. Wash the extract with water (2×'s), brine and dry over magnesium sulfate. Filter and concentrate under vacuum to give a residue, which is triturated with dichloromethane to afford a solid. Collect the solid, concentrate the filtrate and chromatograph the solid on silica gel (10 g, Sepack cartridge) with dichloromethane as the eluent. Collect the appropriate fractions and concentrate to obtain a solid. Combine with the previously collected solid to provide 136.7 mg (7.5%) of the title compound: MS 223(M+H).

Example 3

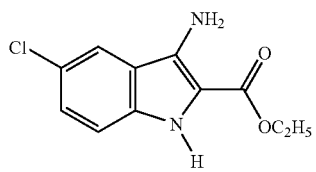

Scheme B:
3-Amino-5-chloro-1H-indole-2-carboxylic acid, ethyl ester

Step B 1: 2-Amino-N-tert-butyl-5-chlorobenzamide

Stir and cool to 0° C. a solution of 2-amino-5-chlorobenzoic acid (1.21 g, 10 mmol) and N-hydroxysuccinimide (1.38 g, 12 mmol) in dichloromethane (12 mL). Add, dropwise, a 1M solution of dicyclohexylcarbodiimide in dichloromethane (12 mL, 12 mmol), and stir at 0° C. for 1 h. Add tert-butyl amine (1.74 g, 23.79 mmol) by syringe and stir at ambient temperature overnight. Filter the reaction mixture and wash the filtrate with aqueous sodium bicarbonate. Dry the organic phase with MgSO$_4$ and chromatograph over silica gel eluting with 4% ethyl acetate/dichloromethane to afford 1.74 g of the title compound: MS 227(M+H), m.p. 126–127° C.

Step B2: N-(4-Chloro-2-cyanophenyl)-2,2,2-trifluoroacetamide

Stir and cool to 0° C. a solution 2-amino-N-tert-butyl-5-chlorobenzamide (5.07 g, 22.36 mmol) in dichloromethane (200 mL), and add, dropwise trifluoroacetic anhydride. Stir at ambient temperature overnight and concentrate under reduced pressure. Partition between chloroform and aqueous sodium bicarbonate, and collect the organic layer. Dry the extract with MgSO$_4$, filter and evaporate the solvent. Triturate the residue with heptane and collect the white solid to obtain 4.80 g (82%) of the title compound: MS 249(M+H), m.p. 105–107° C.

Step B3: ((4-Chloro-2-cyanophenyl)-(2,2,2-trifluoro-ethanoyl)amino)-acetic acid ethyl ester Under nitrogen, stir and cool to 0° C. a solution of N-(4-chloro-2-cyano-phenyl)-2,2,2-trifluoroacetamide (4.80 g, 19.31 mmol) in dimethylformamide (50 mL), and add NaH (0.7 g, 29.1 mmol). Stir the reaction for 1 h at ambient temperature and add ethyl bromoacetate (4.3 mL, 38.77 mmol) by means of a syringe. Stir at 50° C. overnight and then pour the reaction into aqueous ammonium chloride-ethyl acetate. Wash the organic layer with brine (2×'s), dry over $MgSO_4$, filter and evaporate to obtain an oil. Chromatograph the oil eluting with 20% ethyl acetate/heptane and then 30% ethyl acetate/heptane. Concentrate the appropriate fractions and obtain 6.0 g of a solid MS 335(M+H), m.p. 71–73° C.

Step B4: 3-Amino-5-chloro-1-(2,2,2-trifluoro-ethanoyl)-1H-indole-2-carboxylic acid ethyl ester Under nitrogen, stir and cool to 0° C. a solution [(4-chloro-2-cyanophenyl)-(2,2,2-trifluoro-ethanoyl)amino]-acetic acid ethyl ester (93.34 g, 10 mmol) in tetrahydrofuran (20 mL) and add, dropwise, a 1M solution of potassium tert-butoxide in tetrahydrofuran (12 mL, 12 mmol). Stir the reaction at ambient temperature for 2 h and then partition between aqueous ammonium chloride/ethyl acetate. Separate the organic layer, dry over $MgSO_4$, filter and concentrate to a solid. Triturate the solid with heptane, filter the solid and air dry to obtain 2.86 g (86%) of the title compound: MS 335(M+H), m.p. 249–251° C.

Step B5: 3-Amino-5-chloro-1H-indole-2-carboxylic acid, ethyl ester

Heat at 70° C. and stir a mixture of 3-amino-5-chloro-1-(2,2,2-trifluoro-ethanoyl)-1H-indole-2-carboxylic acid ethyl ester (3.34 g, 10 mmol), ethanol (50 mL), and potassium carbonate (1.50 g, 10.85 mmol). After 1.75 h, add water (20 mL), and after another hour add additional potassium carbonate (0.58 g, 4.20 mmol). Cool the reaction mixture to ambient temperature and partition between water/ethyl acetate. Separate the organic layer, dry over $MgSO_4$, filter and concentrate to afford 1.70 g of the title compound as a solid. MS 239(M+H).

Example 4

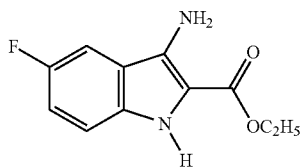

Scheme B:
3-Amino-5-fluoro-1H-indole-2-carboxylic acid, ethyl ester

Step B 1: 2-Amino-N-tert-butyl-5-fluorobenzamide

Stir and cool to 0° C. a solution of 2-amino-5-fluorobenzoic acid (7.75 g, 50 mmol), N-hydroxysuccinimide (6.9 g, 60 mmol) and dimethylaminopyridine (1.0 g) in dichloromethane (200 mL). Add, dropwise, a 1M solution of dicyclohexylcarbodiimide in dichloromethane (60 mL, 60 mmol), and stir at 0° C. for 1H. Add tert-butyl amine (20 mL, 190.3 mmol) by syringe and stir at 0° C. for 3 h and then at ambient temperature overnight. Pour onto a pad of silica gel and elute with 5% ethyl acetate/dichloromethane. Combine like fractions and concentrate to obtain a crude solid. Triturate the solid with heptane and filter to obtain 7.7 g (73%) of the title compound: MS 211(M+H), m.p. 77–78° C.

Steps B2-B5: 3-Amino-5-fluoro-1H-indole-2-carboxylic acid, ethyl ester

Follow the procedure of Example 3 (Steps B2-B5) to obtain 3-amino-5-fluoro-1H-indole-2-carboxylic acid, ethyl ester: MS 223(M+H), TLC (silica gel, 4% ethyl acetate/dichloromethane) $R_f$=0.50.

Example 5

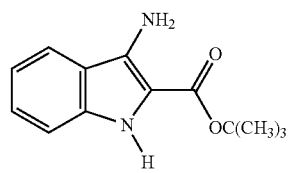

Scheme B

Steps B3–B5: 3-Amino-1H-indole-2-carboxylic acid, tert-butyl ester

Follow the procedure of Example 3 (Steps B3–B5) but start with N-(2-cyano-phenyl)-2,2,2-trifluoroacetamide (synthesis described in J. Fluorine Chem. 1981, 18, (2), 185–95) and tert-butyl bromoacetate to obtain the title compound: MS 310(M+H), TLC (silica gel, dichloromethane/methanol, 7:1) $R_f$=0.38.

Example 6

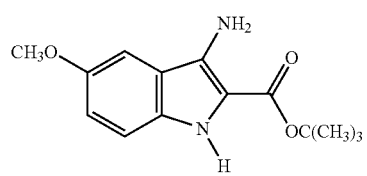

Scheme B

Steps B1–B5: 3-Amino-5-methoxy-1H-indole-2-carboxylic acid, tert-butyl ester

Follow the procedure of Example 3 but start with 2-amino-5-methoxy benzoic acid, and in Step B3 use tert-butyl bromoacetate instead of ethyl bromoacetate to obtain the title compound: MS 263(M+H), m.p. 146–147° C.

Example 7

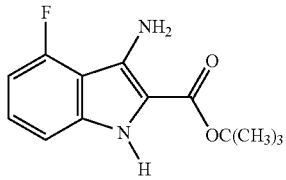

Scheme B

Steps B3-B5: 3-Amino-4-fluoro-1H-indole-2-carboxylic acid, tert-butyl ester

Follow the procedure of Example 5, but start with 3-fluoro-N-(2-cyano-phenyl)-2,2,2-trifluoroacetamide (synthesis described in J. Fluorine Chem. 1981, 18, (2), 185–95) and tert-butyl bromoacetate to obtain the title compound: MS 251(M+H), TLC (silica gel, dichloromethane/methanol, 7:1) $R_f$=0.38.

Example 8

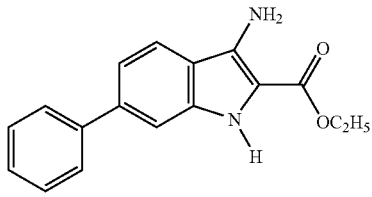

Scheme C:
3-Amino-6-phenyl-1H-indole-2-carboxylic acid, ethyl ester

Step C1: N-(5-Chloro-2-cyanophenyl)acetamide

Heat on a steam bath a mixture of 2-amino-4-chlorobenzonitrile (20.0 g, 131 mmol) and acetic anhydride (80 mL) for 40 min. Add water (300 mL) and stir for 1 h. Filter the resulting solid, wash it with water and dry it under vacuum at 40° C. to obtain 22.9 g of product. Recrystallize a 12.8 g sample from ethanol-ethyl acetate and obtain 9.83 g of the title compound: MS 195(M+H), TLC (silica gel, ethyl acetate/heptane1: 1:1) $R_f$=0.38.

Step C2: N-(2-cyanophenyl-5-phenyl)acetamide

Stir at ambient temperature a mixture of N-(5-Chloro-2-cyanophenyl)-acetamide (0.389 g, 2.0 mmol), phenylboronic acid (0.366 g, 3.0 mmol), palladium (II) acetate (8.8 mg), 2-(dicyclohexylphosphino)biphenyl (28.0 mg), potassium fluoride (0.348 g, 5.99 mmol) and tetrahydrofuran (5 mL) overnight. Pour the reaction mixture into an aqueous solution of potassium carbonate (30 mL) and extract with ethyl acetate (2×25 mL). Combine the extracts and wash with water and brine, dry over MgSO4 and concentrate under vacuum to obtain a tan solid. Triturate the solid with ether and collect 0.365 g (77%) of the title compound as an off-white powder: MS 237(M+H), m.p. 168–170° C.

Step C3: 3-Amino-1-(ethanoyl)-6-phenyl-1H-indole-2-carboxylic acid ethyl ester Cool to 4° C. a solution of N-(2cyanophenyl-5-phenyl) acetamide (15.0 g, 63.5 mmol), in 1-methyl-2-pyrrolidinone (150 mL) and add dropwise, a 1M solution of potassium tert-butoxide in tetrahydrofuran (77.0 mL, 77.0 mmol). Age the reaction at 0° C. for 30 min and then add ethyl bromoacetate (12.0 g, 72.1 mmol). Stir at room temperature overnight and quench the reaction into water (600 mL). Extract the aqueous mixture with ether (3×300 mL), combine the extracts, wash the extract with water and brine and dry over MgSO4. Filter and concentrate the extracts under vacuum to obtain 20.6 g of a dark oil. Chromatograph on a Waters Prep Pak silica gel cartridge (500 g) and elute with a step gradient of 5%, 10% and 20% respectively of ethyl acetate/dichloromethane. Concentrate fractions containing starting material and obtain a yellow solid. Triturate the solid with ether and filter to afford 2.61 g of a white solid. Combine the filtrate from above with fractions from the chromatography that contain product and concentrate to afford 16.2 g of a dark oil. Chromatograph the oil on a Waters Prep Pak silica gel cartridge and elute with a step gradient of 2%, 5% and 10% respectively of ethyl acetate/dichloromethane. Combine like fractions and concentrate to obtain 7.33 g of the title compound: MS 323(M+H), TLC (silica gel, 20% ethyl acetate/dichloromethane) $R_f$=0.67.

Step C4: 3-Amino-6-phenyl-1H-indole-2-carboxylic acid, ethyl ester

Reflux a mixture of 3-amino-1-(ethanoyl)-6-phenyl-1H-indole-2-carboxylic acid ethyl ester (7.3 g, 22.6 mmol) 20% aqueous potassium carbonate (100 mL) and ethanol (100 mL) for 1.75 h. Let the reaction stand at ambient temperature overnight and dilute with water (500 mL). Cool at 0° C. and collect a purple solid. Wash the solid with water and dry at 40° C. under vacuum and obtain 5.7 g of a purple solid. Triturate the solid with dichloromethane (40 mL) filter and wash the solid with dichloromethane and ethyl acetate, and then dry at 40° C. under vacuum to obtain 2.5 g of the title compound as a solid:
ESI/MS 281 (M+H), HPLC: $R_f$=1.83 min., m.p. 181–183° C.

Example 9

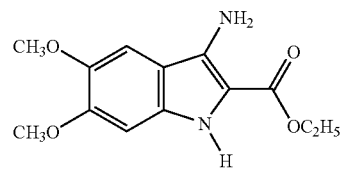

Scheme D:
3-Amino-5,6-dimethoxy-1H-indole-2-carboxylic acid, ethyl ester

Step D1: (2-Cyano-4,5-dimethoxy-phenylamino)-acetic acid ethyl ester

Under N2 suspend 2-amino-4,5-dimethoxybenzonitrile (2.0 g, 12.25 mmol) in ethanol (50 mL), and add sodium bicarbonate (3.09 g, 36.78 mmol) in one portion. By syringe, slowly add ethyl bromoacetate (2.72 mL, 24.5 mmol), and then sodium iodide (10 mg). Heat the reaction at 65° C. and then cool to ambient temperature. Filter the resulting solid and wash with ethyl acetate to dissolve the organics. Concentrate the filtrate to obtain 0.66 g (23%) of the title compound; MS 265(M+H).

Step D2: 3-Amino-5,6-dimethoxy-1H-indole-2-carboxylic acid, ethyl ester

Stir under $N_2$ a solution of (2-cyano-4,5-dimethoxy-phenylamino)-acetic acid ethyl ester (0.124 g, 0.47 mmol) in tetrahydrofuran (6 mL) and add, dropwise, 1M potassium tert-butoxide in tetrahydrofuran (0.66 mL, 0.66 mmol). Stir for 1 h at ambient temperature and pour into ice/water. Extract with ethyl acetate, dry the extract over $MgSO_4$, filter and concentrate under vacuum to a solid. Chromatograph on a Sep Pak silica gel cartridge (2 g) eluting with dichloromethane and then 2:1 heptane-ethyl acetate. Combine like fractions and concentrate to provide 61.9 mg (49%) of the title compound as a solid: MS 265(M+H).

Example 10

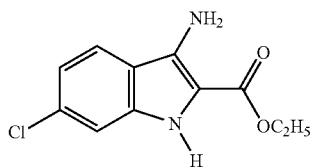

Scheme D:
3-Amino-6-chloro-1H-indole-2-carboxylic acid, ethyl ester

Step D4: 3-Amino-1-(ethanoyl)-6-chloro-1H-indole-2-carboxylic acid ethyl ester

Stir and cool to 0° C. a mixture of N-(5-chloro-2-cyanophenyl)acetamide (see Example 8, 1.0 g, 5.14 mmol) and THF (10 mL) and add potassium tert-butoxide (6.2 mL, of a 1M solution in THF) and stir at 0° C. for 30 min. Add bromoethyl acetate (0.6 mL) in one portion. Stir at room temperature for 2 h. Quench the reaction with water (40 mL) and stir with ethyl acetate. Separate the layers and reextract the aqueous with ethyl acetate. Combine the organic extracts and wash with water and brine. Dry over $MgSO_4$ and concentrate under reduced pressure to obtain a brown solid. Triturate the solid with ether and collect a beige solid. Chromatograph the solid on silica gel with 2% ethyl acetate/dichloromethane followed by 10% ethyl acetate/dichloromethane to obtain 0.65 g (45%) of the title compound as a beige solid: MS 281(M+H), HPLC: $R_t$=3.20 min., TLC (silica gel, 10% ethyl acetate/dichloromethane) $R_f$=0.53.

Step D5: 3-Amino-6-chloro-1H-indole-2-carboxylic acid, ethyl ester

Add 1N ethanolic potassium hydroxide solution (100 mL) to 3-amino-1-(ethanoyl)-6-chloro-1H-indole-2-carboxylic acid ethyl ester (3.5 g, 12.5 mmol) and permit the reaction to stand for 20 min. Pour the resulting slurry into water at 5° C. with rapid stirring. Age at 0° C. for 10 min., collect the solid, wash it with water dry it at 40° C. under vacuum and obtain 2.42 g (81%) of the title compound: MS 239(M+H).

Examples 11–21

Scheme E

Step E1:

Table 12 illustrates 3-(4-pyridinylamino)-1H-indole-2-carboxylic acid esters of the present invention, which can be synthesized similar to the method disclosed in U.S. Pat. No. 5,328,920. Accordingly, reaction of the appropriate 3-amino-indole-2-carboxylate with 4-chloropyridine hydrochloride in 1-methyl-2-pyrrolidinone produces the desired compounds. Changes of reaction times an temperatures from the referenced procedure are noted in the table. Table 13 lists the corresponding physical properties.

TABLE 12

Reaction Conditions

| Example | X | Y | Z | R | $R_2$ | Temp. ° C. | Time hours |
|---|---|---|---|---|---|---|---|
| 11 | H | H | NH | H | $C_2H_5$ | 165$^c$ | 6 |
| 12 | 6-$CF_3$ | H | NH | H | $C_2H_5$ | 80 | 18 |
| 13 | 6-Cl | H | NH | H | $C_2H_5$ | 100 | 5 |
| 14 | 5-Cl | H | NH | H | $C_2H_5$ | 100 | 4.5 |
| 15 | 6-F | H | NH | H | $C_2H_5$ | 80 | d |
| 16 | 5-F | H | NH | H | $C_2H_5$ | 100 | 2 |
| 17 | 4-F | H | NH | H | $C(CH_3)_3$ | 75 | 16 |
| 18 | 6-phenyl | H | NH | H | $C_2H_5$ | 100 | d |
| 19 | H | H | NH | H | $C(CH_3)_3$ | 100 | 2 |
| 20 | 5-$OCH_3$ | 6-$OCH_3$ | NH | H | $C_2H_5$ | 80 | 6 |
| 21 | 5-$OCH_3$ | H | NH | H | $C(CH_3)_3$ | 80 | 3.5 | d = overnight about 16–20 h

TABLE 13

Physical Properties

| Example | MS (M + H) | Retention Time Minutes (HPLC) | mp ° C. |
|---|---|---|---|
| 11 | 282 | | 248–250 |
| 12 | 350 | | |
| 13 | 316 | 1.90 | 258–261 (dec) |
| 14 | 316 | | |
| 15 | 300 | | |
| 16 | 300 | | |
| 17 | 328 | 1.58 | 210–212 |
| 18 | 358 | | 241–243 |
| 19 | 310 | | |
| 20 | 342 | 1.20 | |
| 21 | 340 | 1.13 | 217–219 |

Example 22

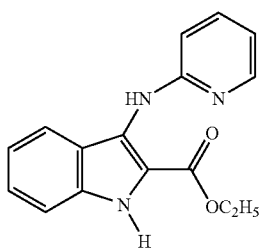

Scheme E

Step E1: 3-(2-Pyridinylamino)-1H-indole-2-carboxylic acid, ethyl ester

Heat a mixture of ethyl 3-aminoindole-2-carboxylate (250 mg, 1.2 mmol) and 2-bromopyridine (1.0 mL, 10 mmol) at 150° C. for 1 h. Cool the reaction and partition between aqueous ammonium chloride and ethyl acetate. Separate the organic layer and concentrate to afford a crude mixture. Flash chromatograph the mixture on silica gel eluting with 25% ethyl acetate/dichloromethane to afford 50 mg of the title compound: MS 282(M+H).

Example 23

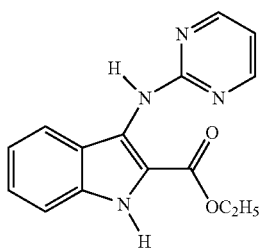

Scheme E

Step E1: 3-(Pyrimidin-2-ylamino)-1H-indole-2-carboxylic acid ethyl ester

Heat a mixture of ethyl 3-aminoindole-2-carboxylate (204 mg, 1.0 mmol) and 2-chloropyrimidine (1.2 g, 10.5 mmol) at 100° C. for 16 h. Cool the reaction and add aqueous ammonium chloride and ethyl acetate. Filter off excess 2-chloropyrimidine, separate the organic layer, dry with MgSO$_4$, filter and concentrate to afford a crude mixture. Flash chromatograph the mixture on silica gel eluting with 25% ethyl acetate/dichloromethane to afford 50 mg of the title compound: MS 283 (M+H), TLC (silica gel, 25% ethyl acetate/dichloromethane) R$_f$=0.44.

Example 24

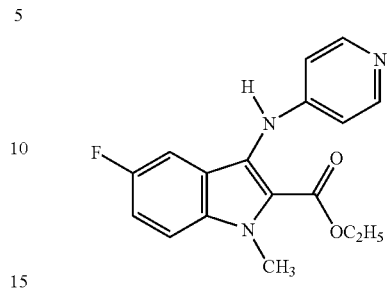

Scheme F

Step F8: 5-Fluoro-1-Methyl-3-(4-pyridinylamino)-1H-indole-2-carboxylic ethyl ester Stir at 0° C., a solution of 5-fluoro-3-(4-pyridinylamino)-1H-indole-2-carboxylic ethyl ester (0.195 mg, 0.65 mmol) in dimethylformamide (3.0 mL) and add a solution of 1M potassium tert-butoxide in tetrahydrofuran (0.8 mL, 0.8 mmol). Stir for 0.5 to 1 h at 0° C. and add Iodomethane (0.05 mL, 0.78 mmol). After 1 h, add saturated aqueous ammonium chloride solution (5 mL) and ethyl acetate (10 mL). Separate the layers and reextract with ethyl acetate. Combine the organic layers and wash with water (3×'s), brine and dry with MgSO$_4$. Concentrate the extract to obtain 60 mg (30%) of the title compound as a brown solid: ESI/MS 314 (M+H); HPLC: R$_t$=1.50 min.

Example 24A

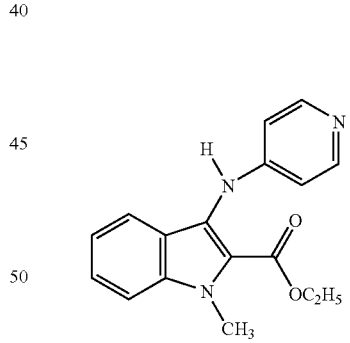

Scheme F

Step F8: 1-Methyl-3-(4-pyridinylamino)-1H-indole-2-carboxylic ethyl ester

The procedure of Example 24 is essentially repeated in this example except that the starting material used is 3-(4-pyridinylamino)-1H-indole-2-carboxylic ethyl ester. This compound is also described in the U.S. Pat. No. 5,328,920. The maleate salt of this compound exhibits a m.p. of 169°–170° C. (dec.).

Example 25

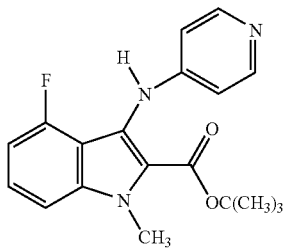

Scheme F

Step F8: 4-Fluoro-1-methyl-3-(4-pyridinylamino)-1H-indole-2-carboxylic tert-butyl ester Follow the procedure of Example 24 but start with 4-fluoro-3-(4-pyridinylamino)-1H-indole-2-carboxylic tert-butyl ester, but substitute tetrahydrofuran for dimethylformamide to obtain the title compound: ESI/MS 342 (M+H); HPLC: $R_t$=1.41 min.

Example 26

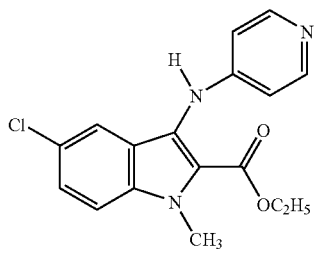

Scheme F

Step F8: 5-Chloro-1-methyl-3-(4-pyridinylamino)-1H-indole-2-carboxylic ethyl ester Follow the procedure of Example 24 starting with 5-chloro-3-(4-pyridinylamino)-1H-indole-2-carboxylic ethyl ester and obtain the title compound: ESI/MS 330 (M+H); HPLC: $R_t$=1.58 min.

Example 27

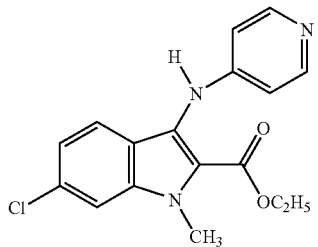

Scheme F

Step F8: 6-Chloro-1-methyl-3-(4-pyridinylamino)-1H-indole-2-carboxylic ethyl ester Follow the procedure of Example 24 starting with 6-chloro-3-(4-pyridinylamino)-1H-indole-2-carboxylic ethyl ester and obtain the title compound: ESI/MS 330 (M+H); HPLC: $R_t$=1.64 min, m.p.154–155° C.

Example 28

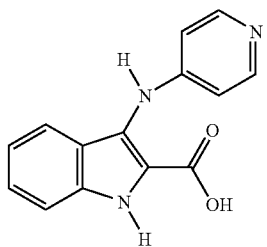

Scheme G:
3-(4-Pyridinylamino)-1H-indole-2-carboxylic acid

Step G1: (2-Cyanophenylamino)acetic acid ethyl ester

Charge a mixture of 10.0 kg (84.6 mol) of anthranilonitrile, 21.2 kg (127.0 mol, 1.5 equiv.) of ethyl bromoacetate, 12.0 kg (143.0 mol, 1.7 equiv.) of $NaHCO_3$, 10.0 g (catalytic) of sodium iodide and 33.0 L of ethanol to a 30-gal reactor. Heat the reaction mixture to and hold at 78–80° C. under nitrogen. Monitor the progress of the reaction by HPLC (Column—150×3.9 mm Waters Symmetry C18, 5 micron; mobile phase—60% acetonitrile/40% 0.1% TFA in water; flow rate—1.0 mL/min; wavelength—225 nm; $R_T$: anthranilonitrile—1.8 min (2-cyanophenylamino)acetic acid ethyl ester—2.7 min). Typically achieve, a 70–72% conversion in about 40–44 h. Allow the mixture to cool to 60° C. and filter warm to remove the inorganic solids. Wash the filter cake with 10.0 L of warm (70° C.) ethanol. Cool the filtrate to and hold at −20° C. for 4 h. Filter off the solid that formed and wash with 6.0 L of cold (−20° C.) ethanol and air dry to give 11.02 kg, 64.0% yield of the title compound: HPLC analysis 100% pure.

Step G2: 3-Amino-1H-indole-2-carboxylic acid ethyl ester

Charge a total of 30.0 L of tetrahydrofuran to a 30-gal reactor under nitrogen. Add a total of 4.0 kg (32.72 mol, 1.045 equiv.) of potassium tert-butoxide. Observe an exotherm to 25° C. from 20° C. Cool the mixture to 20° C. Dissolve a total of 6.40 kg (31.3 mol) of (2-cyanophenylamino)acetic acid ethyl ester in 30.0 L of tetrahydrofuran and add over 5 h at 20–25° C. Stir the reaction mixture at 20–23° C. for 18 h. Monitor the progress of the reaction by HPLC (Column—150×3.9 mm Waters Symmetry C18, 5 micron; mobile phase—60% acetonitrile/40% 0.1% TFA in water; flow rate—1.0 mL/min; wavelength—225 nm; $R_T$: 3-amino-1H-indole-2-carboxylic acid ethyl ester—1.5 min; (2-cyanophenylamino)acetic acid ethyl ester—2.7 min). Typically achieve, a 97% conversion. Concentrate the mixture at 30° C./50 torr to a solid residue. Add a total of 60.0 L of water to the residue and stir the mixture for 2 h at 23° C. Filter off the solid and wash with 60.0 L of water and air dry. Further dry the solid in a forced air oven at 55° C. for 24 h to give 4.45 kg, 69.5% yield, of the title compound: HPLC analysis 79.2% pure.

Step G3: 3-(4-Pyridinylamino)-1H-indole-2-carboxylic acid ethyl ester

Charge a total of 4.0 kg (19.56 mol) of 3-amino-1H-indole-2-carboxylic acid ethyl ester, 4.10 kg (27.33 mol, 1.4 equiv.) of 4-chloropyridine hydrochloride and 8.0 L of 1-methyl-2-pyrrolidinone to a 30-gal reactor and heat to 100° C. under nitrogen. Monitor the progress of the reaction by HPLC (Column—150×3.9 mm Waters Symmetry C18, 5 micron; mobile phase—60% acetonitrile/40% 0.1% TFA in water; flow rate—1.0 mL/min; wavelength—225 nm; $R_T$: 3-amino-1H-indole-2-carboxylic acid ethyl ester—1.5 min; 3-(4-pyridinylamino)-1H-indole-2-carboxylic acid ethyl ester—6.0 min; 4-chloropyridine—1.1 min). Typically achieve, a 99% conversion within 1 h. Allow the mixture to cool to 20° C. and add a total of 55.0 L of water. Extract the mixture with a total of 20.0 L of ethyl acetate and separate the layers. Adjust the pH of the aqueous phase was to pH=9.3 using 25% sodium hydroxide solution. Filter off the solid that forms and wash with 45.0 L of water and air dry. Further air dry the solid in a forced air oven at 50° C. for 24 h to give 4.20 kg, 77% yield, of the title compound: HPLC analysis 95.8% pure.

Step G4: 3-(4-Pyridinylamino)-1H-indole-2-carboxylic acid potassium salt

Charge a mixture of 7.50 kg (26.66 mol) of 3-amino-1H-indole-2-carboxylic acid ethyl ester, 37.5L of ethanol and 37.5 L of 4M KOH to a 30-gal reactor and heat to 75° C. over 30 min. Monitor the progress of the reaction by HPLC (Column—150×3.9 mm Waters Symmetry C18, 5 micron; mobile phase—20% acetonitrile/80% 0.1% TFA in water; flow rate—1.0 mL/min; wavelength—225 nm; $R_T$: 3-amino-1H-indole-2-carboxylic acid potassium salt—3.3 min; 3-amino-1H-indole-2-carboxylic acid ethyl ester—6.0 min). Typically achieve, a 100% conversion within 3 h. Cool the mixture to 25° C. over 2 h and concentrate at 50–60° C./50 torr to a residue. Add a total of 37.5 L of water and heat the mixture to and hold at 85° C. for 30 min. Cool the mixture to 10° C. over 2 hours, and then further cool to and hold at 5° C. for 2 hours. Filter off the solid that forms, wash with a total of 10 L of 4M KOH solution and air dry. Further dry the solid at 35° C. in a forced air oven for 72 h to give 10.9 kg, 140% yield of the title compound: HPLC analysis 70.7% pure.

Step G5: 3-(4-Pyridinylamino)-1H-indole-2-carboxylic acid

Charge a total of 10.9 kg (37.4 mol, 140% yield for ester hydrolysis) of 3-amino-1H-indole-2-carboxylic acid potassium salt and 75.0 L of water to a 30-gal glass lined reactor. Extract the stirring mixture with 75.0 L (3×25.0 L) of ethyl acetate. Adjust the pH of the aqueous phase to pH=6.0 by the addition of 7.0 L of 6N HCl at 20–22° C. and monitor the purity of the product by HPLC (Column—150×3.9 mm Waters Symmetry C18, 5 micron; mobile phase—20% acetontrile/80% 0.1% TFA in water; flow rate—1.0 mL/min; wavelength—225 nm; $R_T$: 3-amino-1H-indole-2-carboxylic acid—3.3 min). Stir the mixture for 45 min and the measure pH to be pH=6.0. Filter off the solid that forms, wash with a total of 50 L of water and air dry. Further dry the solid at 35° C. in a forced air oven for 24 hours to give 6.15 kg, 65.5% yield of 3-amino-1H-indole-2-carboxylic acid. HPLC analysis showed the compound to be 93.8% pure. Charge a total of 6.15 kg (24.28 mol) of the product, 11.3 kg (97.35 mol, 4.0 equiv.) of maleic acid, 62.0 L of methanol and 6.2 L of water was to a 30-gal reactor and heat to and hold at 70° C. for 45 min under nitrogen. Cool the mixture to 30° C. over 1.5 hours and concentrate at 60° C./50 torr to a wet solid. Add a total of 20.0 L of EPA and concentrate the mixture at 60° C./50 torr to a solid. Repeat this process. Add a total of 50.0 L of IPA to the residue and heat the mixture to and hold at 70° C. for 60 min, then cool to 20° C. over 16 h. Cool the mixture and hold at 2° C. for 1 hour. Monitor the purity of the product by HPLC (Column—150×3.9 mm Waters Symmetry C18, 5 micron; mobile phase—20% acetonitrile/80% 0.1% TFA in water, flow rate—1.0 mL/min; wavelength—225 nm; $R_T$: 3-amino-1H-indole-2-carboxylic acid—3.3 min; maleic acid—1.2 min). Filter off the solid, wash with 10.0 L of cold (5° C.) IPA and dry at 35° C. in a forced air oven to give 5.4 kg, 60.6% yield of 3-amino-1H-indole-2-carboxylic acid maleate salt: HPLC analysis 99.0% pure.

Charge a total of 7.9 kg (5.4 kg+2.5 kg from two runs) of 3-amino-1H-indole-2-carboxylic acid maleate salt and 50.0 L of 4M KOH to a 30-gal reactor and heat to and hold at 70° C. Add a total of 12.0 L of ethanol until the mixture becomes homogenous at 70° C. Cool the mixture to 20° C. over 2 h. Further cool the mixture to and hold at 4° C. for 1 hour. Monitor the purity of the product by HPLC (Column—150×3.9 mm Waters Symmetry C18, 5 micron; mobile phase—20% acetonitrile/80% 0.1% TFA in water; flow rate—1.0 mL/min; wavelength—225 nm; $R_T$: 3-amino-1H-indole-2-carboxylic acid potassium salt—3.3 min). Filter off the solid and wash with 10.0 L of 4M KOH (22.5% solution) and dry under nitrogen to give 9.4 kg, 151% yield of 3-amino-1H-indole-2-carboxylic acid potassium salt HPLC analysis 97.4% pure.

Charge a total of 18.1 kg (9.4 kg+8.7 kg from two runs) 3-amino-1H-indole-2-carboxylic acid potassium salt and 100.0 L of to a 30-gal reactor. Adjust the pH of the mixture to pH=5.95 by the addition of 13.0 L of 6N HCl at 23–27° C. Stir the mixture for 1.5 h at 22–25° C. Filter off the solid that forms and wash with 60.0 L of water. Monitor the purity of the product by HPLC (Column—150×3.9 mm Waters Symmetry C18, 5 micron; mobile phase—20% acetonitrile/80% 0.1% TFA in water; flow rate—1.0 mL/min; wavelength—225 nm; $R_T$: 3-amino-1H-indole-2-carboxylic acid—3.3 min). Dry the solid at 60° C./50 torr to give 10.2 kg, 41.1% yield of the title compound: HPLC analysis 98.4% pure.

Analysis: Calculated for $C_{14}H_{11}N_3O_2 \cdot 1.21 H_2O$: % C 61.15%; % H 4.91%; % N, 15.28%. Found, % C, 60.83%; % H, 5.05%; % N, 15.37%.

Example 29

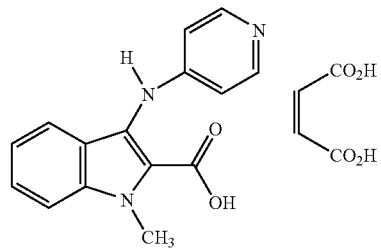

Salt Formation: 1-Methyl-3-(4-pyridinylamino)-1H-indole-2-carboxylic acid Maleate Under $N_2$, stir a mixture of 1-methyl-3-(4-pyridinylamino)-1H-indole-2-carboxylic acid ethyl ester (preparation described in Example 24A, also see U.S. Pat. No. 5,328,920, 0.5 g, 1.69 mmol) lithium hydroxide hydrate (0.106 g, 2.53 mmol) and water-ethanol, 1:4 at 50° C. for 4 h. Remove a portion of the ethanol and store the reaction mixture at approximately 5° C. overnight. Filter the resulting solid, wash with water, dry at 40° C. at high vacuum to obtain 0.41 g of a white solid. Suspend the solid in methanol and add maleic acid (0.346 g) and let stand for 0.5 h. Filter and concentrate the filtrate to obtain a tan solid. Recrystallize the solid from methanol/ethyl acetate and obtain 0.19 g (29%) of the title compound: MS 224 (—$CO_2$, M+H), m.p. 192–194° C. (dec.).

Analysis: Calculated for $C_{15}H_{13}N_3O_2 \cdot C_4H_4O_4$: 59.53% C; 4.47% H; 10.96% N; Found: 59.47% C; 4.56% H; 10.86% N.

Example 30

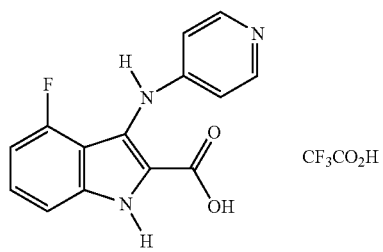

Scheme F

Step F3: 4-Fluoro-3-(4-pyridinylamino)-1H-indole-2-carboxylic acid Trifluoroacetate Salt Stir at ambient temperature for 3 h a solution of 4-fluoro-3-(4-pyridinylamino)-1H-indole-2-carboxylic tert-butyl ester (Example 17, 0.15 g, 0.458 mmol) in 35% trifluoroacetic acid/dichloromethane. Concentrate the reaction under vacuum to obtain a gray solid. Dry the solid at 40° C. under vacuum and then triturate with hot ethyl acetate. Allow to cool to ambient temperature and collect a light gray powder. Dry the powder at 45° C. under vacuum for 2 h and obtain 0.15 g (88%) of the title compound: MS 272(M+H), m.p. 231–234° C. (dec.)

Example 31

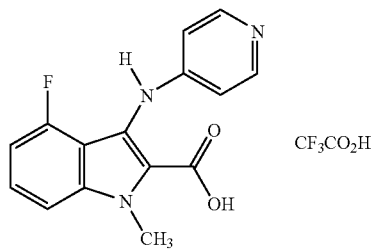

Scheme F

Step F3: 4-Fluoro-1-Methyl-3-(4-pyridinylamino)-1H-indole-2-carboxylic acid Trifluoroacetate Salt Follow the procedure of Example 30 starting with 4-fluoro-1-methyl-3-(4-pyridinylamino)-1H-indole-2-carboxylic tert-butyl ester (Example 25) to obtain the title compound as off-white powder: MS 286(M+H), m.p. 197–199° C.

Example 32

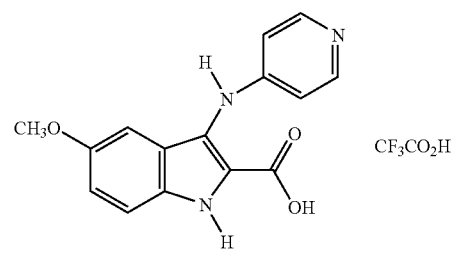

Scheme F

Step F3: 5-Methoxy-3-(4-pyridinylamino)-1H-indole-2-carboxylic acid Trifluoroacetate Salt Follow the procedure of Example 30 starting with 5-methoxy-3-(4-pyridinylamino)-1H-indole-2-carboxylic tert-butyl ester (Example 21) to obtain the title compound as on-white powder: ESI/MS 284(M+H), m.p. 211–213° C.

Example 33

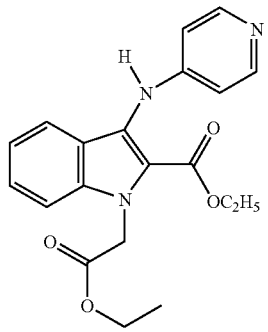

Scheme F

Step F8: 1-Ethoxycarbonylmethyl-3-(pyridin-4-ylamino)-1H-indole-2-carboxylic acid ethyl ester Under nitrogen, stir and cool to 0° C. a mixture of ethyl 3-(4-pyridinylamino)indole-2-carboxylate (see U.S. Pat. No. 5,328,920; 0.20 g, 0.711 mmol) in dimethylformamide (5 mL). Add a 1M solution of potassium tert-butoxide in tetrahydrofuran (0.75 mL, 0.75 mmol) in one portion, stir for 10 min, and then add ethyl bromoacetate (0.12 g, 0.72 mmol) in one portion. Stir at 0° C. for 50 min and quench the reaction into water (30 mL). Extract the aqueous mixture with ethyl acetate (2×20 mL), combine the extracts, wash with water (25 mL), brine (25 mL) and dry over MgSO$_4$. Concentrate under vacuum, chromatograph the residue on a Redisep silica gel cartridge (10 g) eluting with 5% methanol/ dichloromethane to 20% methanol/dichloromethane. Combine non-homogeneous fractions concentrate and chromatograph again as above. Combine all homogenous fractions and concentrate to obtain 0.13 g (50%) of the title compound as a white solid: MS 368(M+H).

Example 34

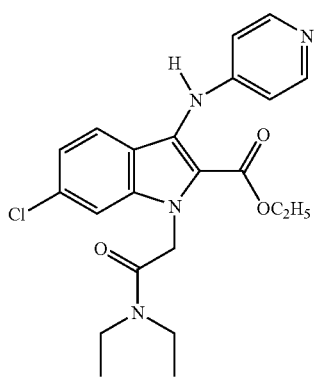

Scheme F

Step F8: 6-Chloro-1-diethylcarbamoylmethyl-3-(pyridin-4-ylamino)-1H-indole-2-carboxylic acid ethyl ester Under nitrogen, stir and cool to 0° C. a mixture of ethyl 6-chloro-3-(4-pyridinylamino)indole-2-carboxylate (0.50 g, 1.58 mmol) in dimethylformamide (5 mL). Add a 1M solution of potassium tert-butoxide in tetrahydrofuran (1.7 mL, 1.7 mmol) over a 2 min period, and stir for 10 min. Add 2-chlor-N,N-diethylacetamide (0.22 mL, 1.6 mmol) in one portion and stir at ambient temperature overnight. Quench the reaction into water (35 mL), and extract the aqueous mixture with ethyl acetate (2×20 mL). Combine the extracts, wash with water (25 mL), brine (25 mL) and dry over MgSO$_4$. Concentrate under vacuum, and chromatograph the residue on a Redisep silica gel cartridge (10 g) eluting with 5% methanol/dichloromethane to 20% methanol/dichloromethane. Combine all homogenous fractions and concentrate to obtain a solid. Recrystallize the solid from ethyl acetate and obtain 0.1 g of the title compound as a white solid: MS 429(M+H), m.p. 212–214° C.

Example 35

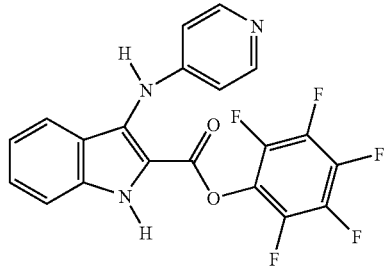

Scheme F

Step F5: 3-(Pyridin-4-ylamino)-1H-indole-2-carboxylic acid pentafluorophenyl ester Stir under N$_2$ a suspension of 3-(4-pyridinylamino)-1H-indole-2-carboxylic acid (0.2 g, 0.78 mmol) in dimethylformamide, add pyridine (0.13 mL, 1.6 mmol) and then add dropwise pentafluorophenyl trifluoroacetate (0.31 g, 1.13 mmol). Stir the reaction overnight at ambient temperature and quench into water. Extract the aqueous mixture with ethyl acetate, wash with 5% aqueous potassium carbonate, brine and dry over MgSO$_4$. Concentrate under vacuum to afford a crude solid, which is triturated with ether to obtain 0.13 g (41%) of the title compound: MS 420(M+H).

Example 36

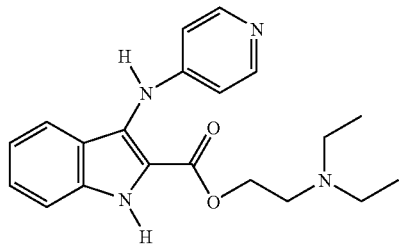

Scheme F

Step F7: 3-(Pyridin-4-ylamino)-1H-indole-2-carboxylic Acid 2-diethylamino-ethyl ester Stir under N$_2$ at 0° C. a suspension of NaH (29 mg, 0.72 mmol of 60% oil dispersion) in 1-methyl-2-pyrrolidinone (15 mL), and slowly add N,N-diethylethanolamine(0.095 mL, 0.72 mmol). Stir for 10 min and then add dropwise 3-(pyridin-4-ylamino)-1H-indole-2-carboxylic acid pentafluorophenyl ester (100 mg, 0.24 mmol). Allow the reaction to reach ambient temperature and stir overnight. Quench into water and extract with ethyl acetate. Wash the extract with water, brine, dry (MgSO$_4$), filter and concentrate under vacuum to obtain crude product. Chromatograph on silica gel (10 g, Sepack cartridge) and use 1:1 methanol/ethyl acetate as eluent. Combine like fractions and concentrate under vacuum to obtain 26.3 mg (31%) of the titled compound: MS 353 (M+H).

Example 37

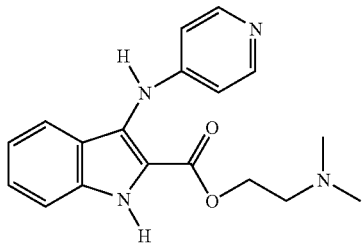

Scheme F

Step F7: 3-(Pyridin-4-ylamino)-1H-indole-2-carboxylic acid 2-dimethylamino-ethyl ester Follow the procedure of Example 36 starting with N,N-dimethyl-ethanolamine to obtain the title compound as a solid: MS 325(M+H).

Example 38

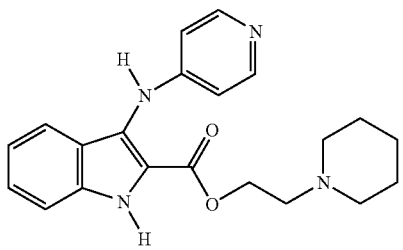

Scheme F

Step F4: 3-(Pyridin-4-ylamino)-1H-indole-2-carboxylic acid 2-piperidin-1-yl-ethyl ester Stir under $N_2$ at 0° C. a mixture of 3-(4-pyridinylamino)-1H-indole-2-carboxylic acid (0.25 g, 1 mmol), benzotriazol-1-yloxytris(pyrrlidino)-phosphonium hexafluorophosphate (0.52 g, 1 mmol), diethylisopropylamine (0.175 mL, 1 mmol) and 1-methyl-2-pyrrolidinone (4.0 mL). Add 1-piperidineethanol (0.50 mL, 3.8 mmol) in one portion and stir at ambient temperature for 18.5 h. Pour the reaction into 5% aqueous potassium carbonate and extract with ethyl acetate (2×20mL). Wash the combined extract with water (20 mL), brine (20 mL), dry over $MgSO_4$, filter and concentrate under vacuum to a dark residue. Chromatograph over silica gel (Redisep cartridge, 30 g) and elute with a step gradient of 10% methanol/dichloromethane (150 mL) to 20% methanol/dichloromethane. Concentrate like fractions under vacuum to an oil. Dry the oil under high vacuum at ambient temperature and obtain 0.14 g of the title compound as a tan foam: MS 365(M+H), TLC (silica gel, 0.5/9.5/90 ammonium hydroxide/methanol/dichloromethane) $R_f$=0.25.

Example 39

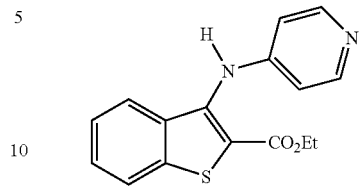

Scheme H

Step H1: 3-(4-Pyridinylamino)-benzo(b)thiophene-2-carboxylic acid, ethyl ester

Cool to −78° C. a solution of anhydrous tetrahydrofuran (25 mL) and 3-(4-pyridyl)amino)benzo(b)thiophene HCl (see U.S. Pat. No. 5,328,920; 298 mg, 1.09 mmol) and add a 2 molar solution of lithium di-isopropylamide in heptane/tetrahydrofuran/ethylbenzene (1.9 mL, 3.8 mmol). After 2 h, add diethyl carbonate (1.2 mL, 9.89 mmol). Stir the reaction for another 3 h while the temperature rose to −40° C. Remove the cold bath and after 30 min quench the reaction by the addition of water (10 mL). Extract the reaction with ethyl acetate. Separate the organic layer, wash with brine, dry over sodium sulfate, filter and concentrate. Purify the residue on an ISCO RediSep 10-gram silicagel cartridge, with ethyl acetate—50% heptane and ethyl acetate as eluents. Combine product containing fractions and concentrate to give ethyl 3-[(4-pyridyl) amino]-benzo[b]thiophenyl-2-carboxylate as a tan solid (289 mg, 86%): ESI/MS 299 (M+H); $^1$H-NMR δ 1.41–1.43 (m, 3H), 4.11–4.43 (m, 2H), 6.81 (2H), 7.23–7.52 (m, 1H), 7.60 (d, J=9 Hz, 1H), 7.84 (d, J=9 Hz, 1H), 8.36 (br d, 2H), 8.43 (s, 1H, NH); $^{13}$C-NMR δ 14.29, 61.44, 112.61, 113.92, 123.36, 124.11, 125.15, 127.86, 132.53, 139.49, 141.75, 149.68, 150.36, 164.53.

Example 40

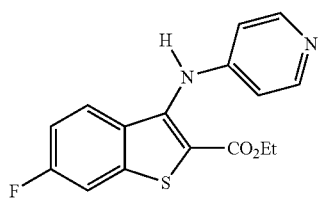

Scheme H

Step H1: 6-Fluoro-3-(4-pyridinylamino)-benzo[b]thiophene-2-carboxylic acid, ethyl ester Cool to −78° C. a solution of anhydrous tetrahydrofuran (20 mL) and 6-fluoro-3-[4-pyridyl)amino]benzo[b]thiophene (see U.S. Pat. No. 5,177,088; 181 mg, 0.741 mmol) and add a 2 molar solution of lithium di-isopropylamide in heptane/tetrahydrofuran/ethylbenzene (0.74 mL, 1.5 mmol). After 2 h, add diethyl carbonate (0.8 mL, 6.59 mmol). Stir the reaction for another 1 h, allow to warm slowly to room temperature and continue to stir overnight. Quench the reaction by the addition of water (10 mL).

Remove the solvents on a rotary evaporator and take up the residue in ethyl acetate. Wash the ethyl acetate with water and brine, dry over sodium sulfate, filter and concentrate. Purify the residue on an ISCO RediSep 10-gram silicagel cartridge, with ethyl acetate–50% heptane and ethyl acetate—0.5% NH$_4$OH as eluents. Combine product containing fractions and concentrate to give ethyl 6-fluoro-3-[(4-pyridyl)amino]benzo[b]thiophenyl-2-carboxylate: ESI/MS 317 (M+H); $^1$H-NMR δ 1.40–1.43 (m, 3H); 4.35–4.42 (m, 2H); 6.80 (br d, 2H); 7.04–7.10 (m, 1H); 7.48–7.57 (m, 2H); 8.37 (br s, 2H); 8.43 (s, 1H, NH); $^3$C-NMR δ 14.3; 61.5; 109.2 ($J_{CF}$=25 Hz); 112.7 ($J_{CF}$=4 Hz); 113.4; 113.7 ($J_{CF}$=25 Hz); 126.7 ($J_{CF}$=9 Hz); 129.0; 140.9 ($J_{CF}$=11 Hz); 141.4; 149.5; 150.5; 162.4 ($J_{CF}$=260 Hz); 164.1; $^{19}$F-NMR (282 MHz) δ–110.8.

Example 41

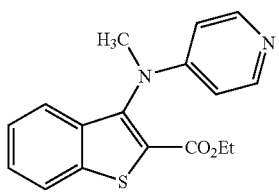

Scheme H

Step H1: Ethyl 3-[(4-pyridyl)amino-N-methyl]benzo[b]thiophenyl-2-carboxylate

Under nitrogen, cool to −76° C. a solution of anhydrous tetrahydrofuran (4 mL) and 3-[4-pyridyl)amino-N-methyl]benzo[b]thiophene HCl (see U.S. Pat. No. 5,328,920; 50 mg, 0.18 mmol) and add a 2 molar solution of lithium di-isopropylamide in heptane/tetrahydrofuran/ethylbenzene (0.28 mL, 0.54 mmol). After 20 min, replace the dry ice/acetone bath with an ice/water bath. After 1 h, add diethyl carbonate (0.27 mL, 2.23 mmol) and stir the reaction for 4 h at this temperature and then overnight at room temperature. Quench the reaction by the addition of water (3 mL). Extract the reaction with ether, and wash the extract with brine, dry it over sodium sulfate, filter and concentrate. Purify the residue on an ISCO RediSep 4 gram silicagel cartridge, with ethyl acetate—3% methanol-NH$_4$OH as eluent. Combine product containing fractions and concentrate to give ethyl 3-[(4-pyridyl)amino-N-methyl]benzo[b]thiophenyl-2-carboxylate as a tan solid (30 mg, 53%): ESI/MS 313 (M+H); $^1$H-NMR δ 1.26 (t, 3H, J=9 Hz), 3.38 (s, 3H, Me), 4.30 (q, 2H, J=6 Hz), 6.42 (br s, 2H), 7.57 (m, 3H), 7.90 (d, 1H, J=9 Hz), 8.21 (br s, 2H); $^{13}$C-NMR δ 14.1, 38.2, 61.6, 107.7, 123.3, 123.4, 125.2, 127.9, 135.8, 139.3, 142.6, 149.9, 153.5, 161.2.

Example 42

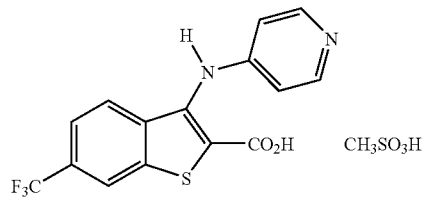

Scheme H

Step H2: 3-(4-Pyridinylamino)-6-trifluoromethyl-benzo[b]thiophene-2-carboxylic acid Methane sulfonate salt Under nitrogen, cool to −78° C. a solution of anhydrous tetrahydrofuran (60 mL) and 3-(4-pyridinylamino)-6-trifluoromethylbenzo[b]thiophene (see U.S. Pat. No. 5,328,920; 0.47 g, 1.6 mmol) and add a 2.5 molar solution in hexanes of n-butyl lithium (1.3 mL, 3.25 mmol) by syringe. Stir the reaction for 2 h, pour it into a beaker containing 140 g of dry ice and 10 mL of anhydrous tetrahydrofuran. Stir the reaction for 1 h, add water (50 mL), and basify to pH 13–14 with 10% aqueous sodium hydroxide. Extract the basic solution with ether (2×10 mL) and acidify the aqueous portion with 3% aqueous HCl. At about pH 7 a white solid precipitates from solution. Collect the solid and dry overnight under vacuum to afford 0.35 g (65%) of the free base of the title compound. React a portion of the free base with methane sulfonic acid and obtain 59.0 mg of the title compound: ESI/MS 339 (M+H); HPLC: R$_t$=1.38 min. (95/5/0.1 (A) 5/95/0.1 (B) Water/CAN/Formic Acid YMC ODS-A 2×50 mm 1 mL/min Gradient Composition: 100% A for 0.1 min Linear Gradient to 100% B at 2 min Hold until 3.5 min.)

Example 43

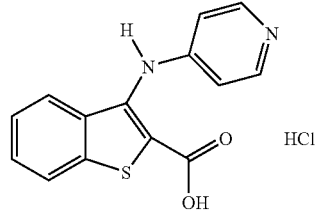

Scheme H

Step H2: 3-(4-Pyridinylamino)-benzo[b]thiophene-2-carboxylic acid Hydrochloride salt Follow the procedure of Example 42 starting with 3-(4-pyridinylamino)-6-benzo[b]thiophene (see U.S. Pat. No. 5,328,920 for synthesis). Form the hydrochloride salt in methanol and ethereal HCl to obtain the title compound as white solid: ESI/MS 271 (M+H).

Example 44

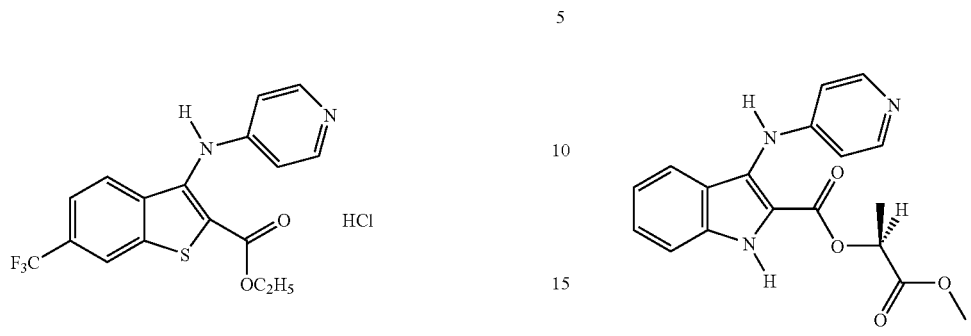

Scheme H

Step H1: 3-(4-Pyridinylamino)-6-trifluoromethyl-benzo[b]thiophene-2-carboxylic acid ethyl ester Hydrochloride salt Follow the procedure of Example 40 starting with 3-(4-pyridinylamino)-6-trifluoromethylbenzo[b]thiophene (see U.S. Pat. No. 5,328,920 for synthesis). Form the hydrochloride salt in ethereal HCl and obtain the title compound as an off-white solid: MS 367(M+H), TLC (silica gel, ethyl acetate/methanol/ammonium hydroxide) $R_f$=0.80.

Example 45

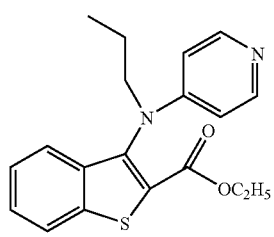

Scheme H

Step H1: 3-(Propyl-4-pyridinylamino)benzo[b]thiophene-2-carboxylic acid ethyl ester Follow the procedure of Example 40 starting with 3-(propyl-4-pyridinyl-amino)benzo[b]thiophene (see U.S. Pat. No. 5,328,920 for synthesis). Obtain the title compound as a tan solid: ESI/MS 341 (M+H); HPLC: $R_t$=1.53 min. (95/5/0.1 (A) 5/95/0.1 (B) Water/CAN/Formic Acid YMC ODS-A 2×50 mm 1 mL/min Gradient Composition: 100% A for 0.1 min Linear Gradient to 100% B at 2 min Hold until 3.5 min.)

Example 46

Scheme F

Step F4: 3-(Pyridin-4-ylamino)-1H-indole-2-carboxylic acid (S)-1-methoxycarbonyl-ethyl ester Stir at 0° C. a mixture of 3-(4-pyridinylamino)-1H-indole-2-carboxylic acid (3.0 g, 12 mmol), methyl (S)-(–)-lactate (2.3 mL, 24 mmol), 4-methylmorpholine (2.6 mL,24 mmol) and DMF (50.0 mL). Add benzotriazol-1-yloxytris(dimethylamino)phosphonium hexafluorophosphate (BOP, 5.32 g, 12 mmol) in one portion and stir at ambient temperature overnight. Add brine (50 mL) and extract with ethyl acetate (3×200 mL). Concentrate under vacuum to an oil. Chromatograph over silica gel (5 g) and elute with dichloromethane, EtOAC, and MeOH. Concentrate like fractions under vacuum to an oil. Treat the oil with HCl in ether (10 mL) add additional ether (50 mL) and concentrate under vacuum to an oil. Treat the oil with 5% aqueous $NaHCO_3$ and extract with EtOAc. Dry the extract over $Na_2SO_4$, filter and concentrate to an oil. Scratch the oil with a glass rod in the presence of ether to obtain a sticky solid. Add $CH_3CN$ and then ether and obtain of the title compound as a yellow solid, 140 mg: MS 340(M+H), $R_t$=2.73 min. (95/5/0.1 (A) 5/95/0.1 (B) Water/CAN/Formic Acid YMC ODS-A 2×50 mm 1 mL/min Gradient Composition: 100% A for 0.1 min Linear Gradient to 100% B at 2 min Hold until 3.5 min.)

Example 47

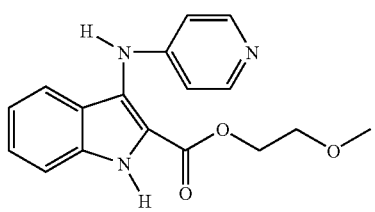

Scheme F

Step F4: 3-(Pyridin-4-ylamino)-1H-indole-2-carboxylic acid 2-methoxy-ethyl ester Follow the procedure of Example 46 but cool the reaction to −10 to −15° C. substituting 2-methoxy ethanol for methyl (S)-(−)-lactate and purify by column chromatography on silica gel eluting with 15% MeOH/dichloromethane to obtain the title compound: MS 312(M+H), TLC (silica gel, 15% MeOH/dichloromethane) $R_f$=0.53.

Example 48

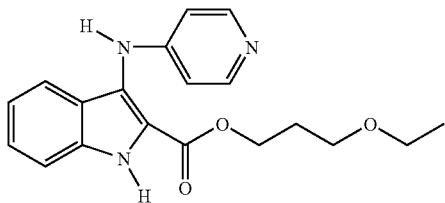

Scheme F

Step F4: 3-(Pyridin-4-ylamino)-1H-indole-2-carboxylic acid 3-ethoxy-propyl ester Follow the procedure of Example 47 substituting 2-ethoxy ethanol for 2-methoxy ethanol and purify by column chromatography on silica gel eluting with 8.5% MeOH/dichloromethane to obtain the title compound: MS 340(M+H), TLC (silica gel, 8.5% MeOH/dichloromethane) $R_f$=0.30.

Example 49

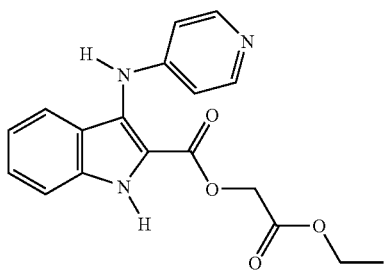

Scheme F

Step F4: 3-(Pyridin-4-ylamino)-1H-indole-2-carboxylic acid ethoxycarbonylmethyl ester Follow the procedure of Example 46 substituting ethyl glycolate for methyl (S)-(−)-lactate and NMP for DMF purify by column chromatography on silica gel eluting with dichloromethane, EtOAc and 1% MeOH/dichloromethane to obtain the title compound: MS 340(M+H), ), $R_t$=1.19 min. (95/5/0.1 (A) 5/95/0.1 (B) Water/CAN/Formic Acid YMC ODS-A 2×50 mm 1 mL/min Gradient Composition: 100% A for 0.1 min Linear Gradient to 100% B at 2 min Hold until 3.5 min.) TLC $R_f$=0.51 (3:1 EtOAc:CH$_3$OH, silica gel).

Example 50

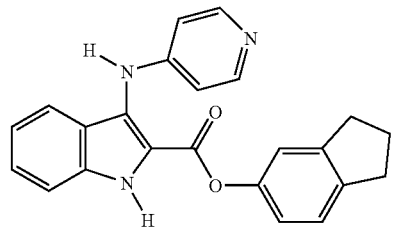

Scheme F

Step F4: 3-(Pyridin-4-ylamino)-1H-indole-2-carboxylic acid indan-5-yl ester

Follow the procedure of Example 49 substituting 5-indanol for ethyl glycolate and benzotriazol-1-yloxytris(pyrrolidino)-phosphonium hexafluorophosphate (PYBOP) for BOP. Purify by column chromatography on silica gel eluting with EtOAc to obtain the title compound: MS 370(M+H), $R_t$=1.35 min. (95/5/0.1 (A) 5/95/0.1 (B) Water/CAN/Formic Acid YMC ODS-A 2×50 mm 1 mL/min Gradient Composition: 100% A for 0.1 min Linear Gradient to 100% B at 2 min Hold until 3.5 min.); TLC Rf=0.52 (EtOAc, silica gel).

Example 51

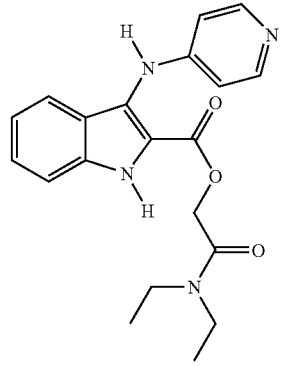

Scheme F

Step F4: 3-(Pyridin-4-ylamino)-1H-indole-2-carboxylic acid diethylcarbamoylmethyl ester Stir at 50° C. for 10 min. a mixture of 3-(4-pyridinylamino)-1H-indole-2-carboxylic acid (2.0 g, 8 mmol), KI (10 mg) and Cs$_2$CO$_3$ (2.8 g, 8.6 mmol) in DMF (125 mL). Allow to cool to ambient temperature and then cool in an ice bath. Add 2-chloro-N,N-diethylacetamide (1.077 g, 0.9 mmol) and allow to warm to ambient temperature. Add a brine solution to the reaction and extract with EtOAc (3×). Wash the extract with brine and water, dry (MgSO$_4$), filter and concentrate under vacuum to give a semi-solid. Flash chromatograph over silica gel eluting first with EtOAc and 10% MeOH/EtOAc and obtain 0.317 g the title compound as a solid: MS 367(M+H); HPLC: $R_t$=4.75 min. (95/5/0.1 (A) 5/95/0.1 (B) Water/CAN/Formic Acid YMC ODS-A 2×50 mm 1 mL/min Gradient Composition: 100% A for 0.1 min Linear Gradient to 100% B at 2 min Hold until 3.5 min).

Example 52

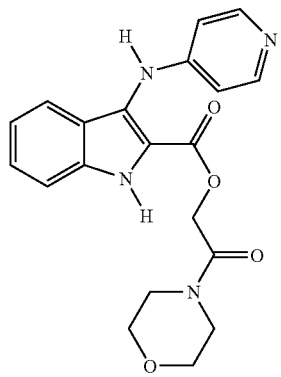

Scheme F: 3-(Pyridin-4-ylamino)-1H-indole-2-carboxylic acid 2-morpholin-4-yl-2-oxo-ethyl ester Intermediate: 4-(Chloroacetyl)morpholine Utilize a Quest 205 Parallel Synthesizer and to a mixture of morpholine (2.6 g, 30 mmol), dichloromethane (45 mL) and 2M K₂CO₃ slowly add chloroacetylchloride (3.73 g, 33 mmol) in dichloromethane (10 mL). Agitate the reaction overnight and filter off the organic layer. Extract the aqueous with dichloromethane (20 mL) and add it to the previously collected organic layer. Dry the organic phase (MgSO₄) and concentrate under vacuum to obtain the title compound.

Step F4: 3-(Pyridin-4-ylamino)-1H-indole-2-carboxylic acid 2-morpholin-4-yl-2-oxo-ethyl ester Follow the procedure of Example 51 substituting 4-(chloroacetyl)morpholine for 2-chloro-N,N-diethylacetamide. Collect the precipitate that forms in the EtOAc extract, wash with ether to obtain the title compound as a solid: MS 381(M+H); HPLC: $R_f$=2.48 min. (95/5/0.1 (A) 5/95/0.1 (B) Water/CAN/Formic Acid YMC ODS-A 2×50 mm 1 mL/MIN Gradient Composition: 100% A for 0.1 min Linear Gradient to 100% B at 2 min Hold until 3.5 min).

Example 53

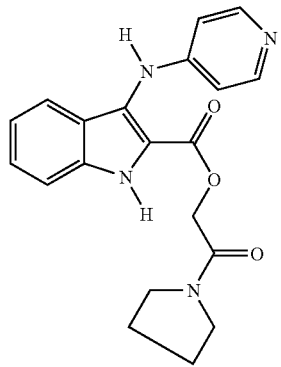

Scheme F: 3-(Pyridin-4-ylamino)-1H-indole-2-carboxylic acid 2-oxo-2-pyrrolidin-1-yl-ethyl ester Intermediate: 1 Choroacetylpyrrolidine Follow the procedure of Example 53, substituting pyrrolidine for morpholine and obtain the title compound.

Step F4: 3-(Pyridin-4-ylamino)-1H-indole-2-carboxylic acid 2-oxo-2-pyrrolidin-1-yl-ethyl ester Follow the procedure of Example 51 substituting 1-(chloroacetyl)pyrrolidine for 2-chloro-N,N-diethylacetamide. Collect the precipitate that forms in the EtOAc extract, wash with ether to obtain the title compound as a solid: MS 365(M+H); HPLC: $R_f$=2.58 min. (95/5/0.1 (A) 5/95/0.1 (B) Water/CAN/Formic Acid YMC ODS-A 2×50 mm 1 mL/min Gradient Composition: 100% A for 0.1 min Linear Gradient to 100% B at 2 min Hold until 3.5 min.).

Example 54

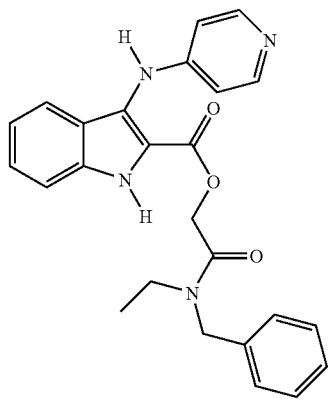

Scheme F: 3-(Pyridin-4-ylamino)-1H-indole-2-carboxylic Acid (benzyl-ethyl-carbamoyl)-methyl ester Intermediate: 2-Chloro-N-ethyl-N-(phenylmethyl)acetamide Follow the procedure of Example 53, substituting N-benzyl-N-ethyl amine for morpholine and obtain the title compound.

Step F4: 3-(Pyridin-4-ylamino)-1H-indole-2-carboxylic acid (benzyl-ethyl-carbamoyl)-methyl ester Follow the procedure of Example 51 substituting 2-chloro-N-ethyl-N-(phenylmethyl)acetamide for 2-chloro-N,N-diethylacetamide. Collect the precipitate that forms in the EtOAc extract, wash with ether to obtain the title compound as a yellow solid: MS 429(M+H); HPLC: $R_f$=2.72 min. (95/5/0.1 (A) 5/95/0.1 (B) Water/CAN/Formic Acid YMC ODS-A 2×50 mm 1 mL/min Gradient Composition: 100% A for 0.1 min Linear Gradient to 100% B at 2 min Hold until 3.5 min).

Example 55

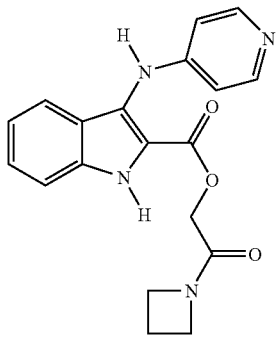

Scheme F: 3-(Pyridin-4-ylamino)-1H-indole-2-carboxylic acid 2-azetidin-1-yl-2-oxo-ethyl ester Intermediate: 1-(chloroacetyl)azetidine To a stirring solution of chloroacetylchloride and K₂CO₃ (4.14 g, 30 mmol) in dichloromethane-water (45–15 mL), add slowly by syringe azetidine (2.8 g, 30 mmol). After addition, stir overnight at ambient temperature. Separate the organic layer and wash with H₂O (twice) and brine (twice), and then concentrate under reduced pressure to give the title compound.

Step F4: 3-(Pyridin-4-ylamino)-1H-indole-2-carboxylic acid 2-azetidin-1-yl-2-oxo-ethyl ester Follow the procedure of Example 51 substituting 1-(chloroacetyl)azetidine for 2-chloro-N,N-diethylacetamide. Collect the precipitate that forms in the EtOAc extract, wash with ether to obtain the title compound as a yellow solid: MS 351(M+H); HPLC: R$_f$=2.52 min. (95/5/0.1 (A) 5/95/0.1 (B) Water/CAN/Formic Acid YMC ODS-A 2×50 mm 1 mL/min Gradient Composition: 100% A for 0.1 min Linear Gradient to 100% B at 2 min Hold until 3.5 min).

Example 56

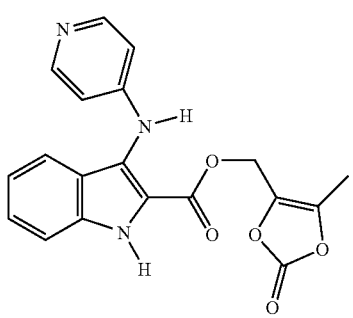

Scheme F

Step F4: 3-(Pyridin-4-ylamino)-1H-indole-2-carboxylic acid 5-methyl-2-oxo-[1,3]dioxol-4-ylmethyl ester Follow the procedure of Example 51 substituting 4-(bromomethyl)-5-methyl-1,3-dioxol-2-one (which was prepared in accordance with the procedures set forth in Saari, W. S., et al., *J. Med. Chem.*, (1984), 27, 713–717) for 2-chloro-N,N-diethylacetamide. Purify by column chromatography on silica gel eluting with 10% MeOH/EtOAc and then 15% MeOH/EtOAc to obtain the title compound as a pale yellow powder: MS 366(M+H).

Example 57

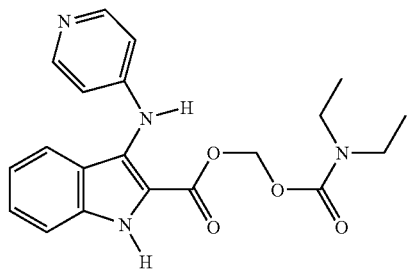

Scheme F:
3-(Pyridin-4-ylamino)-1H-indole-2-carboxylic acid diethylcarbamoyloxymethyl ester Intermediate: Chloromethyl diethylcarbamate To a stirred solution of chloromethyl chloroformate (7.09 g, 5.5 mmol) in heptane (100 mL) at −20° C. add a solution of diethylamine (10.4 g, 14.7 mmol) in heptane (50 mL), dropwise. Maintain the internal temperature between −15° C. to −5° C. and after 1 h quench the reaction with water. Separate the layers and wash the organic phase with 10% aqueous HCl, water and NaHCO₃ solution. Dry the organic layer (MgSO₄), filter and concentrate under reduced pressure to obtain 8.3 g of the title compound.

Step F4: 3-(Pyridin-4-ylamino)-1H-indole-2-carboxylic acid diethylcarbamoyloxymethyl ester Stir a mixture of 3-(4-pyridinylamino)-1H-indole-2-carboxylic acid (2.0 g, 8.0 mmol), chloromethyl diethylcarbamate (1.7 g, 10.4 mmol) and K₂CO₃ in DMF (50 mL) at ambient temperature overnight. Add EtOAc (400 mL), to the reaction mixture, wash the organic layer with brine solution (400 mL) and concentrate to an oil. Purify by flash chromatography over silica gel (40 g) eluting with EtOAc and then 10% MeOH/EtOAc. Collect like fractions and concentrate under vacuum to yield an oil. Crystallize from heptane-ether to obtain 1.1 g (36%) of the title compound as a white powder: MS 383(M+H).

Example 58

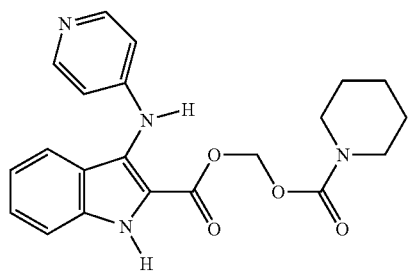

Scheme F: 3-(Pyridin-4-ylamino)-1H-indole-2-carboxylic acid piperidine-1-carbonyloxymethyl ester Intermediate: 1-piperidinecarboxylic acid, chloromethyl ester Follow the procedure of Example 57, substituting piperidine for diethylamine, obtain the title compound.

Step F4: 3-(Pyridin-4-ylamino)-1H-indole-2-carboxylic acid piperidine-1-carbonyloxymethyl ester Follow the procedure of Example 57 Step F4, substituting 1-piperidinecarboxylic acid, chloromethyl ester for chloromethyl diethylcarbamate to obtain the title compound as a solid: MS 395(M+H).

Example 59

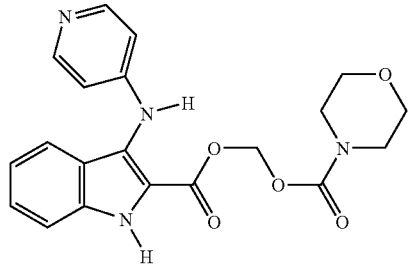

Scheme F: 3-(Pyridin-4-ylamino)-1H-indole-2-carboxylic acid morpholine-4-carbonyloxymethyl ester Intermediate: 4-Morpholinecarboxylic acid, choromethyl ester Follow the procedure of Example 57, substituting morpholine for diethylamine and obtain the title compound.

Step F4: 3-(Pyridin-4-ylamino)-1H-indole-2-carboxylic acid morpholine-4-carbonyloxymethyl ester Follow the procedure of Example 57, substituting 4-morpholinecarboxylic-acid, chloromethyl ester for chloromethyl diethylcarbamate to obtain the title compound as a solid: MS 397(M+H).

Example 60

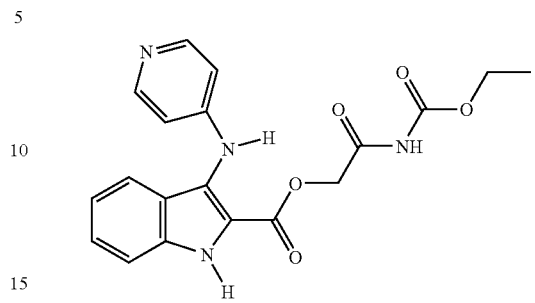

Scheme F

Step F4: 3-(Pyridin-4-ylamino)-1H-indole-2-carboxylic acid 2-ethoxycarbonylamino-2-oxo-ethyl ester Follow the procedure of Example 57, substituting N-chloroacetyl urethane for chloromethyl diethylcarbamate. Purify by column chromatography eluting with 10% MeOH/EtOAc and then 15% MeOH/EtOAc. Recrystallize form $CH_3CN$ to obtain the title compound as a solid: MS 383(M+H).

Example 61

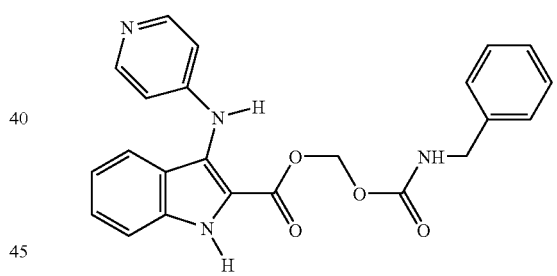

Scheme F:
3-(Pyridin-4-ylamino)-1H-indole-2-carboxylic acid benzylcarbamoyloxymethyl ester Intermediate: (Phenylmethyl)carbamic acid, chloromethyl-ester Follow the procedure of Example 57, substituting benzylamine for diethylamine and obtain the title compound.

Step F4: 3-(Pyridin-4-ylamino)-1H-indole-2-carboxylic acid benzylcarbamoyloxymethyl ester Follow the procedure of Example 57 Step B, substituting (phenylmethyl)carbamic acid chloromethyl ester for chloromethyl diethylcarbamate. Purify by column chromatography eluting with 10% MeOH/EtOAc and then 20% MeOH/EtOAc to obtain the title compound as a solid: MS 417(M+H).

Example 62

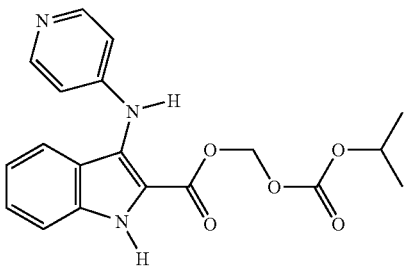

Scheme F:
3-(Pyridin-4-ylamino)-1H-indole-2-carboxylic acid isopropoxycarbonyloxymethyl ester Intermediate: Chloromethyl carbonic acid 1-methyl ester Stir and cool to −15° C. a solution of chloromethyl chloroformate (3.55 g, 27.5 mmol) in dichloromethane (30 mL) and add a solution of isopropyl alcohol (1.51 g, 2.5 mmol) in pyridine (2.18 g, 2.5 mmol), dropwise to maintain an internal temperature of between 18° C. to −5° C. After 2 h, quench into water, separate the layers and wash the organic phase with 10% aqueous HCl, water, NaHCO₃ solution and water. Dry with MgSO₄, filter and concentrate to obtain the title compound as 3.6 g of a colorless oil.

Step F4: 3-(Pyridin-4-ylamino)-1H-indole-2-carboxylic acid isopropoxycarbonyloxymethyl ester Follow the procedure of Example 57, substituting chloromethyl carbonic acid 1-methyl ester for chloromethyl diethylcarbamate and add KI (100 mg) to the reaction mixture. Allow the reaction to proceed for 3 hours, and obtain the title compound as a solid: MS 370(M+H).

Example 63

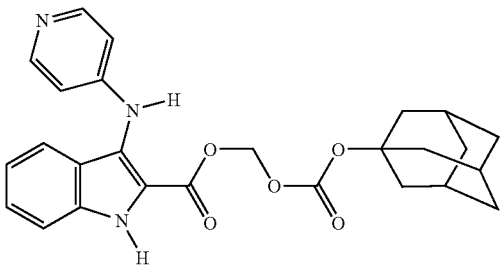

Scheme F: 3-(Pyridin-4-ylamino)-1H-indole-2-carboxylic acid adamantan-1-yloxycarbonyloxymethyl ester Intermediate: Chloromethyl 1-adamantyl carbonate Follow the procedure of Example 62, substituting 1-adamantanol for isopropyl alcohol to obtain the title compound.

Step F4: 3-(Pyridin-4-ylamino)-1H-indole-2-carboxylic acid adamantan-1-yloxycarbonyloxymethyl ester Follow the procedure of Example 62 substituting chloromethyl 1-adamantyl carbonate for chloromethyl carbonic acid 1-methyl ester, but allow the reaction to proceed overnight. Obtain the title compound as a solid: MS 462 (M+H).

Example 64

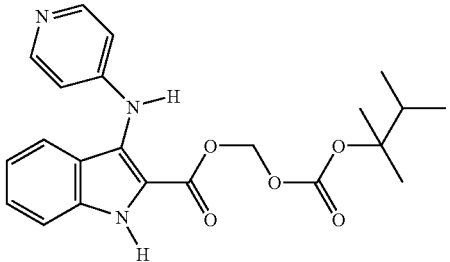

Scheme F: 3-(Pyridin-4-ylamino)-1H-indole-2-carboxylic acid 1,1,2-trimethyl-propoxycarbonyloxymethyl ester Intermediate: Carbonic acid chloromethyl ester 1,1,2-trimethyl-propyl ester Follow the procedure of Example 62, substituting 2,3-dimethyl-2-butanol for isopropyl alcohol to obtain the title compound.

Step F4: 3-(Pyridin-4-ylamino)-1H-indole-2-carboxylic acid 1,1,2-trimethyl-propoxycarbonyloxymethyl ester Follow the procedure of Example 62, substituting carbonic acid chloromethyl ester 1,1,2-trimethyl-propyl ester for chloromethyl carbonic acid 1-methyl ester, but allow the reaction to proceed overnight. Obtain the title compound as a solid: MS 412(M+H).

Example 65

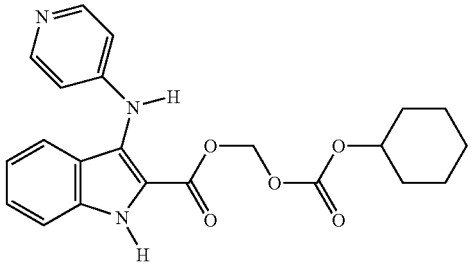

Scheme F:
3-(Pyridin-4-ylamino)-1H-indole-2-carboxylic acid cyclohexyloxycarbonyloxymethyl ester Intermediate: Carbonic acid chloromethyl ester 1,1,2-trimethyl-propyl ester Follow the procedure of Example 62, substituting cyclohexanol for isopropyl alcohol to obtain the title compound.

Step F4: 3-(Pyridin-4-ylamino)-1H-indole-2-carboxylic acid cyclohexyloxycarbonyloxymethyl ester Follow the procedure of Example 62 substituting chloromethyl cyclohexyl carbonate for chloromethyl carbonic acid 1-methyl ester, but allow the reaction to proceed overnight. Obtain the title compound as a solid: MS 410 (M+H).

Example 66

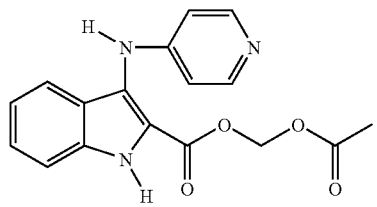

Scheme F

Step F4: 3-(Pyridin-4-ylamino)-1H-indole-2-carboxylic acid acetoxymethyl ester

Stir at 50° C. for 10 min. a mixture of 3-(4-pyridinylamino)-1H-indole-2-carboxylic acid (1.27 g, 5 mmol) in DMF (25 mL), and add $Cs_2CO_3$ (1.63 g, 5 mmol). After 10 min. add bromomethyl acetate (0.95 g, 6.21 mmol) and one minute thereafter quench into aqueous $NH_4Cl$ solution. Extract with EtOAc and wash the extract with aqueous $NaHCO_3$ solution. Dry the extract ($MgSO_4$), filter and concentrate under vacuum to give a solid. Triturate the solid with EtOAc and obtain the title compound as a solid: MS 326(M+H).

Example 67

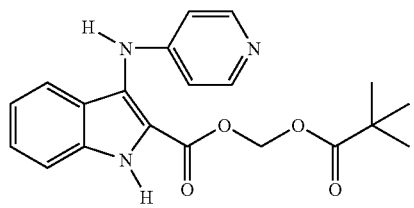

Scheme F

Step F2: 3-(Pyridin-4-ylamino)-1H-indole-2-carboxylic acid 2,2-dimethyl-propionyloxymethyl ester Stir at 50° C. a mixture of 3-(4-pyridinylamino)-1H-indole-2-carboxylic acid potassium salt (1.0 g, 3.43 mmol), KI (0.16 g) 2,2-dimethyl-propionic acid chloromethyl ester (0.63 g, 4.16 mmol) in DMF (20 mL) for 1.5 h. Cool, and partition between $H_2O$-EtOAc. Wash the extract with aqueous $NaHCO_3$ solution, dry the extract ($MgSO_4$), filter and concentrate under vacuum to afford the crude product. Chromatography the product on a silica gel column eluting with 8% MeOH/EtOAc to obtain 0.64 g of the title compound as a solid; MS 326(M+H), m.p. 223–224° C. TLC (silica gel, 8% MeOH/EtOAc) $R_f$=0.30.

Example 68

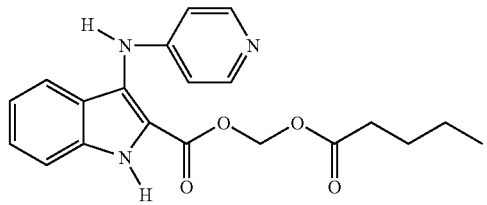

Scheme F

Step F2: 3-(Pyridin-4-ylamino)-1H-indole-2-carboxylic acid pentanoyloxymethyl ester Follow the procedure of Example 67 except substitute pentanoic acid chloromethyl ester for 2,2-dimethyl-propionic acid chloromethyl ester and allow the reaction to proceed at 50° C. overnight. Purify by column chromatography on silica eluting with 5% MeOH/EtOAc to obtain the title compound: MS 368(M+H).

Example 69

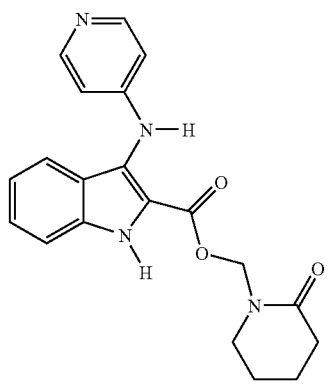

Scheme F: 3-(Pyridin-4-ylamino)-1H-indole-2-carboxylic acid 2-oxo-piperidin-1-yl-methyl ester Intermediate: N-(chloromethyl)-2-piperidinone The title compound is prepared in accordance with the procedures set forth in Moreira, R. et al., *Tet. Lett.*, (1994), 35, 7107–7110. Thus, a mixture of 2-piperidinone (1.0 g, 10.09 mmol) and paraformaldehyde (500 mg) is refluxed in anhydrous THF (30 mL) and chlorotrimethylsilane (30 mL) overnight under $N_2$. Concentrate the solvent under vacuum to give N-(chloromethyl)-2-piperidone as an oil (1.30 g).

Step F2: 3-(Pyridin-4-ylamino)-1H-indole-2-carboxylic acid 2-oxo-piperidin-1-ylmethyl ester Heat at 50° C. a suspension of 3-(4-pyridinylamino)-1H-indole-2-carboxylic acid potassium salt (1.6 g, 5.49 mmol) in anhydrous THF (30 mL) in an oil bath for 20 min. Add a solution of N-(chloromethyl)-2-piperidone (850 mg, 5.76 mmol) in anhydrous THF (5 mL) dropwise. After 30 min, cool the reaction to ambient temperature. Add water (100 mL), and extract with ethyl acetate (3×100 mL). Combine the organic layers, wash with NaHCO₃ (sat), water, brine, dry with MgSO₄ and then concentrate. Purify the residue on an ISCO RediSep 35 gram silicagel cartridge, eluting with 5% methanol in ethyl acetate then 20% methanol in ethyl acetate. Combined product containing fractions and, concentrate to give the title compound as a white solid (520 mg, 26%): MS 365 (M+H), TLC (silica gel, MeOH/EtOAc 25:75) R$_f$=0.18, ¹H NMR (DMSO-d6) δ 11.77 (1H, s), 8.46 (1H, s), 8.08 (2H, d, J=5.7 Hz), 7.50 (3H, m), 7.09 (1H, m), 6.58 (2H, d, J=6 Hz), 5.54 (2H, s), 3.27 (2H, br2), 2.23 (2H, brs), 1.66 (4H, brs). ¹³C NMR (DMSO-d6) δ 170.00, 160.43, 152.25, 149.44, 135.54, 125.60, 122.96, 121.84, 120.22, 119.87, 118.99, 113.00, 108.59, 70.99, 47.00, 31.99, 22.39, 20.60.

Example 70

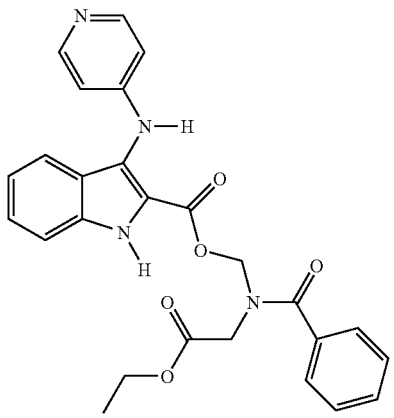

Scheme F: 3-(Pyridin-4-ylamino)-1H-indole-2-carboxylic acid (benzoyl-ethoxycarbonylmethylamino)-methyl ester Intermediate: N-chloromethyl-ethyl benzamidoacetate Reflux a mixture of ethyl benzamidoacetate (1.0 g, 4.83 mmol) and paraformaldehyde (450 mg) in chlorotrimethylsilane (40 mL for overnight under N₂. Concentrate the solvent under vacuum the solvent to give N-chloromethyl-ethyl benzamidoacetate as an oil (1.2 g, 98%).

Step F2: 3-(Pyridin-4-ylamino)-1H-indole-2-carboxylic acid (benzoyl-ethoxycarbonylmethyl-amino)-methyl ester Heat at 50° C. a suspension of 3-(4-pyridinylamino)-1H-indole-2-carboxylic acid potassium salt (1.3 g, 4.46 mmol) in anhydrous THF (20 mL) in an oil bath for 20 min under N₂. Add a solution of N-chloromethyl-ethyl benzamidoacetate (1.2 g, 4.69 mmol) in anhydrous THF (5 mL) dropwise. After 30 min, cool the reaction to ambient temperature. Add water, and extract with ethyl acetate. Wash the organic layer with NaHCO₃ (sat), water, brine, dry with MgSO₄ and then concentrate. Purify the residue on an ISCO RediSep 35 gram silicagel cartridge, eluting with 50% heptane/ethyl acetate (200 mL), 100% ethyl acetate (300 mL) and then 1% methanol/ethyl acetate. Product containing fractions were combined and concentrated to give the title compound as a yellow solid (834 mg): MS 473(M+H), ¹H NMR (DMSO-d6) δ 11.81 (1H, s), 8.47 (1H, s), 8.10 (2H, d, J=5.8 Hz), 7.38 (8H, m), 7.08 (1H, m), 6.66 (2H, J=6.0 Hz), 5.49 (2H, s), 4.30 (2H, s), 4.09 (2H, m), 1.99 (3H, m).). ¹³C NMR (DMSO-d6) δ 171.51, 168.86, 160.30, 152.07, 149.58, 135.72, 134.06, 130.51, 128.46, 127.13, 125.76, 122.65, 122.34, 120.50, 119.90, 118.51, 113.06, 108.89, 74.53, 60.79, 59.74, 47.52, 20.75, 14.07, 13.95.

Example 71

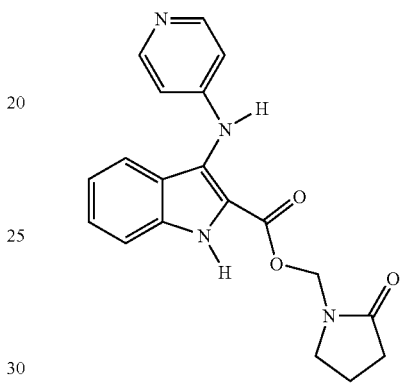

Scheme F: 3-(Pyridin-4-ylamino)-1H-indole-2-carboxylic acid 2-oxo-pyrrolidin-1-ylmethyl ester Intermediate: N-(chloromethyl)-2-pyrrolidinone Reflux a mixture of 2-pyrrolidinone (1.0 g, 11.75 mmol) and paraformaldehyde (500 mg) in chlorotrimethylsilane (40 mL) for 2 hrs under N₂. Evaporate the solvent under vacuum to give N-(chloromethyl)-2-pyrrolidinone as an oil (1.55 g, 99%).

Step F2: 3-(Pyridin-4-ylamino)-1H-indole-2-carboxylic acid 2-oxo-pyrrolidin-1-yl-methyl ester Heated at 50° C. a suspension of 3-(4-pyridinylamino)-1H-indole-2-carboxylic acid potassium salt (2.0 g, 6.86 mmol) in anhydrous THF (100 mL) was oil bath for 20 min. Add to it a solution of N-(chloromethyl)-2-pyrrolidinone (1.10 g, 8.23 mmol) in anhydrous THF (5 mL) dropwise. After 3 hrs, cool the reaction to ambient temperature. Add water (100 mL) and extract with ethyl acetate (3×100 mL). Combine the organic layers and wash with NaHCO₃ (sat), water, brine, dry with MgSO₄ and then concentrate. Purify the residue on an ISCO RediSep 10-gram silicagel cartridge, eluting with ethyl acetate and then 5% methanol in ethyl acetate. Combine product containing fractions and concentrate to give the title compound as an off-yellow solid (205 mg): MS 313(M+H), TLC (silica gel, MeOH/EtOAc 1:1). R$_f$=0.33, ¹H NMR (DMSO-d6) δ 11.78 (1H, s), 8.47 (1H, s), 8.09 (2H, d, J=6.2 Hz), 7.49 (3H, m), 7.09 (1H, m), 6.59 (2H), 5.76 (residual CH₂Cl₂), 5.44 (2H, s), 3.37 (2H, m), 2.22 (2H, m), 1.87 (2H, m).

Example 72

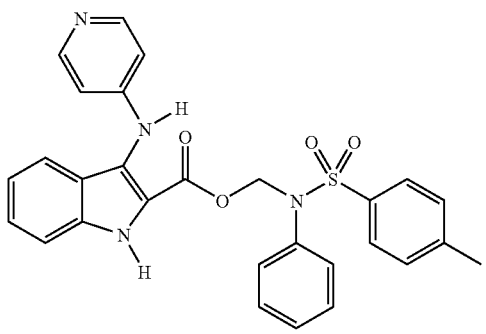

Scheme F: 3-(Pyridin-4-ylamino)-1H-indole-2-carboxylic acid [Phenyl-(Toluene-4-sulfonyl)-amino]-methyl ester Intermediate: N-chloromethyl-N-phenyl-4-methylbenzenesulfonamide The title compound is prepared in accordance with the procedures set forth in Iley, J. et al., *Bioorg. Med. Chem.*, (2000), 8, 1629–1636. Thus, a mixture of N-phenyl-p-toluene sulfonamide (3.0 g, 12.13 mmol) and paraformaldehyde (600 mg) is refluxed in chlorotrimethylsilane (50 mL) for 3 hrs. Concentrate the solvent under vacuum to give N-chloromethyl-N-phenyl-4-methylbenzenesulfonamide as an oil (3.2 g).

Step F2: 3-(Pyridin-4-ylamino)-1H-indole-2-carboxylic acid [Phenyl-(Toluene-4-sulfonyl)-amino]-methyl ester Under $N_2$, at 60° C. dissolve 3-(4-pyridinylamino)-1H-indole-2-carboxylic acid potassium salt (2.2 g, 7.5 mmol) in a mixture of anhydrous THF and DMF (90:10 mL). Cool to 0° C. and add a solution of N-chloromethyl-N-phenyl-4-methylbenzenesulfonamide (2.6 g, 8.80 mmol) in anhydrous THF (5 mL) dropwise. After 20 min add water (100 mL) and then extract with ethyl acetate (4×50 mL). Combine the organic layers, wash with $NaHCO_3$ (sat), water, brine, dry with $Na_2SO_4$ and then concentrate. Purify the residue on an ISCO RediSep 35 gram silicagel cartridge, eluting with ethyl acetate and then 30% methanol/ethyl acetate. Combine product containing fractions and concentrate to a solid. Dissolve the solid in methanol and precipitate with ether to give the title compound as a yellow solid (390 mg): ESI/MS 313 (M+H, $^1$H NMR ($CD_3OD$) δ 8.05 (2H, 2br d, J=6.5 Hz, J=6.8 Hz), 7.38 (14H, m), 6.61 (2H, br d, J=7.0 Hz), 5.93 (2H, s), 2.44 (3H, s).

Example 73

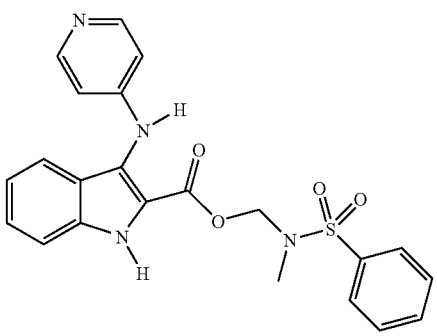

Scheme F: 3-(Pyridin-4-ylamino)-1H-indole-2-carboxylic acid (benzenesulfonyl-methyl-amino)-methyl ester Intermediate: N-chloromethyl-N-methyl-4-methylbenzenesulfonamide Reflux a mixture of N-methylbenzenesulfonamide (2.0 g, 11.68 mmol) and paraformaldehyde (600 mg) in chlorotrimethylsilane (40 mL) for 2.5 hrs. Concentrate under vacuum to give N-chloromethyl-N-methyl-4-methylbenzenesulfonamide as a white solid (2.5 g).

Step F2: 3-(Pyridin-4-ylamino)-1H-indole-2-carboxylic acid (benzenesulfonyl-methyl-amino)-methyl ester Under $N_2$ at 60° C. dissolve 3-(4-pyridinylamino)-1H-indole-2-carboxylic acid potassium salt (2.2 g, 7.55 mmol) in a mixture of anhydrous THF and DMF (150:40 mL). Cool to 0° C. and add N-chloromethyl-N-methyl-4-methylbenzenesulfonamide (2.0 g, 9.10 mmol) in anhydrous THF (10 mL) dropwise. After 20 min., add water (100 mL) and then extract with dichloromethane (3×100 mL). Combine the organic layers wash with $NaHCO_3$ (sat), water, brine, dry with $Na_2SO_4$ and then concentrate. Purify the residue on an ISCO RediSep 35-gram silicagel cartridge, eluting with 50% heptane/ethyl acetate, ethyl acetate and then 10% methanol/ethyl acetate. Combine product containing fractions and concentrate to an oil. Dissolve the oil in methanol and add ether to obtain the title compound as a white solid (800 mg): MS: 437(M+H), $^1$H NMR (DMSO-d6) δ 11.52 (1H, s), 8.29 (1H, s), 8.04 (2H, d, J=5.5 Hz), 7.76 (2H, d, J=7.2 Hz), 7.43 (6H, m), 7.03 (1H, m), 6.46 (2H, d, J=6.0 Hz), 5.60 (2H, s), 2.79 (3H, s).

Example 74

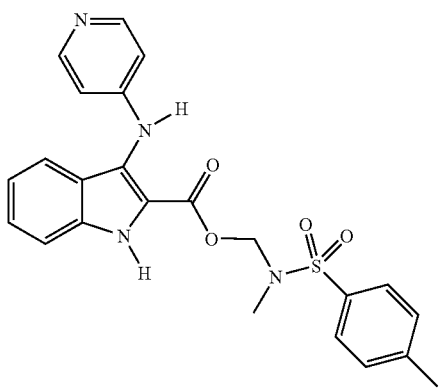

Scheme F: 3-(Pyridin-4-ylamino)-1H-indole-2-carboxylic acid [Methyl-(toluene-4-sulfonyl)-amino]-methyl ester Intermediate: N-chloromethyl-N-methyl-4-methylbenzenesulfonamide Reflux a mixture of N-methyl-4-methylbenzenesulfonamide (2.3 g, 12.4 mmol) and paraformaldehyde (600 mg) in chlorotrimethylsilane (40 mL) for 2 hrs. Concentrate under vacuum to give N-chloromethyl-N-methyl-4-methylbenzenesulfonamide as a white solid (2.8 g).

Step F2: 3-(Pyridin-4-ylamino)-1H-indole-2-carboxylic acid [Methyl-(toluene-4-sulfonyl)-amino]-methyl ester Under $N_2$ at 60° C. dissolve 3-(4-pyridinylamino)-1H-indole-2-carboxylic acid potassium salt (2.0 g, 6.89mmol) in a mixture of anhydrous THF and DMF (60:10 mL Cool to –5° C. add piperidinomethyl polystyrene HL resin (NOVA #01-64-0212, 30 mg) and follow with a solution of N-chloromethyl-N-methyl-4-methylbenzenesulfonamide (1.9 g, 8.34 mmol) in anhydrous THF (10 mL) dropwise. After 30 min, add water (100 mL) and then extract with dichloromethane (3×50 mL). Combine organic layers, wash with $NaHCO_3$ (sat), water, brine, dry with $MgSO_4$ and then concentrate. Purify the residue on an ISCO RediSep 35-gram silicagel cartridge, eluting with 50% heptane/ethyl acetate, ethyl acetate and then 10% methanol/ethyl acetate. Combine product containing fractions and concentrate to a solid (1.1 g). Wash the solid with methanol/ether, and dry to give the title compound as a white solid (720 mg): TLC (silica gel, EtOAc/MeOH, 8:2), $R_f$=0.49, $^1$H NMR (DMSO-d6) δ 11.47 (1H, s), 8.32 (1H, s), 8.09 (2H, d, J=5.7 Hz), 7.63 (2H, d, J=8.3 Hz), 7.48 (1H, d, J=8.3 Hz), 7.34 (2H, m), 7.14 (3H, m), 6.52 (2H, d, J=6.0 Hz), 5.61 (2H, s), 2.83 (3H, s), 2.05 (3H, s).

Example 75

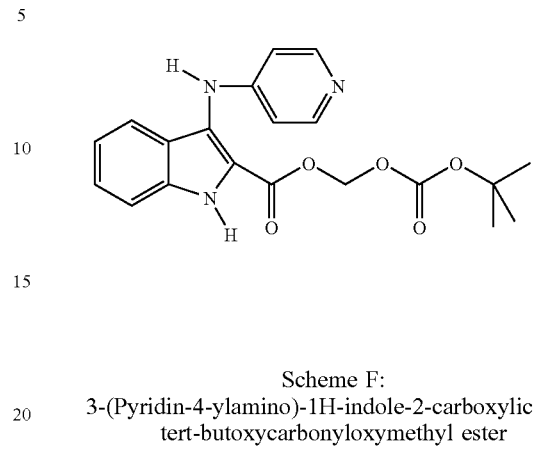

Scheme F:
3-(Pyridin-4-ylamino)-1H-indole-2-carboxylic acid tert-butoxycarbonyloxymethyl ester Intermediate: tert-Butyl chloromethyl carbonate
Follow the procedure of Example 62, substituting tert-butanol for isopropyl alcohol to obtain the title compound.

Step F4: 3-(Pyridin-4-ylamino)-1H-indole-2-carboxylic acid tert-butoxycarbonyloxymethyl ester
Follow the procedure of Example 62 substituting tert-butylchloromethyl carbonate for chloromethyl carbonic acid 1-methyl ester, but allow the reaction to proceed overnight. Obtain the title compound as a solid: MS 384(M+H), HPLC: $R_t$=2.94 min.

Example 76

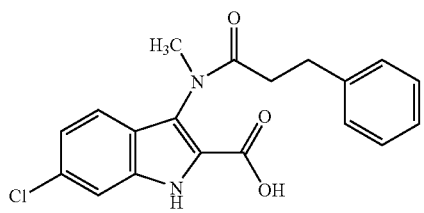

3-((3-Phenylpropanoyl)methylamino)-1H-6-chloro-indole-2-carboxylic acid

Stir at room temperature for overnight a solution of 3-((3-phenylpropanoyl)methylamino)-1H-6-chloro-indole-2-carboxylic acid ethyl ester (213 mg, 0.55 mmol) and lithium hydroxide (35 mg, 0.83 mmol) dissolved in a solvent mixture of 5 mL of THF and 5 mL of water. Dilute the reaction mixture with water (10 mL) and wash with ethyl acetate to remove any organic impurities. Acidify the aqueous layer with 1N hydrochloric acid to precipitate the title compound. Isolate the title compound by filtration and dry at 60° C. under vacuum, yield 197 mg (99% yield); mp 220°–221° C.

Example 77

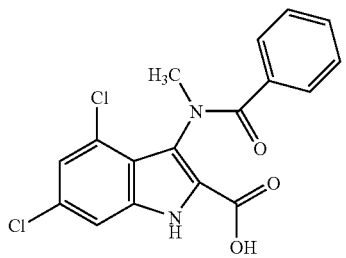

3-((Benzoyl)methylamino)-4,6-dichloro-1H-indole-2-carboxylic acid

Following the procedures as set forth in Example 11 of the U.S. Pat. No. 5,675,018, the title compound is prepared; mp 275° C.

Example 78

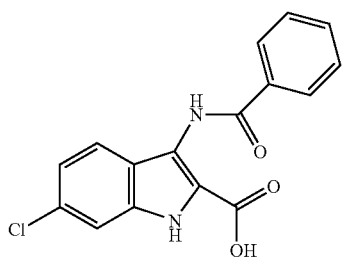

3-((Benzoyl)amino)-6-chloro-1H-indole-2-carboxylic acid

Following the procedures as set forth in Example 4 of the U.S. Pat. No. 5,675,018, the title compound is prepared; mp 205°–210° C. (dec).

Example 79

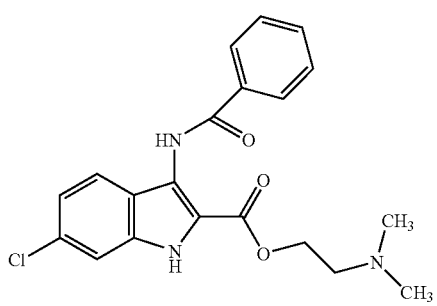

3-((Benzoyl)amino)-6-chloro-1H-indole-2-carboxylic acid 2-dimethylamino-ethyl ester Following the procedures as set forth in Example 5 of the U.S. Pat. No. 5,675,018, the title compound is prepared.

Example 80

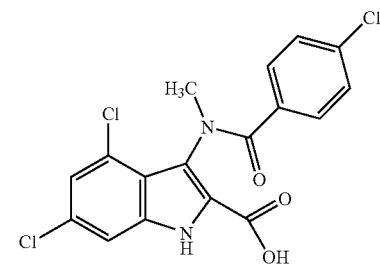

3-((4-chlorobenzoyl)methylamino)-4,6-dichloro-1H-indole-2-carboxylic acid

Following the procedures as set forth in Example 28Q of the U.S. Pat. No. 5,675,018, the title compound is prepared; mp 279°–283° C. Anal. Calcd for $C_{17}H_{11}Cl_3N_2O_3$: C, 51.35; H, 2.79: N, 7.04; Found: C, 51.30; H, 2.81; N, 7.00.

Example 81

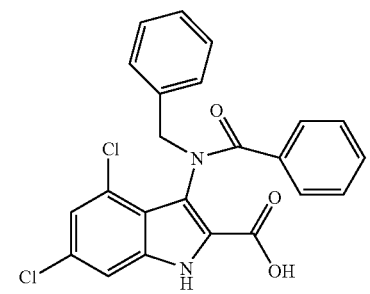

3-((Benzoyl)benzylamino)-4,6-dichloro-1H-indole-2-carboxylic acid

Following the procedures as set forth in Example 17 of the U.S. Pat. No. 5,675,018, the title compound is prepared; mp 266°–267° C.

Example 82

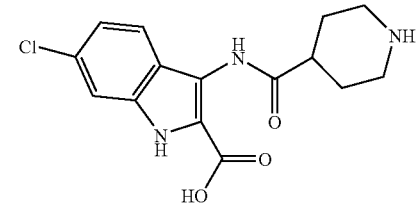

3-((4-Piperdineacyl)amino)-6-chloro-1H-indole-2-carboxylic acid

Following the procedures as set forth in the U.S. Pat. No. 5,675,018, the title compound is prepared.

Example 83

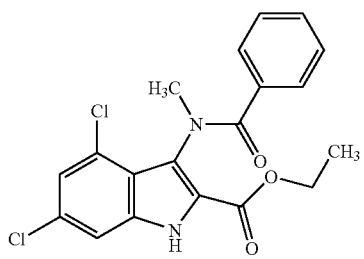

3-((Benzoyl)methylamino)-4,6-dichloro-1H-indole-2-carboxylic acid ethyl ester The title compound is prepared following the procedures as set forth in Example 10 of the U.S. Pat. No. 5,675,018; mp 143°–144° C.

Example 84

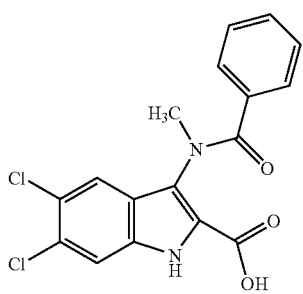

3-((Benzoyl)methylamino)-5,6-dichloro-1H-indole-2-carboxylic acid

The title compound is prepared following the procedures as set forth in Example 41c of the U.S. Pat. No. 5,675,018.

Example 85

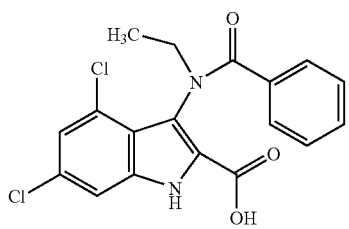

3-((Benzoyl)ethylamino)-4,6-dichloro-1H-indole-2-carboxylic acid

The title compound is prepared following the procedures as set forth in Example 15 of the U.S. Pat. No. 5,675,018; mp 254°–256° C.

Example 86

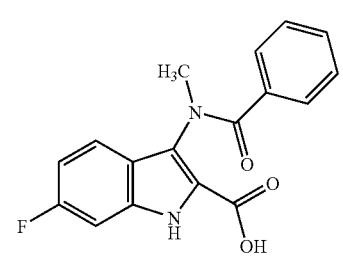

3-((Benzoyl)methylamino)-6-fluoro-1H-indole-2-carboxylic acid

The title compound is prepared following the procedures as set forth in Example 4L of the U.S. Pat. No. 5,675,018; mp 142°–143° C. Anal. Calcd for $C_{11}H_{13}FN_2O_3$: C, 55.00; H, 5.45: N, 11.66; Found: C, 55.09; H, 5.19; N, 11.63.

Example 87

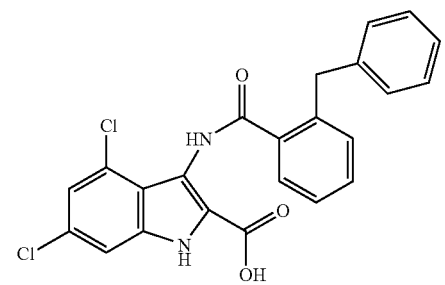

3-((2-Benzylbenzoyl)amino)-4,6-dichloro-1H-indole-2-carboxylic acid

The title compound is prepared following the procedures as set forth in Example 21 of the U.S. Pat. No. 5,675,018; mp 234°–235° C. Anal. Calcd for $C_{23}H_{16}Cl_2N_2O_3$: C, 62.88; H, 3.67: N, 6.38; Found: C, 63.04; H, 4.05; N. 5.97.

Example 88

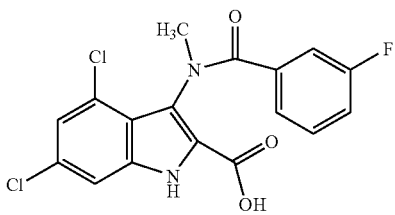

3-((3-Fluorobenzoyl)methylamino)-4,6-dichloro-1H-indole-2-carboxylic acid

The title compound is prepared following the procedures as set forth in Example 28j of the U.S. Pat. No. 5,675,018; mp 270°–280° C. Anal. Calcd for $C_{17}H_{11}Cl_2FN_2O_3$: C, 53.57; H, 2.91: N, 7.35; Found: C, 53.54; H, 3.15; N, 7.24.

Example 89

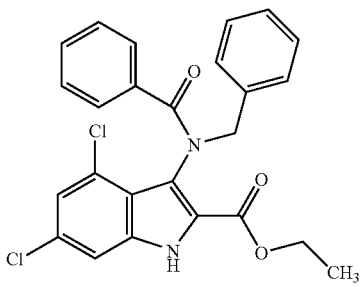

3-((Benzoyl)benzylamino)-4,6-dichloro-1H-indole-2-carboxylic acid ethyl ester

The title compound is prepared following the procedures as set forth in Example 16 of the U.S. Pat. No. 5,675,018; mp 174°–175° C.

Example 90

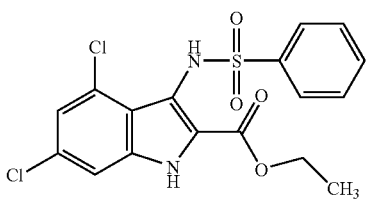

3-((Phenylsulfonyl)amino)-4,6-dichloro-1H-indole-2-carboxylic acid ethyl ester

The title compound is prepared following the procedures as set forth in Example 29 of the U.S. Pat. No. 5,675,018; mp 245°–247° C.

Example 91

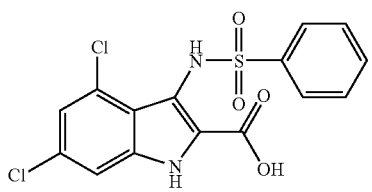

3-((Phenylsulfonyl)amino)-4,6-dichloro-1H-indole-2-carboxylic acid

The title compound is prepared following the procedures as set forth in Example 30 of the U.S. Pat. No. 5,675,018; mp 229°–235° C.

Example 92

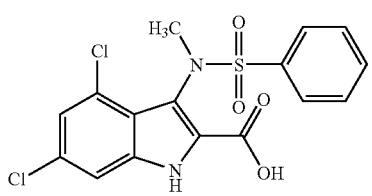

3-((Phenylsulfonyl)methylamino)-4,6-dichloro-1H-indole-2-carboxylic acid

The title compound is prepared following the procedures as set forth in Example 32 of the U.S. Pat. No. 5,675,018; mp 286°–290° C.

Examples 93–112

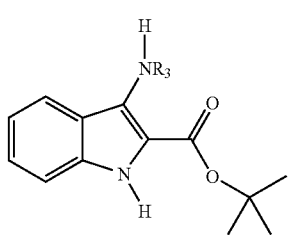

Parallel Synthesis of 1H-Indole-2-carboxylic acid-3-[(carbonyl)amino]tert-butyl esters Charge a reaction vessel with 3-amino-1H-indole-2-carboxylic acid tert-butyl ester (100 mg), the appropriate chloroformate (0.5 mmol), polymer bound diisopropylethylamine (200 mg) and place on a Quest 210 parallel synthetic apparatus and stir overnight. Add tris amine (generally in excess amounts of about 2 to 5 molar equivalents), filter, and concentrate under vacuum to obtain the title compounds.

Table 14 lists the reactant chloroformate, the resulting product and the associated analytical data for the product.

TABLE 14

| Example | Chloroformate R = | Product R₃ = | MS (M + H) | HPLC (min)[a] |
|---|---|---|---|---|
| 93 | *tert*-butyl | tert-butyl carbonate | 333 | 2.11 |
| 94 | —O—(CH₂)₃CH₃ | —C(O)O—(CH₂)₃CH₃ | 333 | 2.15 |
| 95 | —C₂H₅ | —C(O)O—C₂H₅ | 305 | 1.95 |
| 96 | 4-nitrobenzyl | —C(O)O-CH₂-C₆H₄-NO₂ | 412 | 2.06 |
| 97 | allyl | —C(O)O-allyl | 317 | 1.97 |
| 98 | menthyl | menthyl carbonate | — | 2.64 |
| 99 | —(CH₂)₂CH₃ | —C(O)O—(CH₂)₂CH₃ | 319 | 2.05 |
| 100 | —CH(C₂H₅)(CH₂)₃CH₃ | —C(O)O—CH(C₂H₅)(CH₂)₃CH₃ | 389 | 2.5 |
| 101 | —(CH₂)₅CH₃ | —C(O)O—(CH₂)₅CH₃ | 361 | 2.35 |
| 102 | 4-nitrophenyl | —C(O)O-C₆H₄-OMe | 383 | 2.05 |
| 103 | 4-bromophenyl | —C(O)O-C₆H₄-Br | — | 2.21 |

TABLE 14-continued
| Example | Chloroformate R = | Product R₃ = | MS (M + H) | HPLC (min)[a] |
|---|---|---|---|---|
| 104 |  | 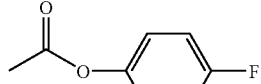 | — | 1.88 |
| 105 | 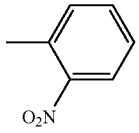 | 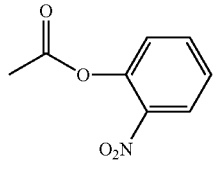 | — | — |
| 106 | 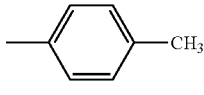 | 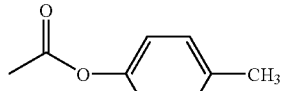 | — | 2.61 |
| 107 | 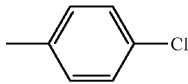 | 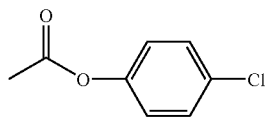 | — | 2.07 |
| 108 | 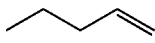 | 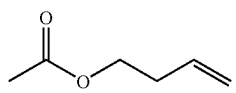 | 331 | 2.16 |
| 109 | 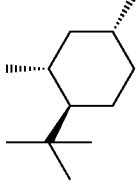 | 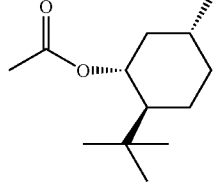 | — | 2.13 |
| 110 | 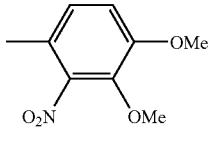 | 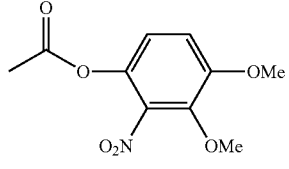 | — | — |
| 111 | 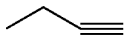 | 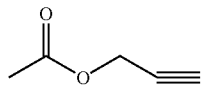 | 315 | 2.06 |
| 112 | 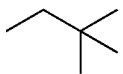 | 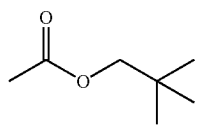 | — | 2.18 |
[a] retention time in minutes

Examples 113–119

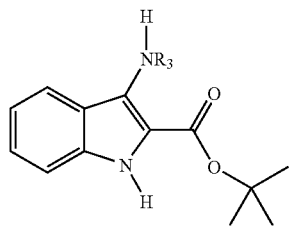

Synthesis of 3-(Sulfonyl)amino-1H-Indole-2-carboxylic acid tert-butyl esters

General Method (Examples 113 to 118)

Dissolve 3-amino-1H-indole-2-carboxylic acid tert-butyl ester (0.43 mmol) in dichloromethane (1 mL), add N-methylmorpholine (0.2 mL), and then the appropriate sulfonyl chloride (0.5 mmol) dissolved in dichloromethane (1 mL). Stir overnight, and partition between 1N NaOH and dichloromethane. Separate the organic layer and wash with aqueous $NH_4Cl$. Dry the organic layer over $MgSO_4$, filter and concentrate under vacuum and obtain the title compounds.

General Method (Example 119)

Dissolve 3-amino-1H-indole-2-carboxylic acid tert-butyl ester (0.43 mmol) in dichloromethane (2 mL), add N-methylmorpholine (0.2 mL), and then the appropriate sulfonyl chloride (0.5 mmol) dissolved in dichloromethane (1 mL). Shake on a JKEM block apparatus for 4 h at ambient temperature. Quench the reaction with saturated $NH_4Cl$ solution, separate the organic layer and evaporate under vacuum. Dissolve the resulting solid in dichloromethane, filter and evaporate the filtrate under vacuum to obtain the title compounds.

Table 15 lists the reactant sulfonyl chloride, the resulting product and the associated analytical data for the product.

TABLE 15

| Example | Sulfonyl chloride R = | Product $R_3$ | MS (M + H) | HPLC (min)[a] |
|---|---|---|---|---|
| 113 | (styryl) | (styrylsulfonyl) | 399 | 2.27 |
| 114 | (4-((4-dimethylaminophenyl)azo)phenyl) | (4-((4-dimethylaminophenyl)azo)phenylsulfonyl) | 520 | 2.28 |
| 115 | (4-methylnaphthyl) | (naphthylsulfonyl) | 423 | 2.08 |
| 116 | (camphorsulfonyl) | (camphorsulfonyl) | — | — |
| 117 | (2-acetamidothiazolyl) | (2-acetamidothiazolylsulfonyl) | 451 | 1.8 |

TABLE 15-continued

| Example | Sulfonyl chloride R = | Product $R_3$ | MS (M + H) | HPLC (min)[a] |
|---|---|---|---|---|
| 118 |  | 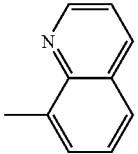 | — | — |
| 119 | 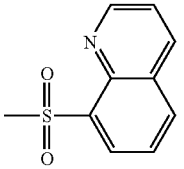 | 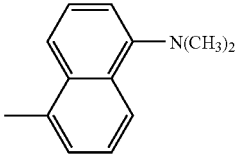 | 466 | 2.16 |

[a] retention time in minutes;
[b] melting point = 179–181° C.

Examples 120–124

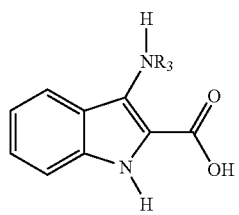

Synthesis of 3-(Substituted Sulfonyl)amino-1H-Indole-2-carboxylic acids

General Method

Dissolve a 3-(substituted sulfonyl)amino-1H-Indole-2-carboxylic acid tert-butyl ester in dichloromethane (2 mL), add trifluoroacetic acid (1 mL), and stir at ambient temperature for 2 h. Concentrate the reaction mixture under vacuum and partition the residue between EtOAc and water. Collect the organic layer and dry over MgSO₄ filter, concentrate under vacuum and obtain the title compounds.

Alternatively, for Examples 123 and 124 concentrate the reaction under vacuum, and triturate the residue with ether. Filter and collect the product as a trifluoroacetic acid salt.

Table 16 lists the 3-(substituted sulfonyl)amino-1H-Indole-2-carboxylic acids and the associated analytical data.

TABLE 16

| Example | Product $R_3$ | MS (M + H) | HPLC (min)[a] |
|---|---|---|---|
| 120 | 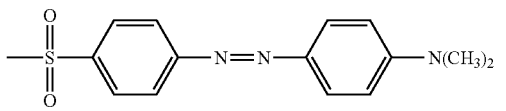 | 464 | 1.95 |
| 121 | 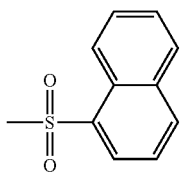 | 367 | 1.72 |

TABLE 16-continued

| Example | Product R₃ | MS (M + H) | HPLC (min)[a] |
|---|---|---|---|
| 122 | (structure: methylsulfonyl-camphor derivative) | 391 | 1.65 |
| 123 | (structure: methylsulfonyl-thiazole-acetamide) ·CF₃COOH | 395 | 1.52 |
| 124 | (structure: methylsulfonyl-quinoline) ·CF₃COOH | 368 | 1.58 |

[a]retention time in minutes

Example 125

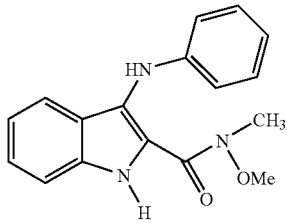

3-(Pyridin-4-ylamino)-1H-indole-2-carboxylic acid methoxy-methyl-amide

To a solution of 3-(pyridin-4-ylamino)-1H-indole-2-carboxylic acid (1.77 g, 7.0 mmol) in DMF (15 mL) stirred at room temperature is added a coupling agent, 1,1'-carbonyldiimidazole (CDI) (1.13 g, 7 mmol) and the stirring is continued for about 30 to 40 minutes. Then, N-methoxy-N-methylamine hydrochloride (680 mg, 7 mmol) is added and the reaction mixture is allowed to stir overnight. The reaction is monitored by TLC (silicagel, dichloromethane/methanol 7:3, v/v). The starting material is consumed after overnight stirring. Add aqueous NH₄Cl solution, ethyl acetate and brine. Filter the solid that is formed and discard. Extract the aqueous layer several times with ethyl acetate. Purify the extracts by flash chromatography using dichloromethane/methanol to obtain 300 mg (15%) of yellow amorphous solid of the title compound. The NMR and LC-MS data are in agreement with the expected data for the title compound.

Example 126

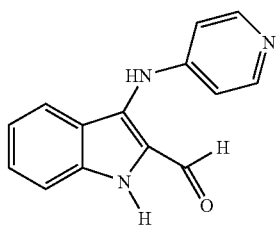

3-(Pyridin-4-ylamino)-1H-indole-2-carboxaldehyde

At 0° C. stir a suspension of 3-(pyridin-4-ylamino)-1H-indole-2-carboxylic acid methoxy-methyl-amide (2.72 g, 7.2 mmol) in THF (35 mL), and add a 1M solution of LAH in THF (14.5 mL, 14.5 mmol). Allow warming to room temperature and continue to stir for 20 h. Add aqueous NH₄Cl followed by dichloromethane. Filter the aluminum salts, separate the organic phase and concentrate it under vacuum to obtain a brown oil. Flash chromatograph the oil to obtain 0.62 g (36%) of the title compound as a yellow solid. $^1$H NMR (DMSO-d6) δ 11.8 (1H, s), 9.95 (1H, s), 9.1 (1H, s), 8.18 (2H, brs), 7.4 (3H, m), 7.1 (1H, dd), 6.7 (2H, brd).

Example 127

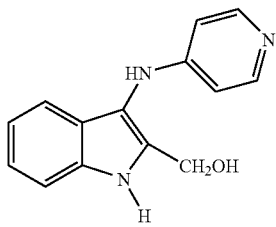

[3-(Pyridin-4-ylamino)-1H-indol-2-yl]-methanol

At 0° C. stir a solution of 3-(pyridin-4-ylamino)-1H-indole-2-carboxylic acid ethyl ester (1.4 g, 5 mmol) in THF (15 mL) and add a 1M solution of LAH in THF (8 mL, 8 mmol). Allow the reaction to warm to room temperature and stir for an additional 0.5 h. Add aqueous NH$_4$Cl solution, ethyl acetate and brine. Filter the solid that forms in the biphasic mixture to obtain 0.56 g (47%) of the title compound as a beige solid: MS 240(M+H); HPLC: R$_t$=1.04 min; TLC (silica gel, dichloromethane/MeOH, 4:1), R$_f$=0.6.

Example 128

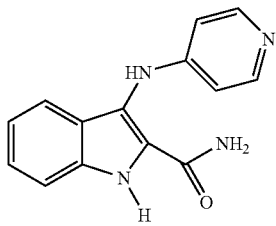

3-(Pyridin-4-ylamino)-1H-indole-2-carboxamide

At −20° C. stir a solution of 3-(pyridin-4-ylamino)-1H-indole-2-carboxylic acid (1.26 g, 3.0 mmol) in DMF (12 mL) and add BOP (1.32 g, 3.0 mmol) and then diisopropylethylamine (0.8 mL, 4.5 mmol). Stir the reaction for 0.25 h and add a solution of 7M NH$_3$ in MeOH (0.43 mL, 3.0 mmol). Allow the reaction to stir at room temperature overnight and add EtOAc. Wash the organic solution with aqueous NaHCO$_3$, brine and dry over MgSO$_4$. Filter and concentrate the filtrate under vacuum to obtain a solid. Recrystallize the solid from EtOAc to obtain 0.425 g of the title compound as a yellow solid: MS 253(M+H); m.p. 230° C. (decomposition); TLC (silica gel, dichloromethane/MeOH/NH$_4$OH, 8:2:0.1 v/v), R$_f$=0.39.

Example 129

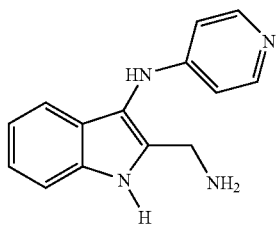

(2-Aminomethyl-1H-indol-3-yl)-pyridin-4-yl-amine

At 0° C. stir a solution of 3-(pyridin-4-ylamino)-1H-indole-2-carboxamide (1.26 g, 5 mmol) in THF (10 mL) and add dropwise a 1M solution of LAH in THF (25 mL, 25 mmol). Allow the reaction to warm to room temperature and then reflux overnight. Add aqueous 10% Rochelle salt solution, and extract the aqueous mixture with EtOAc. Concentrate the extract under vacuum and isolate 0.5 g of crude yellow solid. Purify the solid by preparative HPLC and obtain 0.2 g of the title compound as a solid: MS 239(M+H).

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A compound of the formula (I):

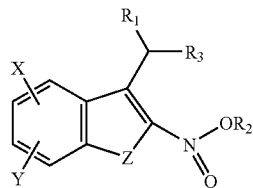

(I)

wherein

X and Y are the same or different and are independently selected from the group consisting of hydrogen, halogen, nitro, amino, hydroxy, $C_{1-6}$alkyl, $C_{2-6}$alkenyl, $C_{2-6}$alkynyl, $C_{1-6}$alkoxy, $C_{1-6}$perfluoroalkyl, $C_{1-6}$perfluoroalkoxy, phenyl and benzyl, wherein phenyl or benzyl is optionally substituted with one or two substituents each independently selected from $C_{1-6}$alkyl, $C_{1-6}$perfluoroalkyl, halogen, hydroxy or $C_{1-6}$perfluoroalkyl or $C_{1-6}$perfluoroalkoxy;

Z is N—R, wherein R is selected from the group consisting of hydrogen, $C_{1-6}$alkyl, $C_{1-6}$alkylcarbonyl, $C_{1-6}$alkoxycarbonyl$C_{1-6}$alkyl, $C_{1-6}$alkylcarbamoyl-$C_{1-6}$alkyl and $C_{1-6}$dialkylcarbamoyl$C_{1-6}$alkyl;

$R_1$ is selected from the group consisting of hydrogen, $C_{1-6}$alkyl, $C_{2-6}$alkeny, $C_{2-6}$alkynyl, $C_{1-6}$perfluoroalkyl, $C_{3-8}$cycloalkyl, $C_{3-8}$cycloalkyl$C_{1-6}$alkyl, $C_{1-6}$alkoxy$C_{1-6}$alkyl, hydroxy$C_{1-6}$alkyl, amino$C_{1-6}$alkyl, mono- or di-$C_{1-6}$alkyl-amino$C_{1-6}$alkyl, formyl, $C_{1-6}$alkylcarbonyl, amino$C_{1-6}$alkylcarbonyl, C$_{1-6}$alkoxycarbonyl, phenyl, diphenylC$_{1-6}$alkyl and phenylC$_{1-6}$alkyl, phenylcarbonylC$_{1-6}$alkyl, phenoxyC$_{1-6}$alkyl, wherein phenyl is optionally substituted with one or two substituents each independently selected from C$_{1-6}$alkyl, C$_{1-6}$perfluoroalkyl, halogen, hydroxy or C$_{1-6}$perfluoroalkyl or C$_{1-6}$perfluoroalkoxy;

R$_3$ is

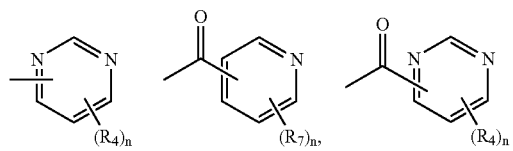

wherein

R$_4$ is selected form the group consisting of hydrogen, halogen, nitro, amino, hydroxy, C$_{1-6}$alkyl, C$_{1-6}$alkoxy, C$_{1-6}$perfluoroalkyl, C$_{1-6}$perfluoroalkoxy, N-morpholinylcarbonyl, phenyl and benzyl, wherein phenyl or benzyl is optionally substituted with one or two substituents each independently selected from C$_{1-6}$alkyl, C$_{1-6}$perfluoroalkyl, halogen, hydroxy, C$_{1-6}$alkoxy or C$_{1-6}$perfluoroalkoxy;

R$_7$ is selected from the group consisting of halogen, nitro, amino, hydroxy, C$_{1-6}$alkyl, C$_{1-6}$alkoxy, C$_{1-6}$perfluoroalkyl, C$_{1-6}$perfluoroalkoxy, N-morpholinylcarbonyl, phenyl and benzyl, wherein phenyl or benzyl is optionally substituted with one or two substituents each independently selected from C$_{1-6}$alkyl, C$_{1-6}$perfluoroalkyl, halogen, hydroxy, C$_{1-6}$alkoxy or C$_{1-6}$perfluoroalkoxy; and n is an integer from 0 to 3; and R$_2$ is selected from the group consisting of hydrogen, C$_{1-6}$alkyl, C$_{1-6}$perfluoroalkyl, perfluoroaryl, indanyl, C$_{1-6}$alkoxyC$_{1-6}$alkyl, C$_{2-6}$acyloxyC$_{1-6}$alkyl, C$_{1-6}$alkoxycarbonylC$_{1-6}$alkyl, C$_{1-6}$alkoxycarbonyloxyC$_{1-6}$alkyl, C$_{1-6}$cycloalkyl, C$_{3-8}$cycloalkoxycarbonyloxy-C$_{1-6}$alkyl, adamantyloxycarbonyloxyC$_{1-6}$alkyl, C$_{3-8}$cycloalkoxycarbonyl-C$_{1-6}$alkyl, mono- or di-C$_{1-6}$alkylamino-C$_{1-6}$alkyl, C$_{3-8}$azacycloalkylC$_{1-6}$alkyl, mono- or di-C$_{1-6}$alkylcarbamoyl-C$_{1-6}$alkyl, C$_{3-8}$azacycloalkylcarbonyloxyC$_{1-6}$alkyl, benzylC$_{1-6}$alkylcarbamoylC$_{1-6}$alkyl, mono- or di-C$_{1-6}$alkylcarbamoyloxyC$_{1-6}$alkyl, C$_{3-8}$azacycloalkylcarbonyloxyC$_{1-6}$alkyl, benzylC$_{1-6}$alkylcarbamloxyC$_{1-6}$alkyl, benzycarbamoyloxyC$_{1-6}$alkyl, C$_{1-6}$alkoxycarbonylamino-oxo-$_{1-6}$alkyl,

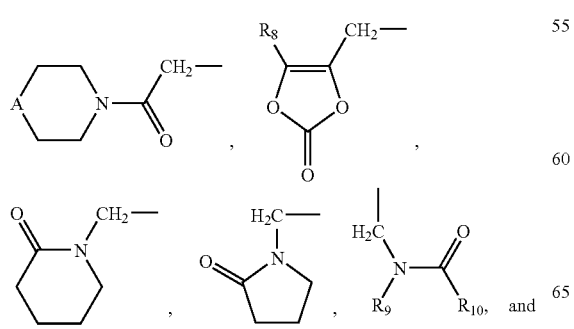

-continued

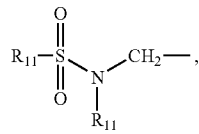

wherein

R$_8$ is hydrogen or C$_{1-6}$alkyl,

R$_9$ is C$_{1-6}$alkyl or phenyl,

R$_{10}$ is hydrogen, C$_{1-6}$alkyl or C$_{1-6}$alkoxycarbonylC$_{1-6}$alkyl,

R$_{11}$ is C$_{1-6}$alkyl, phenyl or tolyl, and

A is CH$_2$, NH or O, or a pharmaceutically acceptable salt thereof, with the proviso that when Z is N—R, and when both X and Y are hydrogen, R$_2$ is not hydrogen or C$_{1-6}$alkyl; and with the proviso tat when R$_3$ is

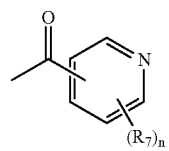

n is 1 to 3.

2. The compound as set forth in claim 1 wherein R$_3$ is

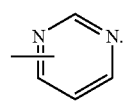

3. The compound as set forth in claim 2, which is 3-(pyrimidin-2-ylamino)-1H-indole-2-carboxylic acid, ethyl ester.

4. The compound as set forth in claim 1 wherein R$_3$ is

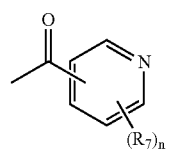

and wherein

R$_7$ is chloro, methyl, methoxy or N-morpholinylcarbonyl, and n is 1 or 2.

5. The compound as set forth in claim 4 which is selected from the group consisting of:
  3-(2-chloro-pyridine-4-carbonyl)-amino-3H-indale-2-carboxylic acid ethyl ester,
  3-(2,6-dichloro-pyridine-4-carbonyl)-amino-3H-indole-2-carboxylic acid ethyl ester,
  3-(2-chloro-6-methyl-pyridine-4-carbonyl)-amino-3H-indole-2-carboxylic acid ethyl ester,
  3-(2-chloro-6-methoxy-pyridine-4-carbonyl)-amino-3H-indole-2-carboxylic acid ethyl ester, 3-(2-chloro-pyridine-4-carbonyl)-amino-3H-indol2-carboxylic acid tert-butyl ester, 3-(2,6-dichloro-pyridine-4-carbonyl)-amino-3H-indole-2-carboxylic acid tert-butyl ester, 3-(2-chloro-6-methoxy-pyridine-4-carbonyl)-amino-3H-indole-2-carboxylic acid tert-butyl ester, and 3-{[(6-morpholine-4-carbonyl)-pyridine-3-carbonyl]-amino}-3H-indole-2-carboxylic acid ethyl ester.

6. A compound of the formula (II):

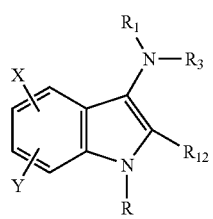

(II)

wherein

X and Y are the same or different and are independently selected from the group consisting of hydrogen, halogen, nitro, amino, hydroxy, $C_{1-6}$alkyl, $C_{1-6}$alkenyl, $C_{2-6}$alkynyl, $C_{1-6}$alkoxy, $C_{1-6}$perfluoroalkyl, $C_{1-6}$perfluoroalkoxy, phenyl and benzyl, wherein phenyl or benzyl is optionally substituted with one or two substituents each independently selected from $C_{1-6}$alkyl, $C_{1-6}$perfluoroalkyl, halogen, hydroxy or $C_{1-6}$perfluoroalkyl or $C_{1-6}$perfluoroalkoxy;

R is selected from the group consisting of hydrogen, $C_{1-6}$alkyl, $C_{1-6}$alkylcarbonyl. $C_{1-6}$alkoxycarbonyl$C_{1-6}$alkyl, $C_{1-6}$alkylcarbamoyl-$C_{1-6}$alkyl and $C_{1-6}$alkylcarbamoyl$C_{1-6}$alkyl;

$R_1$ is selected from the group consisting of hydrogen. $C_{1-6}$alkyl, $C_{2-6}$alkenyl, $C_{2-6}$alkynyl. $C_{1-6}$perfluoroalkyl, $C_{3-8}$cycloalkyl, $C_{3-8}$cycloalkyl$C_{1-6}$alkyl, $C_{1-6}$alkoxy$C_{1-6}$alkyl, hydroxy$C_{1-6}$alkyl, amino$C_{1-6}$alkyl, mono- or di-$C_{1-6}$alkyl- amino$C_{1-6}$alkyl, formyl, $C_{1-6}$alkylcarbonyl, amino$C_{1-6}$alkylcarbonyl, $C_{1-6}$alkoxycarbonyl,phenyl, diphenyl$C_{1-6}$alkyl and phenyl$C_{1-6}$alkyl, phenylcarbonyl$C_{1-6}$alkyl, phenoxy$C_{1-6}$alkyl, wherein phenyl is optionally substituted with one or two substituents each independently selected from $C_{1-6}$alkyl, $C_{1-6}$perfluoroalkyl, halogen, hydroxy or $C_{1-6}$perfluoroalkyl or $C_{1-6}$perfluoroalkoxy;

$R_3$ is

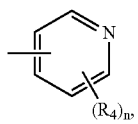

wherein $R_4$ is selected from the group consisting of hydrogen, halogen, nitro, amino, hydroxy, $C_{1-6}$alkyl $C_{1-6}$alkoxy, $C_{1-6}$perfluoroalkyl, $C_{1-6}$perfluoroalkoxy, N-morpholinylcarbonyl, phenyl and benzyl, wherein phenyl or benzyl is optionally substituted with one or more substituents each independently selected from $C_{1-6}$alkyl, $C_{1-6}$perfluoroalkyl, halogen, hydroxy, $C_{1-6}$alkoxy or $C_{1-6}$perfluoroalkoxy;

$R_{12}$ is hydroxymethyl, $C_{1-6}$alkoxymethyl, aminomethyl, mono or di-$C_{1-6}$alkylaminomethyl, —C(O)H, $C_{2-6}$acyloxymethyl, —CN, —CONR$_{13}$R$_{14}$; and

wherein $R_{13}$ and $R_{14}$ are the same or different and are independently selected from hydrogen, $C_{1-6}$alkyl or $C_{1-6}$alkoxy; and $R_{15}$ is hydrogen or $C_{1-6}$alkyl;

or a pharmaceutically acceptable salt thereof.

7. The compound as set forth in claim 6 which is selected from the group consisting of:

3-(pyridin-4-ylamino)-1H-indole-2-carboxylic acid methoxy-methyl-amide, 3-(pyridin-4-ylamino)-1H-indole-2-carboxaldehyde,

[3-(pyridin-4-ylamino)-1H-indol-2-yl]-methanol, 3-(pyridin-4-ylamino)-1H-indole-2-carboxamide, and (2-aminomethyl-1H-indol-3-yl)-pyridin-4-yl-amine.

8. A process for the preparation of a compound of formula 3:

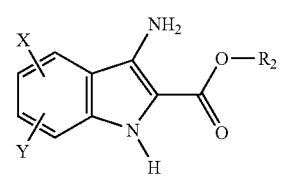

(3)

comprising:

(a) reacting compound of formula (1):

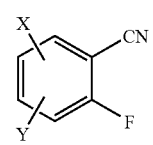

(1)

with compound of formula (2):

NH$_2$CO$_2$R$_2$       (2);

(b) isolating the product; and (c) optionally reacting said compound of formula (3) with an inorganic or organic acid to provide a pharmaceutically acceptable acid addition salt; and wherein X and Y are the same or different and are independently selected from the group consisting of hydrogen, halogen, nitro, amino, hydroxy, $C_{1-6}$alkyl, $C_{2-6}$alkenyl, $C_{2-6}$alkynyl, $C_{1-6}$alkoxy, $C_{1-6}$perfluoroalkyl, $C_{1-6}$perfluoroalkoxy, phenyl and benzyl, wherein phenyl or benzyl is optionally substituted with one or two substituents each independently selected from $C_{1-6}$alkyl, $C_{1-6}$perfluoroalkyl, halogen, hydroxy or $C_{1-6}$perfluoroalkyl or $C_{1-6}$perfluoroalkoxy;

$R_2$ is selected from the group consisting of hydrogen, $C_{1-6}$alkyl, $C_{1-6}$perfluoroalkyl, perfluoroaryl, indanyl, $C_{1-6}$alkoxy$C_{1-6}$alkyl, $C_{2-6}$acyloxy$C_{1-6}$alkyl, $C_{1-6}$alkoxycarbonyl$C_{1-6}$alkyl, $C_{1-6}$alkoxycarbonyloxy$C_{1-6}$alkyl, $C_{3-8}$cycloalkyl, $C_{3-8}$cycloalkoxycarbonyloxy-$C_{1-6}$alkyl, adamantyloxycarbonyloxy$C_{1-6}$alkyl, $C_{3-8}$cycloalkoxycarbonyl-$C_{1-6}$alkyl, mono- or di-$C_{1-6}$alkylamino-$C_{1-6}$alkyl, $C_{3-8}$azacycloalkyl$C_{1-6}$alkyl, mono- or di-$C_{1-6}$alkylcarbamoyl-$C_{1-6}$alkyl, $C_{3-8}$azacycloalkylcarbonyloxy$C_{1-6}$alkyl, benzyl$C_{1-6}$alkylcarbomoyl$C_{1-6}$alkyl, mono- or di-$C_{1-6}$carbamoyloxy$C_{1-6}$alkyl, $C_{3-8}$azacycloalkylcarbonyloxy $C_{1-6}$alkyl, benzyl$C_{1-6}$alkylcarbamoyloxy$C_{1-6}$alkyl, benzylcarbamoyloxy$C_{1-6}$alkyl, $C_{1-6}$alkoxycarbonylamino-oxo-$C_{1-6}$alkyl,

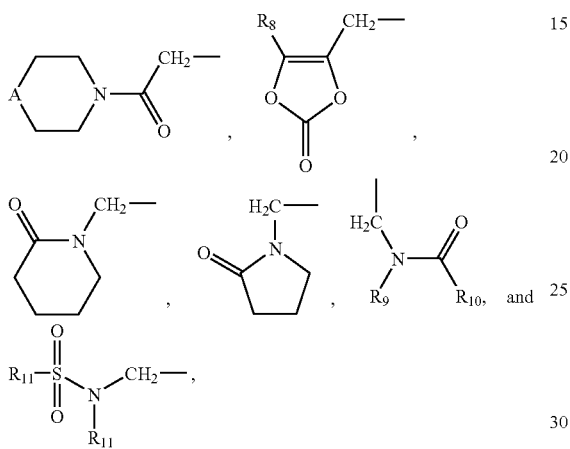

wherein
$R_8$ is hydrogen or $C_{1-6}$alkyl,
$R_9$ is $C_{1-6}$alkyl or phenyl,
$R_{10}$ is hydrogen, $C_{1-6}$alkyl or $C_{1-6}$alkoxycarbonyl$C_{1-6}$alkyl,
$R_{11}$ is $C_{1-6}$alkyl, phenyl or tolyl, and
A is $CH_2$, NH or O.

9. The process as set forth in claim 8 wherein the reaction in step (a) is carried out in the presence of a base.

10. The process as set forth in claim 9 wherein said base is potassium carbonate.

11. A compound selected from the group consisting of:
5,6-dimethoxy-3-(4-pyridinylamino)-1H-indole-2-carboxylic acid, ethyl ester;
6-phenyl-3-(4-pyridinylamino)-1H-indole-2-carboxylic acid, ethyl ester;
3-(4-pyridinylamino)-1H-indole-2-carboxylic acid pentafluorophenyl ester,
3-(4-pyridinylamino)-1H-indole-2-carboxylic acid 2-diethylamino-ethyl ester,
3-(4-pyridinylamino)-1H-indole-2-carboxylic acid 2-dimethylamino-ethyl ester,
3-(4-pyridinylamino)-1H-indole-2-carboxylic acid 2-piperidin-1-yl-ethyl ester,
3-(pyridin-4-ylamino)-1H-indole-2-carboxylic acid (S)-1-methoxycarbonyl-ethyl ester,
3-(pyridin-4-ylamino)-1H-indole-2-carboxylic acid ethoxycarbonylmethyl ester,
3-(4-pyridinylamino)-1H-indole-2-carboxylic acid 2-methoxyethyl ester,
3-(4-pyridinylamino)-1H-indole-2-carboxylic acid 3-ethoxypropyl ester,
3-(pyridin-4-ylamino)-1H-indole-2-carboxylic acid indan-5-yl ester,
3-(pyridin-4-ylamino)-1H-indole-2-carboxylic acid diethylcarbamoylmethyl ester,
3-(pyridin-4-ylamino)-1H-indole-2-carboxylic acid 2-morpholin-4-yl-2-oxo-ethyl ester,
3-(pyridin-4-ylamino)-1H-indole-2-carboxylic acid 2-oxo-2-pyrrolidin-1-yl-ethyl ester,
3-(pyridin-4-ylamino)-1H-indole-2-carboxylic acid 2-azetidin-1-yl-2-oxo-ethyl ester,
3-(pyridin-4-ylamino)-1H-indole-2-carboxylic acid (benzyl-ethyl-carbamoyl)-methyl ester,
3-(pyridin-4-ylamino)-1H-indole-2-carboxylic acid diethylcarbamoyloxy-methyl ester,
3-(pyridin-4-ylamino)-1H-indole-2-carboxylic acid bezylcarbamoyloxymethyl ester,
3-(pyridin-4-ylamino)-1H-indole-2-carboxylic acid piperidine-1-carbonyloxymethyl ester,
3-(pyridin-4-ylamino)-1H-indole-2-carboxylic acid morpholine-4-carbonyloxymethyl ester,
3-(pyridin-4-ylamino)-1H-indole-2-carboxylic acid 2-ethoxycarbonylamino-2-oxy-ethyl ester,
3-(pyridin-4-ylamino)-1H-indole-2-carboxylic acid isopropoxycarbonyloxy-methyl ester,
3-(pyridin-4-ylamino)-1H-indole-2-carboxylic acid 1,1,2-trimethylpropoxy-carbonyloxy-methyl ester,
3-(pyridin-4-ylamino)-1H-indole-2-carboxylic acid cyclohexyloxy-carbonyloxy-methyl ester,
3-(pyridin-4-ylamino)-1H-indole-2-carboxylic acid adamantan-1-yloxycarbonyloxymethyl ester,
3-(pyridin-4-ylamino)-1H-indole-2-carboxylic acid acetoxymethyl ester,
3-(pyridin-4-ylamino)-1H-indole-2-carboxylic acid 2,2-dimethyl-propionyloxymethyl ester,
3-(pyridin-4-ylamino)-1H-indole-2-carboxylic acid pentanoyloxymethyl ester,
3-(pyridin-4-ylamino)-1H-indole-2-carboxylic acid 2-oxo-piperidin-1-ylmethyl ester,
3-(pyridin-4-ylamino)-1H-indole-2-carboxylic acid (benzoyl-ethoxycarbonylmethyl-amino)-methyl ester,
3-(pyridin-4-ylamino)-1H-indole-2-carboxylic acid 2-oxo-pyrrolidin-1-ylmethyl ester,
3-(pyridin-4-ylamino)-1H-indole-2-carboxylic acid 5-methyl-2-oxo-(1,3)dioxo-4-ylmethyl ester,
3-(pyridin-4-ylamino)-1H-indole-2-carboxylic acid (phenyl-(toulene-4-sulfonyl)-amino)-methyl ester,
3-(pyridin-4-ylamino)-1H-indole-2-carboxylic acid (benzenesulfonyl-methyl-amino)-methyl ester,
3-(pyridin-4-ylamino)-1H-indole-2-carboxylic acid (methyl-(toulene-4-sulfonyl)-amino)-methyl ester, and
3-(pyridin-4-ylamino)-1H-indole-2-carboxylic acid tert-butoxycarbonyloxy-methyl ester.

* * * * *

SEQUENCE LISTING

```
<160> NUMBER OF SEQ ID NOS: 1

<210> SEQ ID NO 1
<211> LENGTH: 6632
<212> TYPE: DNA
<213> ORGANISM: Artificial Sequence
<220> FEATURE:
<223> OTHER INFORMATION: A 6.7 kb Fragment Comprising Nucleotides -6635
      to +66 of Human Interkeukin-4 Gene Promoter

<400> SEQUENCE: 1
gaattccttc ctgtgcgaga tccaagaact ctctcggggt ctgaatcggg acccctttt       60 ccagcaacac tgtgttcttc cccttggctt agtcaccctc catgtctact gcctgcaggc     120
tggaccctcc cctgttctca gagtatggcc cgtagcagcc cctcagctgg tggctcccac     180
ccgccgcctg ccctctcccc tgcctcctcc ccaagccaga gacctggggc cacctgcgac     240
```

-continued

```
ttcctgctct ccctcacccc cacattcagt cacttccaag tgctattaat gatgatggtg    300
gtggtgatgg tgattgctgg cattttccgg gggcttgcaa tatgccggtc accacaccaa    360
acacttcata tttgtcacct tctatagtat tccctcgccc ctgtaatcag cccagtttta    420
cagagaagcc tggatggggg aacttttcca aggtcaccca gagctgggat tcagaaccag    480
tcaggtcccg tgggcaccaa gacaccaggt cttaacctag acactgtgct gggccaaatg    540
actcaagagc ccacagctct ccctgccacc atcccacccg attcgcgcca gctgcctctg    600
tcacgggcgc tgcaatgct ctggctgggt ccctcggcc cgtgctcccc tcctgggagc      660
cctctcttca gtgacctcgg ggccttccac ctgtctgtcc cttgcccgca ctcacccac     720
cctgcagccc ctgctcctgg ctaaagccgg ctcatcccta actctgctta agtgcccctc    780
cctcagagaa gtctcacctt tttccatgac taagcctgtg ggggttggaa agcactctcc    840
tgggtgctgg cctgcaggac tgacagaaga ggagggaggt gagattcacc cgactcggac    900
cacaggaatg gctgggacag caagcatcaa tgaacgaggc ccgtggagac tgggctgcat    960
tgtgcgacct gtattccttt ctcctagttg actgccgcgt ttctgactcc tttgaagcga   1020
gcatctggct tttccaatta gatgaaggct gacaagctgt ggaggggagg gcggcagata   1080
ccatgtacct ggtcattcag actaggggtg tccttgagca gactcatggt gtggaagtca   1140
gaccgggagt ctcctggagc agactcacag tgtaggggt cagcagaggc agcagctttg    1200
gaatcccggc actgcagcct cagggtggc tcgctgagtg ggtcaggtct ttagggttct    1260
gggcccagcc tggagcctgc ccctccagcc ctcctgacat tcttagaagc acctactttc   1320
ctgcctaaat cctttcctga ctaaagcacc cacagctgtg tctgttcccc tgtaatgaat   1380
ccagatacta aagtaggcgg gctgcagtgt ggagaccgtg acccaccaga aacaaggacg   1440
gcaactcaaa gacggaggag gcacatccag gaggaacctg tggggagggc ccgtctggcc   1500
agatctccac tgccctgtcc agacttgggc ttgcctaata gatgaagcat cagtcatttc   1560
agcaactcaa gataggagtc atcattatca tcatcacact cactgtgtgc caggcactat   1620
tctaaatact tgaaaacttt aaatgtattc attcctcaga gcaacttcat gagacaggga   1680
cagctatgac ccctatttca cagatgaggc tgagtagcgt gcccaaggtc acacagccag   1740
gaggcacagc agccaggcct gacagaccac ctgggcccag cgtccgctct cttagccacc   1800
gtgtactata gcagcctctg ttaacagacc ccttctctgga tgacacatgc caagtacttt  1860
ccatggaacc actcacttgc tcctcacaag gaagagccac attattccca tttcacaggt   1920
gagaaaatcg agacccagag agagttaatg atctactcat ggtcacagag ttgataaggg   1980
ctcatttgct ggactcccaa acgcagtgct cataactgct acgttccagg gcctgaagga   2040
aaaactctgc atccatggag gggccggcgc tggttctcag ctctcacaca ggggagggga   2100
aggggcctgt gaccgacaca gccagagaca gcagtattca cctccctcct gaactttggt   2160
gtcaggccca ccacaccccg ccaaggcact gcccatggcc ctgaggctcg agactccttt  2220
cgcagtggtg gtagtggtgg tgatcactgc cctcctcttt gtccctgcaa tgcaggcacc   2280
caccttcccc atctctaccc acctgccgca cctgcagctg ccatggtgct gtccctgcag   2340
gcgaggatgg cccatccccc acttctgccc tctggggaga ctcctggtca ctctcgaatg   2400
ttctggacag tttatccttt catctttggc ctcatttcac cattgaaaca aacaaaaaag   2460
ctggattctg cttctgagct gaaggtgccc acctaatatt ccctttttcac tcaccagctc   2520
tccctcagag cctcaagccc agggtctgcc ctttagtggg tgcttagaaa aacaccagat   2580
```

-continued

```
ggaccataaa tggctgttcc actgccccca cagacgcccc agaacccgc cctccccacc    2640 agctcccctt ctgcatcccc gactctcctt gagaacctat ttggcagaag ctctccaccc    2700
agcaagtccg cagcttgatg agctcccctcc tgtgttaact ggaaccgctg ctgtacttca    2760
ttccacataa tagttatcgg atccaaagtc cccacctgct ttggaagcaa ccacctgctc    2820
ttctcataac tctcctccat ttgtgcagtg aagaatcaac ctttatccaa gaagtctggc    2880 cttttgtcctg gctcttggga ggtcctacca gctacaaacc cttggagtaa acaacgtggc    2940
tagtccttgt caccagttcc caggaggtag ccccaaattc ctagggattt cccaagtgat    3000
aggagtatct tattattcat ggtggtctct gagagtttat gcgagtgaag tgactcatgg    3060
tgggccctag gtagttttg ctgacaatac gacatggagg ggctggccac gccactgagg    3120
ttctgtgata tcagcctggc ctcccggaag gagacaggaa gatgagttca acccagtggc    3180
caatgagtcc atcaaccaca cctatatgat aagactcaaa taaaaactct ggaccccaaa    3240
gctcaagtga gcctccctgc ttagaaatag tcagcatttt gtcacacgtc aaagtgctga    3300
gaaggtgatg cctctgacgc cacacgggga agacaatgag actttgtgtt tgggcccctc    3360
ctccatctcg cccctgtgtc tcctcttttg gctggttctg atttgatgct tttgttatga    3420
taaaactgtg gccttacgta tagcactctc ctgagttctg tcagtcatcc agtgcattct    3480
ggaacctgag gggtagtgga aactcccaga tttgcagcca gtcagcagtg aggtgggctg    3540 ggaaccctg aatgtgcaac tggcgtctga agcaagggca gtgttgtggg ggaccatacc    3600
cctcacctgt gaggtgtggc tcatctcagg tggtttggca tctgaagcca ctgcatttgt    3660
ttggtaacct tgctgcccag tcccaatgga aggatcctaa atatggtcta aggacctcct    3720
gtaacaatta tccagattct ctccttcaca gaacttgagg cactgcgata agatccaaaa    3780
ctattataca cagtggaatc ctatacagcc ttaaaaaaga aggaaacgct gtcattcacc    3840
acaacaggat gaacctggag gacattatgc taagtgaaaa aatccaggca cagacagaca    3900
aataccacat gatctcacgc atatgtgaaa tataaaaaag ccaaactcag ggaggcagag    3960
agtaggatga gtcaccaggg cctgggaggg tggtgatcag gaagatgttg ctcaaaggat    4020
ataaaatttc aatgggagga gttaagttaa agagagccat tgtacgacat ggtgacaaca    4080
gttgatatca atgtttgtat acttaaaaat catgaagaca ggccaggcgc agtggctcac    4140
acctgtaatc ccagcactgc aggggctgag gtgggtagat cacctgaggt caggagttcg    4200
agaccagcct ggccaacatg gtaaaaccct gtctctatta aaaatacaaa aattagctgg    4260
gcgtggtggc aggcacctgt aaccagctac tcgggaggct gaggcaggag aattgcttga    4320
gctcaggagg cagaggttgc agtggctgag actgcgccat tgcactccag tctgggcaac    4380
agagcaagac tctatctcaa aataaatata atcacagag tagattttaa atgttcttac    4440
caaaaataaa tatgtgaagt attgtataag tagcttgatg tagcaattcc ataacatgca    4500
catttcaaaa cattatatca tacagcacaa atatgtgcaa tacttatttg tcaatttaat    4560
aataataata ataagggaag aaaagatcca aaacaggcaa accttggcc gggcatggtg    4620 gttcacgcct ataatcccag cactttggga ggctgagggg gtggatcatt ttgaggccag    4680
gagttcgaca ccagcctagc caacatggtg aaaccccatc ttactaaaaa aaaaaaaaaa    4740
atacagaaat tagccaggcg tggtggcatg tgcctgtaat cccgctactc gggaagctga    4800
ggctggagaa tgccttgagc ccaggagatc aaggctacag aaagctatga tcaccactgc    4860
actccagcct gggtgacaga gtatggggggc aggggggtggt gaggggggcg gggaagtgga    4920
acagagccaa aaccttagca acacacatt ttagatgatc ttccagaata ttcatagga    4980
```

-continued

```
ggcccaggca cagtggctca cgcctgtaat cccagcactt tgggaggccg agcaggcgga    5040
tcacgaggtc aggagatgga gaccatcctg gctaacacgt gaaacccccg tctctactaa    5100
aaatacaaaa aattagccgg gcgtggtggc aggtgcctgt agtcccagct actcgggagg    5160
ctgaggcagg agaacggcat gaacccagga ggcggagctt gcagtgaact aagatccgcc    5220
actgcactcc agcctgggtg acagagcaag attccatctc aaaaaaaaaa aaaaaaaag    5280
aaattcatag ggaaaagaag gtcagagacc aagggaaggg aaggttctgg gagaaaagcg    5340
gggcaggcag ggcccaagaa tcctgctgcc catgagccct tactgggagg tggggtggcc    5400
tgcacagggc ccaggcacct gagtgagtgg tggggtcctt acgttcactg ctggggtgag    5460
gcatgagcac cttattgtgt ccacatgaat tcaataaaaa acaagcaggg cgcgtggtgg    5520
ggcactagga gggctgattt gtaagttggt aagactgtag ctcttttttcc taattagctg    5580
aggatgtgtt aggttccatt caaaagtgg gcattcctgg ccaggcatgg tggctcacac     5640
ctgtaatctc aggctttggg agactgaggt aggaggatca cttgagccca ggaatttgag    5700
atgagcctag gcaacatagt gagactctta tctctatcaa aaaataaaaa taaaaatgag    5760
ccaggcatgg tgcggtgacc acgcacctac tgctagggggg gctgaggtgg gaggatcatt    5820
gagcctggga ggttgaggtg cagtgatccc tgatcaaaca ttgcatttca gcctgggtga    5880
cagagtgaga ccctgtctca gaaaaaaaaa aaaagtcat tcctgaaacc tcagaataga    5940
cctaccttgc caagggcttc cttagggtaa ggaccttatg gacctgctgg gacccaaact    6000
aggcctcacc tgatacgacc tgtcctctca aaacactaaa cttgggagaa cattgtcccc    6060
cagtgctggg gtaggagagt ctgcctgttt ctgcctctat gcagagaagg agccccagat    6120
catcttttcc atgacaggac agtttccaag accacctgta cttggaagaa gccaggttaa    6180
aatactttc aagtaaaact ttcttgatat tactcttctt tccccaggag gactgcatta    6240
caacaaattc ggacacctgt ggcctctccc ttctatgcaa gcaaaaagcc agcagcagcc    6300
ccaagctgat aagattaatc taaagagcaa attatggtgt aatttcctat gctgaaactt    6360
tgtagttaat tttttaaaaa ggtttcattt tcctattggt ctgattcaca ggaacatttt    6420
acctgtttgt gaggcatttt ttctcctgga agagaggtgc tgattggcca gtgactgaca    6480
atctggtgta acgaaaattt ccaatgtaaa ctcattttcc ctcggtttca gcatttaaat    6540
ctatatatag agatatcttt gtcagcattg catcgttagc ttctcctgat aaactaatgc    6600
ctcacattgt cactgcaaat cgacacctat ta                                  6632
```